United States Patent [19]

Doetzer et al.

[11] Patent Number: 5,543,433

[45] Date of Patent: Aug. 6, 1996

[54] AZINE-SUBSTITUTED PHENYLACETIC ACID DERIVATIVES AND FUNGICIDES CONTAINING THESE

[75] Inventors: Reinhard Doetzer, Weinheim; Hubert Sauter; Herbert Bayer, both of Mannheim; Franz Roehl, Schifferstadt; Gisela Lorenz, Neustadt; Eberhard Ammermann, Heppenheim; Horst Wingert, Mannheim, all of Germany

[73] Assignee: BASF Aktiengesellschaft, Ludwigshafen, Germany

[21] Appl. No.: 254,052

[22] Filed: Jun. 3, 1994

[30] Foreign Application Priority Data

Jun. 3, 1993 [DE] Germany ............ 43 18 397.2

[51] Int. Cl.[6] ............ C07C 251/24; C07C 235/34; A01N 33/26; A01N 31/04
[52] U.S. Cl. ............ 514/638; 564/163; 564/167; 564/249; 560/35; 560/37; 560/42; 514/183; 514/255; 514/247; 514/275; 514/245; 514/241; 514/228.8; 514/230.5; 514/238.5; 514/227.2; 514/226.8; 514/224.2; 514/260; 514/259; 514/256; 514/242; 514/297; 514/298; 514/248; 514/249; 514/243; 514/258; 514/261; 514/226.5; 514/227.5; 514/367; 514/393; 514/394; 514/383; 514/311; 514/307; 514/300; 514/302; 514/301; 514/303; 514/378; 514/380; 514/372; 514/392; 514/386; 514/385; 514/329; 514/331; 514/377; 514/374; 514/370; 514/365; 514/364; 514/360; 514/359; 514/361; 514/363; 514/381; 514/357; 514/379; 514/373; 514/411; 514/475; 514/449; 514/471; 514/472; 514/447; 514/438; 514/426; 514/408; 514/404; 514/403; 514/467; 514/407; 514/406; 514/401; 514/436; 514/459; 514/427; 514/400; 514/469; 514/443; 514/415; 514/416; 514/468; 514/538; 514/615; 544/382; 544/399; 544/326; 544/322; 544/335; 544/336; 544/353; 544/350; 544/400; 544/236; 544/280; 544/212; 544/278; 544/277; 544/263; 544/262; 544/255; 544/254; 544/224; 544/211; 544/216; 544/292; 544/293; 544/283; 544/237; 544/235; 544/257; 544/105; 544/164; 544/168; 544/171; 544/182; 544/179; 544/115; 544/88; 544/54; 544/0.50; 544/58.1; 546/223; 546/231; 546/332; 546/104; 546/108; 546/175; 546/174; 546/145; 546/122; 546/113; 546/115; 546/114; 546/118; 546/119; 548/245; 548/240; 548/214; 548/233; 548/215; 548/264.8; 548/267.4; 548/255; 548/204; 548/238; 548/239; 548/237; 548/248; 548/236; 548/253; 548/241; 548/207; 548/262.4; 548/331.5; 548/326.5; 548/300.1; 548/371.7; 548/356.1; 548/379.4; 548/349.1; 548/375.1; 548/336.1; 548/362.5; 548/307.4; 548/332.5; 548/557; 548/362.1; 548/569; 548/566; 548/565; 548/561; 548/505; 548/195; 548/194; 548/133; 548/131; 548/124; 548/123; 548/128; 548/136; 548/143; 548/180; 548/470; 548/444; 549/68; 549/77; 549/76; 549/21; 549/22; 549/43; 549/58; 549/480; 549/496; 549/449; 549/452; 549/451; 549/424; 549/426; 549/467; 549/461; 549/552; 549/511
[58] Field of Search ............ 564/249, 163, 564/167; 546/332; 544/224, 335; 514/638, 615, 357, 247, 275

[56] References Cited

U.S. PATENT DOCUMENTS 3,829,492  8/1974  Miller et al. .
5,254,717  10/1993  Grammenos et al. ............ 560/35

FOREIGN PATENT DOCUMENTS 0463488  1/1992  European Pat. Off. .
499823  8/1992  European Pat. Off. ...... C07C 251/48
596254  5/1994  European Pat. Off. ...... C07C 251/52
0499823A3  8/1992  Germany .
0499823A3  8/1992  Germany .

Primary Examiner—Mukund J. Shah
Assistant Examiner—King L. Wong
Attorney, Agent, or Firm—Oblon, Spivak, McClelland, Maier & Neustadt, P.C.

[57] ABSTRACT

Compounds of the formula I

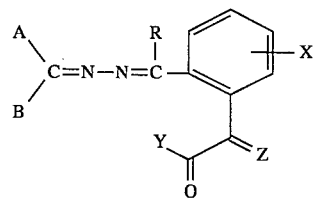

where
 X is hydrogen, halogen, alkyl, alkoxy, trifluoromethyl, cyano or nitro,
 Y is an amino, methylamino or dimethylamino group,
 Z is a group $CHCH_3$, $CHOCH_3$ or $NOCH_3$,
 R is hydrogen or alkyl,
 A is hydrogen, alkyl, haloalkyl or cycloalkyl,
 B is unsubstituted or substituted alkyl, alkenyl, alkynyl, cycloalkyl, cycloalkenyl, heterocyclyl, aryl, heteroaryl, arylalkyl, heteroarylalkyl or the group

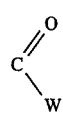

where
 W is hydrogen, alkyl, alkoxy, alkylthio, alkylamino or dialkylamino, unsubstituted or substituted aryl or heteroaryl, unsubstituted or substituted aryloxy, arylthio, arylamino or aryl-N-($C_1$-$C_6$-alkyl)amino, heteroaryloxy, heteroarylthio, heteroarylamino or heteroaryl-N-(alkyl)amino or
 A and B, together with the C atom whose substituents they are, are an isocyclic or heterocyclic ring which can also be quinonoid,
and fungicides containing these compounds.

15 Claims, No Drawings

AZINE-SUBSTITUTED PHENYLACETIC ACID DERIVATIVES AND FUNGICIDES CONTAINING THESE

The present invention relates to compounds of the formula I

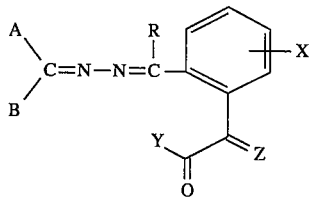

where the substituents have the following meanings

X is hydrogen, cyano, nitro, trifluoromethyl, halogen, $C_1$-$C_6$-alkyl or $C_1$-$C_6$-alkoxy;

Y is methoxy, amino, methylamino or dimethylamino;

Z is $CHCH_3$, $CHOCH_3$ or $NOCH_3$;

R is hydrogen or $C_1$-$C_6$-alkyl;

A is hydrogen, $C_1$-$C_6$-alkyl, $C_1$-$C_6$-haloalkyl or $C_3$-$C_7$-cycloalkyl;

B is unsubstituted or substituted $C_1$-$C_6$-alkyl, $C_2$-$C_6$-alkenyl, $C_2$-$C_6$-alkynyl, $C_3$-$C_7$-cycloalkyl, $C_5$-$C_7$-cycloalkenyl, an unsubstituted or substituted, saturated or partially unsaturated heterocyclyl, unsubstituted or substituted aryl, which may be fused, unsubstituted or substituted 5- or 6-membered heteroaryl, which may be benzo- or hetero-fused, unsubstituted or substituted aryl-$C_1$-$C_6$-alkyl or heteroaryl-$C_1$-$C_6$-alkyl, or $C(=O)W$;

where

W is hydrogen, unsubstituted or substituted $C_1$-$C_6$-alkyl, $C_1$-$C_6$-alkoxy, $C_1$-$C_6$-alkylthio, $C_1$-$C_6$-alkylamino or di-$C_1$-$C_6$-alkylamino, unsubstituted or substituted aryl, heteroaryl, aryloxy, arylthio, arylamino, aryl-N-($C_1$-$C_6$-alkyl)amino, heteroaryloxy, heteroarylthio, heteroarylamino or heteroaryl-N-($C_1$-$C_6$-alkyl)amino;

or

A and B, together with the C atom whose substituents they are, are an unsubstituted or substituted, saturated or unsaturated 3- to 7-membered isocyclic ring or 5- to 7-membered heterocyclic ring, which may be fused and which may also be quinonoid.

The invention additionally relates to processes for preparing these compounds, compositions containing them, and their use for the production of compositions of this type and for the control of pests and harmful fungi.

EP-A-499823 discloses the use of hydrazone-substituted phenylacetic acid derivatives as agrochemical fungicides. Their action, however, is unsatisfactory.

It is an object of the present invention to provide novel compounds having improved properties.

We have now found that this object is achieved by the compounds defined at the beginning, processes for their preparation, compositions containing them and their use.

The active compounds can be synthesized by general methods for the preparation of unsymmetrical azines, as are described eg. in Houben/Weyl, "Methoden der organischen Chemie" [Methods of Organic Chemistry] Vol. 10/2, pp.104–111 and Vol. E 14 b, Part 1, pp. 655–673.

For example (see Scheme 1), azines of the formula I can be prepared by reaction of two carbonyl compounds II and III with hydrazine, one of its acid addition salts or its hydrate in a suitable solvent and if appropriate in the presence of a catalytically active compound, eg. acetic acid, and the unsymmetrical azine I can be isolated from the additionally resulting symmetrical azines VI and VII by use of a suitable separation method such as eg. column chromatography, fractional crystallization or distillation. The compounds II are accessible by generally known methods of organic synthesis or are commercially available; the preparation of compounds III is described in EP 499823 and literature cited there.

It is also possible to bring II and a carbonyl compound VIII to reaction with hydrazine, one of its acid addition salts or its hydrate, in which case an unsymmetrical azine IX mixed with the symmetrical azines VI and X results and can be isolated by the customary separation methods. The variable V in the formulae VIII and IX is a group which can be converted to the group $Y—C(=O)—C=Z$ by standard methods of organic chemistry, for example as described for similar compounds in EP 463488, pp. 7–8. It may be advantageous first to synthesize the azines IX and then to prepare the active compound I by conversion of the group V to the group $Y—C(=O)—C=Z$. The group V is advantageously selected such that it remains unchanged under the conditions of the azine synthesis. It may also be advantageous in the starting material of the formula II to employ a functional substituent in the group B in protected form and to deprotect it after azine formation. The preparation of the carbonyl compounds VIII can be carried out by the methods of organic synthesis mentioned for III or generally known.

Furthermore, azines of the formula I or IX can be prepared by converting a carbonyl compound II to a hydrazone IV by known methods and reacting this with a carbonyl compound III or VIII in a suitable solvent and if appropriate in the presence of a catalytically active species [see eg. Liebigs Ann. Chem. 640 (1961), 37]. Also in this process, with the unsymmetrical azine I or IX, the symmetrical azines VI and VII or X can be formed as by-products which have to be separated off. Instead of the carbonyl compounds, their Schiff's bases (which can be prepared by generally known methods) can also be employed [Liebigs Ann. Chem. 657 (1962), 39]; this can be advantageous in relation to the yield and selectivity of the reaction. IX can be converted to I by standard methods (see above).

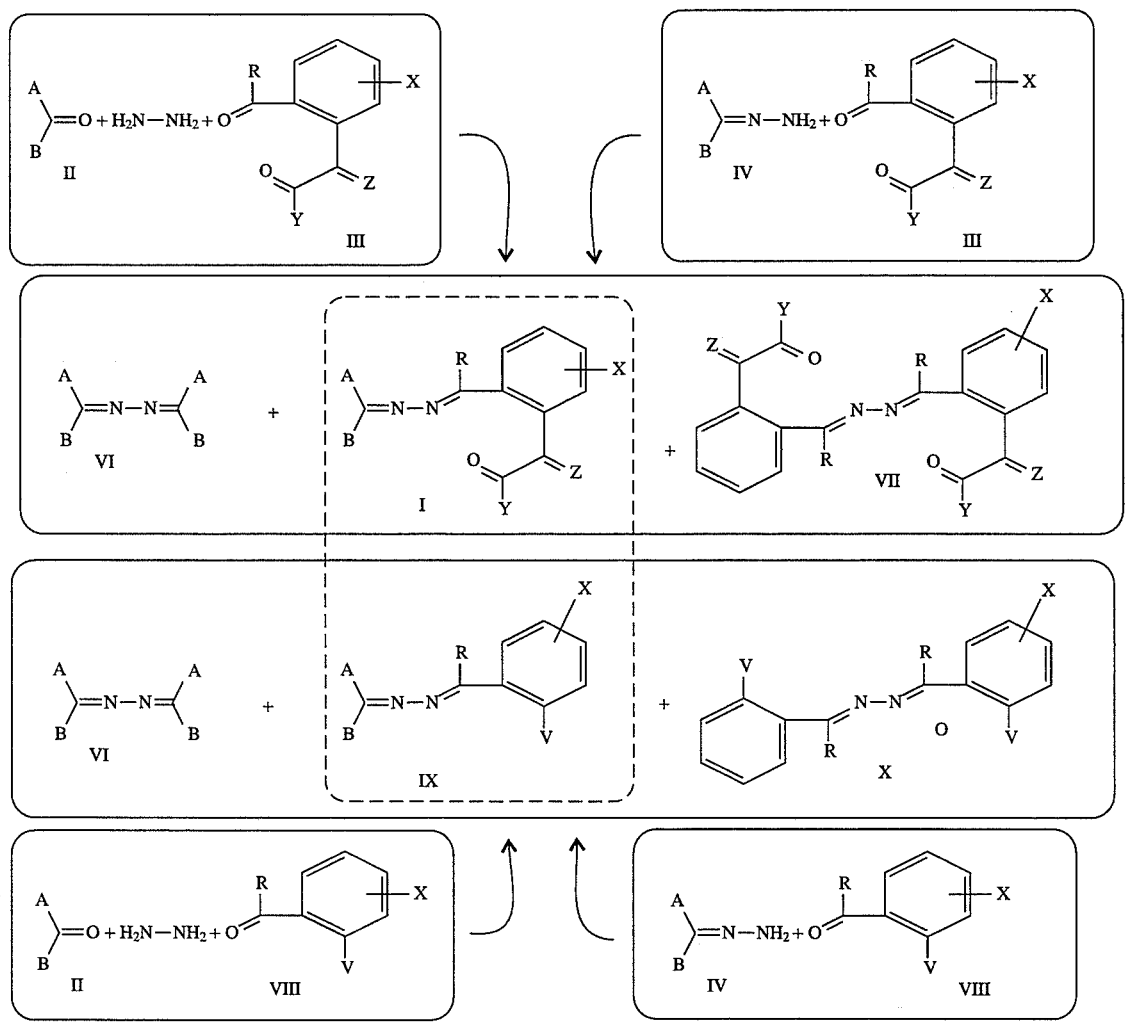

Scheme 1

It is also possible [Sulfur Lett. 9 (1989), 227], to generate hydrazones IV by thermolysis of o-ethylsulfamoylbenzoyl hydrazides XII (accessible from N-ethylsaccharin XI, for preparation see eg. J. Pharm. Soc. Jap. 75 (1955), 153) in the presence of a carbonyl compound III or VIII and to convert in situ to the azine I or IX (Scheme 2); the method may be advantageous for the selective preparation of the unsymmetrical azines.

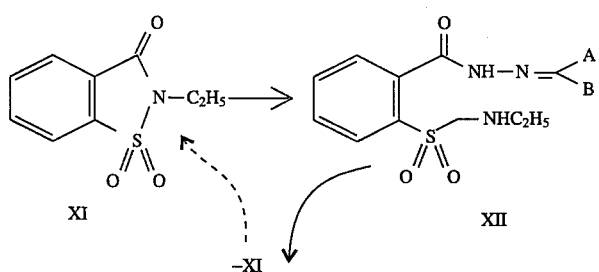

Scheme 2

-continued
Scheme 2

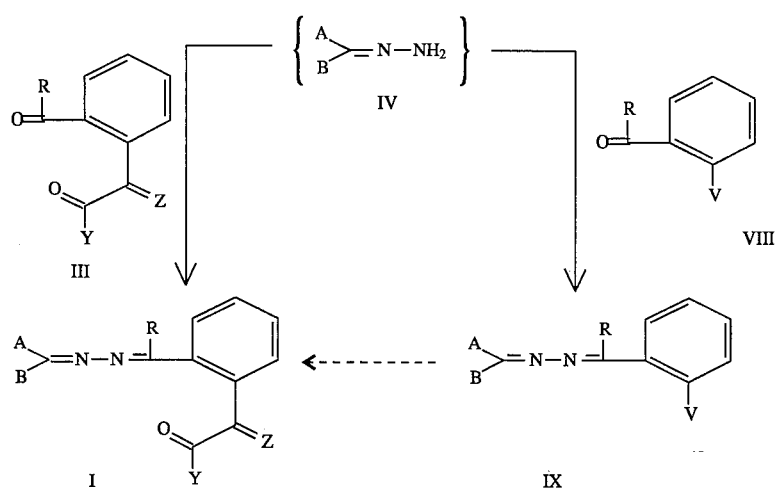

The compounds of the formula I or IX can also be prepared by reaction of carbonyl compounds III or VIII, preferably aldehydes (R=H), with phosphazines XIII or metal salts of the phosphonohydrazides XIV in an aza-analogous Wittig reaction [Chem. Ber. 94 (1961), 2477] or Horner-Emmons reaction [Synthesis 1986, 298] (Scheme 3). The synthesis of the starting materials XIII and XIV is described or mentioned in the above literature.

compound II and hydrazine, one of its acid addition salts or its hydrate or, instead of this starting material combination, a hydrazone IV with an aldehyde or ketone equivalent V (Scheme 4). The cyclic hemiaminals V are accessible by treating the carbonyl compounds XV (corresponding to compounds in which R is alkyl, preferably methyl) with methylamine in a suitable solvent, eg. water, methanol or tetrahydrofuran or a mixture of such solvents. Instead of III, Scheme 3

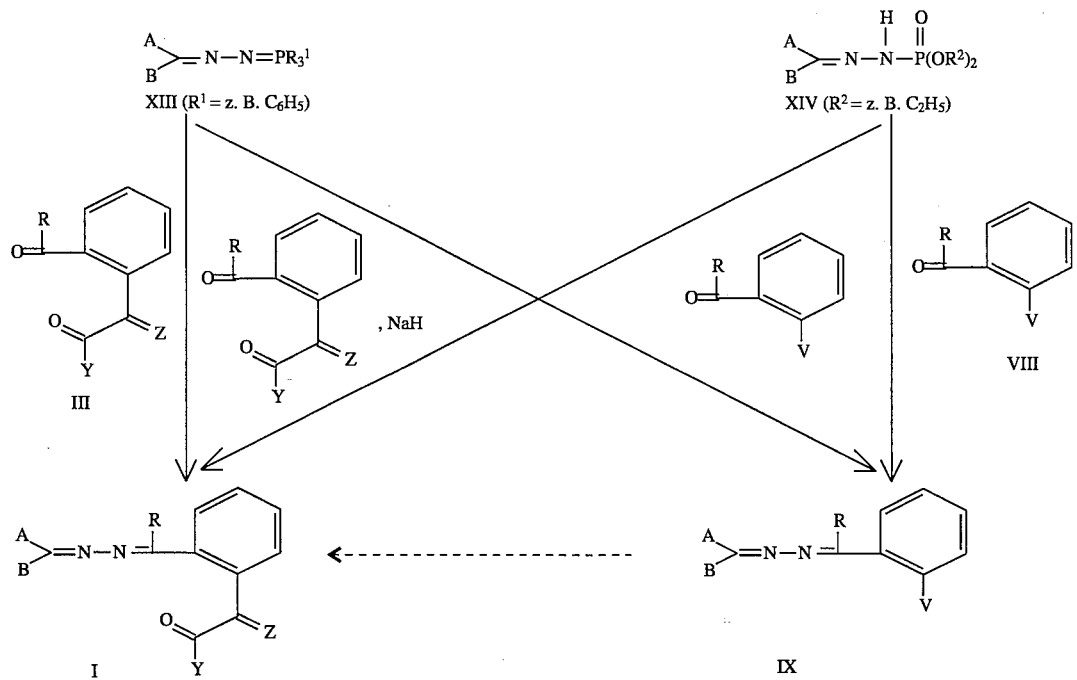

Azines XVI corresponding to the compounds of the formula I in which Z is a group NOCH$_3$ and Y is a group NHCH$_3$, can be prepared either by reacting a carbonyl V can also be reacted with XII, XIII or XIV by the methods described in Schemes 2 and 3 to give compounds of the formula XVI.

Scheme 4

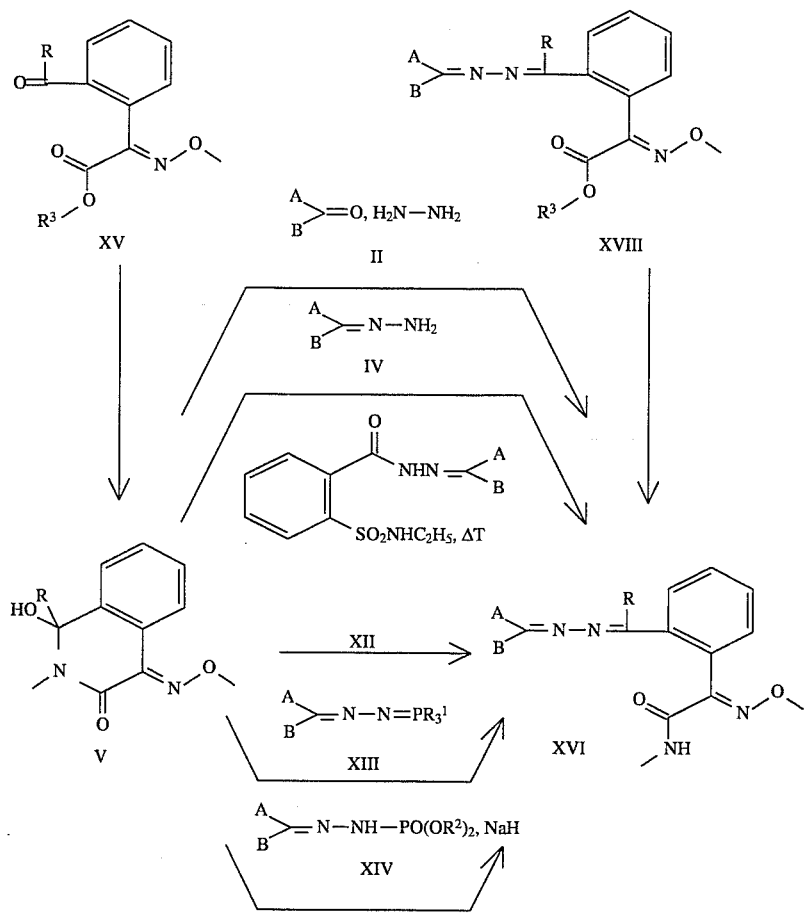

Compounds of the formula XVI can also be prepared by reacting azines of the formula XVII (corresponding to formula I, where Z=NOCH₃ and Y=OR³, R³ being short-chain alkyl, preferably methyl) with methylamine as described above. The starting materials XVII are accessible eg. by the above methods (see Schemes 1–3).

In the definitions of the symbols given in the above formulae, collective terms were used which are generally representative of the following substituents:

halogen: fluorine, chlorine, bromine and iodine;

alkyl: saturated, straight-chain or branched hydrocarbon radicals having 1 to 6 carbon atoms, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

alkoxy: straight-chain or branched alkyl groups having 1 to 6 carbon atoms (as mentioned above), which are bonded to the ring system via an oxygen atom (—O—);

alkylthio: straight-chain or branched alkyl groups having 1 to 6 carbon atoms (as mentioned above), which are bonded to the ring system via a sulfur atom (—S—);

alkylamino: a straight-chain or branched alkyl group having 1 to 6 carbon atoms (as mentioned above), which is bonded to the ring system via an amino group (—NH—);

dialkylamino: an amino group which carries two straight-chain or branched alkyl groups which are independent of one another, each having 1 to 6 carbon atoms (as mentioned above);

haloalkyl: straight-chain or branched alkyl groups having 1 to 6, preferably 1 to 4, in particular 1 to 2 carbon atoms (as mentioned above), it being possible for the hydrogen atoms in these groups to be partly or completely replaced by halogen atoms as mentioned above, eg. fluoromethyl, difluoromethyl, trifluoromethyl, 1-fluoroethyl, 2-fluoroethyl, 1,1-difluoroethyl, 1,2-difluoroethyl, 2,2-difluoroethyl, 2,2,2-trifluoroethyl, 1,1,2,2-tetrafluoroethyl, pentafluoroethyl, fluoropropyl, fluorobutyl, fluoropentyl, fluorohexyl, heptafluoropropyl, nonafluorobutyl, chloromethyl, trichloromethyl, 1-chloroethyl, 2-chloroethyl, 2,2,2-trichloroethyl, chloropropyl, chlorobutyl, chloropentyl, chlorohexyl, bromomethyl, bromoethyl, dibromoethyl and iodomethyl;

alkenyl: unsaturated, straight-chain or branched hydrocarbon radicals having 2 to 6 carbon atoms and a double bond in any desired position, eg. ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2- dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and -1-ethyl-2-methyl-2-propenyl;

alkynyl: straight-chain or branched hydrocarbon groups having 2 to 6 carbon atoms and a triple bond in any desired position, eg. $C_2$-$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-di-methyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

cycloalkyl: monocyclic or bicyclic alkyl groups having 3 to 7 carbon ring members, eg. cyclopropyl, cyclobutyl, cyclopentyl, cyclohexyl, cycloheptyl and norbornyl;

cycloalkenyl: monocyclic or bicyclic alkyl groups having 5 to 7 carbon ring members, eg. cyclopentenyl, cyclohexenyl, cycloheptenyl and norbornenyl;

heterocyclyl: saturated or partially unsaturated ring systems which, in addition to carbon ring members, can also contain 1 to 3 hetero atoms from the group consisting of oxygen, sulfur and nitrogen, eg. oxiranyl, oxetanyl, tetrahydrofur-2-yl, tetrahydrofur-3-yl, tetrahydrothien-2-yl, tetrahydrothien-3-yl, pyrrolidin-2-yl, pyrrolidin-3-yl, isoxazolidin-3-yl, isoxazolidin-4-yl, isoxazolidin-5-yl, isothiazolidin-3-yl, isothiazolidin-4-yl, isothiazolidin-5-yl, pyrazolidin-3-yl, pyrazolidin-4-yl, pyrazolidin-5-yl, oxazolidin-2-yl, oxazolidin-4-yl, oxazolidin-5-yl, thiazolidin-2-yl, thiazolidin-4-yl, thiazolidin-5-yl, imidazolidin-2-yl, imidazolidin-4-yl, 1,2,4-oxadiazolidinyl, 1,3,4-oxazolidinyl, 1,2,4-thiazolidinyl, 1,2,4-triazolidinyl, 1,2,5-triazolidinyl, 2,3-dihydrofuryl, 2,5-dihydrofuryl, 2,3-dihydrothienyl, 2,5-dihydrothienyl, 2,3-dihydropyrrolyl, 2,5-dihydropyrrolyl, 2,3-dihydroisoxazolyl, 2,5-dihydroisoxazolyl, 4,5-dihydroisoxazolyl, 2,3-dihydroisothiazolyl, 2,5-dihydroisothiazolyl, 4,5-dihydroisothiazolyl, 2,3-dihydropyrazolyl, 2,5-dihydropyrazolyl, 4,5-dihydropyrazolyl, 2,5-dihydrooxazolyl, 3,4-dihydrooxazolyl, 2,5-dihydrothiazolyl, 3,4-dihydrothiazolyl, 2,5-dihydroimidazolyl, 3,4-dihydroimidazolyl, piperidin-2-yl, piperidin-3-yl, piperidin-4-yl, tetrahydropyridazin-3-yl, tetrahydropyridazin-4-yl, tetrahydropyrimidin-2-yl, tetrahydropyrimidin-4-yl, tetrahydropyrimidin-5-yl, tetrahydropyrazin-2-yl, tetrahydro-1,3,5-triazinyl, tetrahydro-1,2,4-triazinyl, dihydro-1,3-oxazinyl, 1,3-dithian-2-yl, tetrahydropyranyl, 1,3-dioxolan-2-yl, 4H-1,3-thiazin-2-yl, 4H-3,1-benzothiazin-2-yl, 2H-1,4-benzothiazin-3-yl, 2H-1,4-benzoxazin-3-yl, 1,1-dioxotetrahydrothienyl, dihydro-1,3-oxazin-2-yl, morpholinyl or dihydroquinazolinyl;

aryl, aryloxy, arylthio and arylamino: aromatic, mono- or polycyclic hydrocarbons which are bonded to the ring system directly or via an oxygen atom (-oxy), a sulfur atom (-thio) or an amino group (-amino), eg. phenyl, naphthyl, anthryl and phenanthryl or the corresponding oxy, thio or amino groups;

arylalkyl: straight-chain or branched alkyl groups having 1 to 6 carbon atoms (as mentioned above), which can carry one of the above aryl radicals in any desired position;

arylalkylamino: alkylamino groups having 1 to 6, preferably 1 to 4, in particular 1 to 2 carbon atoms (as mentioned above), which carry one of the abovementioned aryl radicals on the nitrogen atom;

heteroaryl, heteroaryloxy, -thio and -amino: aromatic, mono- or polycyclic systems which, in addition to carbon ring members, can also contain oxygen, sulfur and/or nitrogen atoms as ring members and which are bonded to the ring system directly or via an exocyclic oxygen atom (-oxy), sulfur atom (-thio) or an amino group (-amino), eg.

5-membered heteroaryl, containing one to four nitrogen atoms or one to three nitrogen atoms and a sulfur or oxygen atom: 5-membered ring heteroaryl groups which, in addition to carbon atoms, can contain one to four nitrogen atoms or one to three nitrogen atoms and a sulfur or oxygen atom as ring members;

benzo-fused 5-membered heteroaryl, containing one to three nitrogen atoms or a nitrogen atom and an oxygen or sulfur atom: 5-membered ring heteroaryl groups which, in addition to carbon atoms, can contain one to four nitrogen atoms or one to three nitrogen atoms and a sulfur or oxygen atom as ring members, and in which two adjacent carbon ring members or a nitrogen and an adjacent carbon ring member can be bridged by a buta-1,3-dien-1,4-diyl group;

5-membered heteroaryl bonded via nitrogen, containing one to four nitrogen atoms, or benzo-fused 5-membered heteroaryl bonded via nitrogen, containing one to three nitrogen atoms: 5-membered heteroaryl groups which, in addition to carbon atoms, can contain one to four nitrogen atoms or one to three nitrogen atoms as ring members, and in which two adjacent carbon ring members or a nitrogen and an adjacent carbon ring member can be bridged by a buta-1,3-dien-1,4-diyl group, these rings being bonded to the ring system via one of the nitrogen ring members;

6-membered heteroaryl, containing one to three or one to four nitrogen atoms: 6-membered heteroaryl groups which, in addition to carbon atoms, can contain one to three or one to four nitrogen atoms as ring members;

benzo-fused 6-membered heteroaryl, containing one to three nitrogen atoms: 6-membered ring heteroaryl groups which, in addition to carbon atoms, can contain one to three nitrogen atoms as ring members, and in which two adjacent carbon ring members or a nitrogen and an adjacent carbon ring member can be bridged by a buta-1,3-dien-1,4-diyl group;

e.g. fur-2-yl, fur-3-yl, thien-2-yl, thien-3-yl, pyrrol-1-yl, pyrrol-2-yl, pyrrol-3-yl, isoxazol-3-yl, isoxazol-4-yl, isoxazol-5-yl, isothiazol-3-yl, isothiazol-4-yl, isothiazol-5-yl, pyrazol-1-yl, pyrazol-3-yl, pyrazol-4-yl, pyrazol-5-yl, oxazol-2-yl, oxazol-4-yl, oxazol-5-yl, thiazol-2-yl, thiazol-4-yl, thiazol-5-yl, imidazol-1-yl, imidazol-2-yl, imidazol-4- yl, imidazol-5-yl, 1,2,4-thiadiazolyl, 1,3,4-thiadiazolyl, 1,2,4-oxadiazolyl, t,3,4-oxadiazolyl, 1,2,4-triazolyl, tetrazolyl, pyrid-2-yl, pyrid-3-yl, pyrid-4-yl, pyridazin-3-yl, pyridazin-4-yl, pyrimidin-2-yl, pyrimidin-4-yl, pyrimidin-5-yl, pyrazin-2-yl, 1,2,4-triazinyl, 1,3,5-triazinyl and 1,2,4,5-tetrazinyl; adjacent substituents of the heteroaromatic can in this case be fused to an aromatic or heteroaromatic ring such that heteroaryl is also fused ring systems such as eg. benzofuryl, isobenzofuryl, benzothien-2-yl, benzothien-3-yl, benzothien-4-yl, benzothien-5-yl, benzothien-6-yl, benzothien-7-yl, indol-1-yl, indol-2-yl, indol-3-yl, isoindolyl, benzisoxazolyl, benzisothiazolyl, benzothiazol-2-yl, benzothiazol-4-yl, benzothiazol-5-yl, benzothiazol-6-yl, benzothiazol-7-yl, indazolyl, benzimidazolyl, benzotriazolyl, dibenzofuryl, dibenzothienyl, carbazolyl, acridinyl, phenanthridinyl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, phthalazinyl, quinazolinyl, quinoxalinyl, cinnolinyl, 1,5-naphthyridinyl, 1,6-naphthyridinyl, 1,7-naphthyridinyl, 1,8-naphthyridinyl, pteridinyl, pyrrolopyridinyl, pyrrolopyridazinyl, pyrrolopyrimidinyl, pyrrolopyrazinyl, pyrrolo-1,2,4-triazinyl, furopyridinyl, furopyridazinyl, furopyrimidinyl, furopyrazinyl, thienopyridinyl, thienopyridazinyl, thienopyrimidinyl, thienopyrazinyl, imidazopyridinyl, imidazopyridazinyl, imidazopyrimidinyl, purinyl, imidazopyrazinyl, pyrazolopyridinyl, pyrazolopyridazinyl, pyrazolopyrimidinyl, pyrazolopyrazinyl, isoxazolopyrazinyl, oxazolopyridinyl, oxazolopyrimidinyl, isothiazolopyrimidinyl and triazolopyrimidinyl or the corresponding oxy, thio and amino groups;

hetarylalkyl: straight-chain or branched alkyl groups having 1 to 6 carbon atoms (as mentioned above), which carry one of the above heteroaryl radicals in any desired position;

hetarylalkylamino: alkylamino groups having 1 to 6 carbon atoms (as mentioned above), which carry one of the abovementioned heteroaryl radicals on the nitrogen atom;

A and B, together with the C atom to which they are bonded, are a saturated or unsaturated, 3- to 7-membered isocyclic or 5- to 7-membered heterocyclic ring which may be fused or unfused, eg. cyclopropylidene, cyclobutylidene, cyclopentylidene, cyclopentenylidene, cyclohexylidene, cyclohexenylidene, cycloheptylidene, cycloheptenylidene, 4-oxohexa-2,5-dien-1-ylidene, tetrahydrothien- 3-ylidene, tetrahydropyran-4-ylidene, dihyropyran-4-ylidene, tetrahydrothiopyran-4-ylidene or piperidin-4-ylidene.

In the definition of the compounds I, a few of the substituents illustrated above were additionally described as unsubstituted or substituted. This is understood as meaning that in these radicals hydrogen atoms can be replaced by the groups described in greater detail in the following:

unsubstituted or substituted in relation to alkyl, alkenyl and alkynyl: the substituents can be partially or completely halogenated and/or carry, for example, one to three, preferably one, of the following groups:

cyano, nitro, hydroxyl, mercapto, amino, formyl, carboxyl, formyloxy, aminocarbonyl, hydroxyaminocarbonyl, formamido, aminothiocarbonyl, hydroxysulfinyl, hydroxysulfinyl, in addition alkyl, alkenyl or alkynyl groups which are bonded to the substituents via oxygen (—O—), sulfur (—S—), amino (—NH—), alkylamino [-N(alkyl)-], carbonyl (—CO—), carbonyloxy (—CO—O—), oxycarbonyl (—O—CO—), aminocarbonyl (—NH—CO—), oxyaminocarbonyl (—O—NH—CO—), carbonylamino (—CO—NH—), carbonylalkylamino [—CO—N(alkyl)-], sulfoxyl, sulfinyl, sulfinyl, sulfinyloxy or sulfinyloxy, in addition cycloalkyl, cycloalkenyl, heterocyclyl, aryl or heteroaryl groups which are bonded to the substituents directly or via oxygen (—O—), sulfur (—S—), amino (—NH—), alkylamino [-N(alkyl)-], carbonyl (—CO—), carbonyloxy (—CO—O—), oxycarbonyl (—O—CO—), aminocarbonyl (—NH—CO—), oxyaminocarbonyl (—O—NH—CO—), carbonylamino (—CO—NH—), carbonylalkylamino [—CO—N(alkyl)-], sulfoxyl, sulfinyl, sulfynyl, sulfynyloxy or sulfinyloxy, in addition trialkylsilyl (a silyl group with three $C_1$-$C_4$-alkyl radicals which are independent of one another), dialkoxyphosphinyl (a phosphinyl group having two $C_1$-$C_4$-alkoxy radicals which are independent of one another) or bis(aryloxy)phosphinyl, in addition a group —ON=CR'R", where R' is hydrogen, alkyl, alkenyl or alkynyl and R" is hydrogen, alkyl, alkoxy, alkenyl or alkynyl;

unsubstituted or substituted in relation to cycloalkyl, cycloalkenyl and heterocyclyl: the substituents can be partially or completely halogenated and/or carry, for example, one to three, preferably one, of the following groups:

cyano, nitro, hydroxyl, mercapto, amino, formyl, carboxyl, formyloxy, aminocarbonyl, hydroxyaminocarbonyl, formamido, aminothiocarbonyl, hydroxysulfinyl, hydroxysulfinyl, in addition alkyl, alkenyl or alkynyl groups which are bonded to the substituents directly or via oxygen (—O—), sulfur (—S—), amino (—NH—), alkylamino [-N(alkyl)-], carbonyl (—CO—), carbonyloxy (—CO—O—), oxycarbonyl (—O—CO—), aminocarbonyl (—NH—CO—), oxyaminocarbonyl (—O—NH—CO—), carbonylamino (—CO—NH—), carbonylalkylamino [—CO—N(alkyl)-], sulfoxyl, sulfinyl, sulfinyl, sulfinyloxy or sulfinyloxy, in addition cycloalkyl, cycloalkenyl, heterocyclyl, aryl or heteroaryl groups which are bonded to the substituents directly or via oxygen (—O—), sulfur (—S—), amino (—NH—), alkylamino [-N(alkyl)-], carbonyl (—CO—), carbonyloxy (—CO—O—), oxycarbonyl (—O—CO—), aminocarbonyl (—NH—CO—), oxyaminocarbonyl (—O—NH—CO—), carbonylamino (—CO—NH—), carbonylalkylamino [—CO—N(alkyl)-], sulfoxyl, sulfinyl, sulfinyl, sulfinyloxy or sulfinyloxy, in addition trialkylsilyl (a silyl group with three $C_1$-$C_4$-alkyl radicals which are independent of one another), dialkoxyphosphinyl (a phosphinyl group having two $C_1$-$C_4$-alkoxy radicals which are independent of one another) or bis(aryloxy)phosphinyl, in addition a group —ON=CR'R", where R' is hydrogen, alkyl, alkenyl or alkynyl and R" is hydrogen, alkyl, alkoxy, alkenyl or alkynyl;

unsubstituted or substituted in relation to aryl and heteroaryl: the substituents can be partially or completely halogenated and/or carry, for example, one to three of the following groups:

cyano, nitro, hydroxyl, mercapto, amino, formyl, carboxyl, formyloxy, aminocarbonyl, hydroxyaminocarbonyl, formamido, aminothiocarbonyl, hydroxysulfinyl, hydroxysulfinyl, in addition alkyl, alkenyl or alkynyl groups which are bonded to the substituents directly or via oxygen (—O—), sulfur (—S—), amino (—NH—), alkylamino [-N(alkyl)-], carbonyl (—CO—), carbonyloxy (—CO—O—), oxycarbonyl (—O—CO—), aminocarbonyl (—NH—CO—), oxyaminocarbonyl (—O—NH—CO—), carbonylamino (—CO—NH—), carbonylalkylamino [—CO—N(alkyl)-], sulfoxyl, sulfinyl, sulfinyl, sulfynyloxy or sulfinyloxy, in addition cycloalkyl, cycloalkenyl, heterocyclyl, aryl or heteroaryl groups which are bonded to the substituents directly or via oxygen (—O—), sulfur (—S—), amino (—NH—), alkylamino [-N(alkyl)-], carbonyl (—CO—), carbonyloxy (—CO—O—), oxycarbonyl (—O—CO—), aminocarbonyl (—NH—CO—), oxyaminocarbonyl (—O—NH—CO—), carbonylamino (—CO—NH—), carbonylalkylamino [—CO—N(alkyl)-], sulfoxyl, sulfinyl, sulfinyl, sulfinyloxy or sulfinyloxy, in addition trialkylsilyl (a silyl group with three $C_1$-$C_4$-alkyl radicals which are independent of one another), dialkoxyphosphinyl (a phosphinyl group having two $C_1$-$C_4$-alkoxy radicals which are independent of one another) or bis(aryloxy)phosphinyl, in addition a group —ON=CR'R", where R' is hydrogen, alkyl, alkenyl or alkynyl and R" is hydrogen, alkyl, alkoxy, alkenyl or alkynyl.

The expression "partially or completely halogenated" is intended to express that in the corresponding radicals the hydrogen atoms bonded to C atoms are partially or completely replaced by identical or different halogen atoms.

In the abovementioned substituents, halogen and the organic substructures in each case have the abovementioned meanings. For their parts, these substituents can again be substituted by one or more of the abovementioned radicals.

The compounds according to the invention can be obtained during preparation as stereoisomers (eg. Z/E isomers of C=C or C=N double bonds, enantiomers or diastereomers), which can be separated by the customary methods (chromatography, crystallization, distillation). Both the individual isomers and their mixtures are suitable as fungicides and are covered by the invention.

With respect to their biological action, compounds I are preferred in which X is hydrogen, chlorine, bromine, methyl or methoxy.

In addition, compounds I are preferred in which Y is methoxy and Z is methoxymethylene.

Additionally, compounds I are preferred in which Y is methoxy and Z is methoxyimino.

In addition, compounds I are preferred in which Y is methoxy and Z is methylmethylene.

Additionally, compounds I are preferred in which Y is methoxy or methylamino.

In addition, compounds I are preferred in which Y is methylamino and Z is methoxyimino.

In addition, compounds I are preferred in which Y is methylamino and Z is methoxymethylene.

In addition, compounds I are preferred in which Y is methylamino and Z is methylmethylene.

In addition, compounds I are preferred in which R is hydrogen or methyl.

In addition, compounds I are preferred in which A is hydrogen, cyclopropyl, $C_1$-$C_3$-alkyl or $C_1$-$C_2$-haloalkyl, in particular hydrogen, cyclopropyl, methyl, ethyl, isopropyl or trifluoromethyl.

Additionally, compounds I are preferred in which B is unsubstituted or substituted alkyl or cycloalkyl.

In particular, compounds I are preferred in which B is $C_1$-$C_{12}$-alkyl or $C_3$-$C_7$-cycloalkyl.

In addition, compounds I are preferred in which B is unsubstituted or substituted aryl.

In particular, compounds I are preferred in which B is aryl (particularly phenyl or naphthyl) which is partially or completely halogenated and/or carries a group —$CR^a$=$NR^b$ ($R^a$=hydrogen, amino, $C_1$-$C_4$-alkyl, $C_1$-$C_4$-alkoxy, $C_1$-$C_4$-alkylthio or $C_1$-$C_4$-alkylamino; $R^b$ =$C_1$-$C_4$-alkyl or $C_1$-$C_4$-alkoxy), and/or one to three of the following groups: cyano, nitro, hydroxyl, mercapto, formyl, carboxyl, aminocarbonyl, cyanomethyl, $C_1$-$C_6$-alkyl, $C_3$-$C_6$-cycloalkyl, $C_1$-$C_4$-haloalkyl, $C_2$-$C_4$-alkenyl, $C_2$-$C_4$-alkynyl, $C_1$-$C_6$-alkoxy, $C_3$-$C_6$-cycloalkoxy, $C_1$-$C_4$-haloalkoxy, mono- or di-$C_1$-$C_4$-alkoxy-$C_1$-$C_2$-alkyl, $C_1$-$C_4$-alkylthio, $C_3$-$C_6$-cycloalkylthio, $C_1$-$C_6$-alkylcarbonyl, $C_1$-$C_6$-alkoxycarbonyl, $C_1$-$C_6$-alkylcarbonyloxy, $C_1$-$C_4$-alkylaminocarbonyl, di-$C_1$-$C_4$-alkylaminocarbonyl, $C_1$-$C_4$-alkylcarbonylamino, $C_1$-$C_4$-alkylcarbonyl-$C_1$-$C_4$-amino, $C_1$-$C_4$-alkylsulfinyl, $C_1$-$C_4$-alkylsulfoxyl, phenyl or phenoxy, where the phenyl rings for their part can be partially or completely halogenated and/or can carry one to three of the following groups: cyano, nitro, $C_1$-$C_4$-alkyl, $C_3$-$C_6$-cycloalkyl, $C_1$-$C_4$-haloalkyl, $C_1$-$C_4$-alkoxy, $C_3$-$C_6$-cycloalkoxy and $C_1$-$C_4$-alkylthio.

In addition, compounds I are preferred in which B is unsubstituted or substituted heteroaryl.

Particularly preferred compounds I are those in which B is unsubstituted or substituted pyridyl, pyridazinyl, pyrimidinyl, pyrazinyl, quinolinyl, isoquinolinyl, cinnolinyl, quinazolinyl, quinoxalinyl, pteridinyl, furyl, thienyl, pyrryl, oxazolyl, thiazolyl, imidazolyl, isoxazolyl, isothiazolyl, pyrazolyl, oxadiazolyl, thiadiazolyl, triazolyl, triazinyl, tetrazinyl, benzofuryl, thionaphthenyl, indolyl, benzoxazolyl, benzothiazolyl, benzimidazolyl, benzisoxazolyl, benzoisothiazolyl, benzopyrazolyl or purinyl.

In particular, compounds I are preferred in which B is heteroaryl which can be partially halogenated and/or can carry one to three (preferably one or two) of the following radicals: nitro, cyanomethyl, $C_1$-$C_4$-alkyl, $C_3$-$C_6$-cycloalkyl, $C_1$-$C_4$-haloalkyl, $C_1$-$C_4$-alkoxy, $C_3$-$C_6$-cycloalkoxy, $C_1$-$C_4$-haloalkoxy, phenyl or phenoxy, where the phenyl rings for their part can be partially or completely halogenated and/or can carry one to three of the following groups: cyano, nitro, $C_1$-$C_4$-alkyl, $C_3$-$C_6$-cycloalkyl, $C_1$-$C_4$-haloalkyl, $C_1$-$C_4$-alkoxy, $C_3$-$C_6$-cycloalkoxy and $C_1$-$C_4$-alkylthio.

Additionally, compounds I are preferred in which B is a group -CO-W, where W is hydrogen, $C_1$-$C_{12}$-alkyl, $C_1$-$C_6$-alkoxy, $C_3$-$C_7$-cycloalkyl, phenyl, benzyl, phenoxy, benzyloxy, pyridyl, furyl, thiazolyl or quinolinyl.

In addition, compounds I are preferred in which A and B, together with the C atom to which they are bonded, are one of the following groups: $C_5$-$C_6$-cycloalkyl, $C_5$-$C_6$-cycloalkenyl, tetrahydronaphthyl or tetrahydrobenzopyranyl.

Particularly preferred compounds of the formula I are compiled in the following tables 1 to 16.

Table 1

Compounds of the general formula I.1 in which Y is methoxy and Z is $CHCH_3$ and the combination of the substituents A, R and $Q_m$ for a compound in each case corresponds to one line of Table A

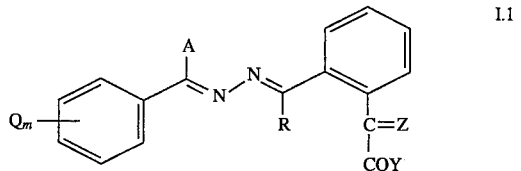

I.1

Table 2

Compounds of the general formula I.1 in which Y is methoxy and Z is $CHOCH_3$ and the combination of the substituents A, R and $Q_m$ for a compound in each case corresponds to one line of Table A.

Table 3

Compounds of the general formula I.1 in which Y is methoxy and Z is NOCH$_3$ and the combination of the substituents A, R and Q$_m$ for a compound in each case corresponds to one line of Table A.

Table 4

Compounds of the general formula I.1 in which Y is methylamino and Z is CHCH$_3$ and the combination of the substituents A, R and Q$_m$ for a compound in each case corresponds to one line of Table A.

Table 5

Compounds of the general formula I.1 in which Y is methylamino and Z is CHOCH$_3$ and the combination of the substituents A, R and Q$_m$ for a compound in each case corresponds to one line of Table A.

Table 6

Compounds of the general formula I.1 in which Y is methylamino and Z is NOCH$_3$ and the combination of the substituents A, R and Q$_m$ for a compound in each case corresponds to one line of Table A.

Table 7

Compounds of the general formula I.1 in which Y is amino and Z is CHOCH$_3$ and the combination of the substituents A, R and Q$_m$ for a compound in each case corresponds to one line of Table A.

Table 8

Compounds of the general formula I.1 in which Y is dimethylamino and Z is CHOCH$_3$ and the combination of the substituents A, R and Q$_m$ for a compound in each case corresponds to one line of Table A.

Table 9

Compounds of the general formula I.2 in which Y is methoxy and Z is CHCH$_3$ and the combination of the substituents A, B and R for a compound in each case corresponds to one line of Table B

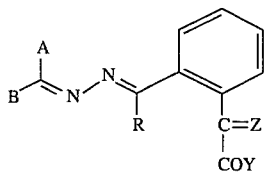

I.2

Table 10

Compounds of the general formula I.2 in which Y is methoxy and Z is CHOCH$_3$ and the combination of the substituents A, B and R for a compound in each case corresponds to one line of Table B.

Table 11

Compounds of the general formula I.2 in which Y is methoxy and Z is NOCH$_3$ and the combination of the substituents A, B and R for a compound in each case corresponds to one line of Table B.

Table 12

Compounds of the general formula I.2 in which Y is methylamino and Z is CHCH$_3$ and the combination of the substituents A, B and R for a compound in each case corresponds to one line of Table B.

Table 13

Compounds of the general formula I.2 in which Y is methylamino and Z is CHOCH$_3$ and the combination of the substituents A, B and R for a compound in each case corresponds to one line of Table B.

Table 14

Compounds of the general formula I.2 in which Y is methylamino and Z is NOCH$_3$ and the combination of the substituents A, B and R for a compound in each case corresponds to one line of Table B.

Table 15

Compounds of the general formula I.2 in which Y is amino and Z is CHOCH$_3$ and the combination of the substituents A, B and R for a compound in each case corresponds to one line of Table B.

Table 16

Compounds of the general formula I.2 in which Y is dimethylamino and Z is CHOCH$_3$ and the combination of the substituents A, B and R for a compound in each case corresponds to one line of Table B.

TABLE A

| R | A | Q$_m$ |
|---|---|---|
| H | H | H |
| H | H | 2-F |
| H | H | 3-F |
| H | H | 4-F |
| H | H | 2,3-F$_2$ |
| H | H | 2,4-F$_2$ |
| H | H | 2,5-F$_2$ |
| H | H | 2,6-F$_2$ |
| H | H | 3,4-F$_2$ |
| H | H | 3,5-F$_2$ |
| H | H | 2-Cl |
| H | H | 3-Cl |
| H | H | 4-Cl |
| H | H | 2,4-Cl$_2$ |
| H | H | 2,5-Cl$_2$ |
| H | H | 3,4-Cl$_2$ |
| H | H | 3,5-Cl$_2$ |
| H | H | 2-Br |
| H | H | 3-Br |
| H | H | 4-Br |
| H | H | 2,4-Br$_2$ |
| H | H | 3,4-Br$_2$ |
| H | H | 3,5-Br$_2$ |
| H | H | 2-I |
| H | H | 3-I |
| H | H | 4-I |
| H | H | 2-F, 4-Cl |
| H | H | 2-F, 5-Cl |
| H | H | 2-F, 4-Br |
| H | H | 2-F, 5-Br |
| H | H | 2-Cl, 4-Br |
| H | H | 2-Cl, 5-Br |
| H | H | 3-F, 4-Cl |
| H | H | 3-F, 5-Cl |
| H | H | 3-F, 4-Br |
| H | H | 3-F, 5-Br |
| H | H | 3-Cl, 4-Br |
| H | H | 3-Cl, 5-Br |
| H | H | 3-Cl, 4-F |
| H | H | 3-Br, 4-F |
| H | H | 3-Br, 4-Cl |
| H | H | 2-NO$_2$ |
| H | H | 3-NO$_2$ |
| H | H | 4-NO$_2$ |
| H | H | 2-CN |
| H | H | 3-CN |
| H | H | 4-CN |
| H | H | 2-CH$_3$ |
| H | H | 3-CH$_3$ |
| H | H | 4-CH$_3$ |
| H | H | 2,3-(CH$_3$)$_2$ |
| H | H | 2,4-(CH$_3$)$_2$ |
| H | H | 2,5-(CH$_3$)$_2$ |
| H | H | 2,6-(CH$_3$)$_2$ |
| H | R | 3,4-(CH$_3$)$_2$ |
| H | H | 3,5-(CH$_3$)$_2$ |
| H | H | 2,4,5-(CH$_3$)$_3$ |
| H | H | 2,4,6-(CH$_3$)$_3$ |
| H | H | 3,4,5-(CH$_3$)$_3$ |
| H | H | 2-C$_2$H$_5$ |
| H | H | 3-C$_2$H$_5$ |
| H | H | 4-C$_2$H$_5$ |
| H | H | 3,4-(C$_2$H$_5$)$_2$ |
| H | H | 3,5-(C$_2$H$_5$)$_2$ |
| H | H | 3-n-C$_3$H$_7$ |
| H | H | 4-n-C$_3$H$_7$ |

TABLE A-continued

| R | A | $Q_m$ |
|---|---|---|
| H | H | 3,4-(n-$C_3H_7$)$_2$ |
| H | H | 3,5-(n-$C_3H_7$)$_2$ |
| H | H | 3-i-$C_3H_7$ |
| H | H | 4-i-$C_3H_7$ |
| H | H | 3,4-(i-$C_3H_7$)$_2$ |
| H | H | 3,5-(i-$C_3H_7$)$_2$ |
| H | H | 3-Cyclopropyl |
| H | H | 4-Cyclopropyl |
| H | H | 3-n-$C_4H_9$ |
| H | H | 4-n-$C_4H_9$ |
| H | H | 3,4-(n-$C_4H_9$)$_2$ |
| H | H | 3,5-(n-$C_4H_9$)$_2$ |
| H | H | 3-s-$C_4H_9$ |
| H | H | 4-s-$C_4H_9$ |
| H | H | 3-i-$C_4H_9$ |
| H | H | 4-i-$C_4H_9$ |
| H | H | 3-t-$C_4H_9$ |
| H | H | 4-t-$C_4H_9$ |
| H | H | 3,4-(t-$C_4H_9$)$_2$ |
| H | H | 3,5-(t-$C_4H_9$)$_2$ |
| H | H | 3-n-$C_5H_{11}$ |
| H | H | 4-n-$C_5H_{11}$ |
| H | H | 3-n-$C_6H_{13}$ |
| H | H | 4-n-$C_6H_{13}$ |
| H | H | 3-Cyclohexyl |
| H | H | 4-Cyclohexyl |
| H | H | 3-Phenyl |
| H | H | 4-Phenyl |
| H | H | 3-Vinyl |
| H | H | 4-Vinyl |
| H | H | 3-Allyl |
| H | H | 4-Allyl |
| H | H | 3-Propargyl |
| H | H | 4-Propargyl |
| H | H | 3-(Propen-2-yl) |
| H | H | 4-(Propen-2-yl) |
| H | H | 2-$CH_3$, 4-$C_2H_5$ |
| H | H | 2-$CH_3$, 5-$C_2H_5$ |
| H | H | 2-$CH_3$—, 4-n-$C_3H_7$ |
| H | H | 2-$CH_3$, 5-n-$C_3H_7$ |
| H | H | 2-$CH_3$, 4-i-$C_3H_7$ |
| H | H | 2-$CH_3$, 5-i-$C_3H_7$ |
| H | H | 2-$CH_3$, 4-n-$C_4H_9$ |
| H | H | 2-$CH_3$, 4-s-$C_4H_9$ |
| H | H | 2-$CH_3$, 4-i-$C_4H_9$ |
| H | H | 2-$CH_3$, 4-t-$C_4H_9$ |
| H | H | 2-$CH_3$, 4-phenyl |
| H | H | 2-$CH_3$, 5-phenyl |
| H | H | 2-$CH_3$, 4-vinyl |
| H | H | 2-$CH_3$, 4-allyl |
| H | H | 2-$CH_3$, 4-propargyl |
| H | H | 2-$CH_3$, 4-(propen-2-yl) |
| H | H | 3-$CH_3$, 4-$C_2H_5$ |
| H | H | 3-$CH_3$, 5-$C_2H_5$ |
| H | H | 3-$CH_3$, 4-n-$C_3H_7$ |
| H | H | 3-$CH_3$, 5-n-$C_3H_7$ |
| H | H | 3-$CH_3$, 4-i-$C_3H_7$ |
| H | H | 3-$CH_3$, 5-i-$C_3H_7$ |
| H | H | 3-$CH_3$, 4-cyclopropyl |
| H | H | 3-$CH_3$, 4-t-$C_4H_9$ |
| H | H | 3-$CH_3$, 5-t-$C_4H_9$ |
| H | H | 3-$CH_3$, 4-phenyl |
| H | H | 3-$CH_3$, 5-phenyl |
| H | H | 3-$CH_3$, 4-vinyl |
| H | H | 3-$CH_3$, 4-allyl |
| H | H | 3-$CH_3$, 4-propargyl |
| H | H | 3-$CH_3$, 4-propen-2-yl |
| H | H | 3-$C_2H_5$, 4-$CH_3$ |
| H | H | 3-i-$C_3H_7$, 4-$CH_3$ |
| H | H | 3-t-$C_4H_9$, 4-$CH_3$ |
| H | H | 3-Phenyl, 4-$CH_3$ |
| H | H | 2-OH |
| H | H | 3-OH |
| H | H | 4-OH |
| H | H | 2-$OCH_3$ |
| H | H | 3-$OCH_3$ |
| H | H | 4-$OCH_3$ |
| H | H | 2,3-($OCH_3$)$_2$ |
| H | H | 2,4-($OCH_3$)$_2$ |
| H | H | 2,5-($OCH_3$)$_2$ |
| H | H | 3,4-($OCH_3$)$_2$ |
| H | H | 3,5-($OCH_3$)$_2$ |
| H | H | 3,4,5-($OCH_3$)$_3$ |
| H | H | 3-$OC_2H_5$ |
| H | H | 4-$OC_2H_5$ |
| H | H | 3,4-($OC_2H_5$)$_2$ |
| H | H | 3,5-($OC_2H_5$)$_2$ |
| H | H | 3-O-n-$C_3H_7$ |
| H | H | 4-O-n-$C_3H_7$ |
| H | H | 3-O-i-$C_3H_7$ |
| H | H | 4-O-i-$C_3H_7$ |
| H | H | 3-O-Cyclopropyl |
| H | H | 4-O-Cyclopropyl |
| H | H | 3-O-n-$C_4H_9$ |
| H | H | 4-O-n-$C_4H_9$ |
| H | H | 3-O-s-$C_4H_9$ |
| H | H | 4-O-s-$C_4H_9$ |
| H | H | 3-O-i-$C_4H_9$ |
| H | H | 4-O-i-$C_4H_9$ |
| H | H | 3-O-t-$C_4H_9$ |
| H | H | 4-O-t-$C_4H_9$ |
| H | H | 3-O-n-$C_5H_{11}$ |
| H | H | 4-O-n-$C_5H_{11}$ |
| H | H | 3-O-n-$C_6H_{13}$ |
| H | H | 4-O-n-$C_6H_{13}$ |
| H | H | 3-O-Cyclohexyl |
| H | H | 4-O-Cyclohexyl |
| H | H | 3-O-Phenyl |
| H | H | 4-O-Phenyl |
| H | H | 3-O-Allyl |
| H | H | 4-O-Allyl |
| H | H | 2-$CF_3$ |
| H | H | 3-$CF_3$ |
| H | H | 4-$CF_3$ |
| H | H | 2,4-($CF_3$)$_2$ |
| H | H | 3,5-($CF_3$)$_2$ |
| H | H | 3-$CF_2Cl$ |
| H | H | 4-$CF_2Cl$ |
| H | H | 3-$CFCl_2$ |
| H | H | 4-$CFCl_2$ |
| H | H | 3-$CCl_3$ |
| H | H | 4-$CCl_3$ |
| H | H | 3-$CH_2CH_2F$ |
| H | H | 4-$CH_2CH_2F$ |
| H | H | 3-$CH_2CF_3$ |
| H | H | 4-$CH_2CF_3$ |
| H | H | 3-$C_2F_5$ |
| H | H | 4-$C_2F_5$ |
| H | H | 3-$CHCl_2$ |
| H | H | 4-$CHCl_2$ |
| H | H | 3-$CH_2Cl$ |
| H | H | 4-$CH_2Cl$ |
| H | H | 3-$CF_2CHF_2$ |
| H | H | 4-$CF_2CHF_2$ |
| H | H | 3-$CF_2CH_2Cl$ |
| H | H | 4-$CF_2CH_2Cl$ |
| H | H | 2-$OCF_3$ |
| H | H | 3-$OCF_3$ |
| H | H | 4-$OCF_3$ |
| H | H | 3-$OCHF_2$ |
| H | H | 4-$OCHF_2$ |
| H | H | 3-$OC_2F_5$ |
| H | H | 4-$OC_2F_5$ |
| H | H | 3-$OCF_2CHF_2$ |
| H | H | 4-$OCF_2CHF_2$ |
| H | H | 3-$CH_2OCH_3$ |
| H | H | 4-$CH_2OCH_3$ |
| H | H | 3-$CH_2$O-t-$C_4H_9$ |
| H | H | 4-$CH_2$O-t-$C_4H_9$ |
| H | H | 3-C($CH_3$)($OCH_3$)$_2$ |
| H | H | 4-C($CH_3$)($OCH_3$)$_2$ |
| H | H | 3-CH($OCH_3$)$_2$ |
| H | H | 4-CH($OCH_3$)$_2$ |
| H | H | 3-$CH_2CN$ |

TABLE A-continued

| R | A | Q$_m$ |
|---|---|---|
| H | H | 4-CH$_2$CN |
| H | H | 3-CHO |
| H | H | 4-CHO |
| H | H | 3-CO—CH$_3$ |
| H | H | 4-CO—CH$_3$ |
| H | H | 3-CO—C$_2$H$_5$ |
| H | H | 4-CO—C$_2$H$_5$ |
| H | H | 2-COOH |
| H | H | 3-COOH |
| H | H | 4-COOH |
| H | H | 3-COOCH$_3$ |
| H | H | 4-COOCH$_3$ |
| H | H | 3-COOC$_2$H$_5$ |
| H | H | 4-COOC$_2$H$_5$ |
| H | H | 3-COO-n-C$_3$H$_7$ |
| H | H | 4-COO-n-C$_3$H$_7$ |
| H | H | 3-COO-i-C$_3$H$_7$ |
| H | H | 4-COO-i-C$_3$H$_7$ |
| H | H | 3-COO-n-C$_4$H$_9$ |
| H | H | 4-COO-n-C$_4$H$_9$ |
| H | H | 3-COO-s-C$_4$H$_9$ |
| H | H | 4-COO-s-C$_4$H$_9$ |
| H | H | 3-COO-i-C$_4$H$_9$ |
| H | H | 4-COO-i-C$_4$H$_9$ |
| H | H | 3-COO-t-C$_4$H$_9$ |
| H | H | 4-COO-t-C$_4$H$_9$ |
| H | H | 3-COO-n-C$_5$H$_{11}$ |
| H | H | 4-COO-n-C$_5$H$_{11}$ |
| H | H | 3-COO-n-C$_6$H$_{13}$ |
| H | H | 4-COO-n-C$_6$H$_{13}$ |
| H | H | 2-CONH$_2$ |
| H | H | 3-CONH$_2$ |
| H | H | 4-CONH$_2$ |
| H | H | 3-CONHCH$_3$ |
| H | H | 4-CONHCH$_3$ |
| H | H | 3-CON(CH$_3$)$_2$ |
| H | H | 4-CON(CH$_3$)$_2$ |
| H | H | 3-CON(C$_2$H$_5$)$_2$ |
| H | H | 4-CON(C$_2$H$_5$)$_2$ |
| H | H | 2-CSNH$_2$ |
| H | H | 3-CSNH$_2$ |
| H | H | 4-CSNH$_2$ |
| H | H | 2-NH$_2$ |
| H | H | 3-NH$_2$ |
| H | H | 4-NH$_2$ |
| H | H | 3-NHCH$_3$ |
| H | H | 4-NHCH$_3$ |
| H | H | 3-N(CH$_3$)$_2$ |
| H | H | 4-N(CH$_3$)$_2$ |
| H | H | 3-NHCO—CH$_3$ |
| H | H | 4-NHCO—CH$_3$ |
| H | H | 3-NCH$_3$—CO—CH$_3$ |
| H | H | 4-NCH$_3$—CO—CH$_3$ |
| H | H | 3-NHCOOCH$_3$ |
| H | H | 4-NHCOOCH$_3$ |
| H | H | 3-NCH$_3$—COOCH$_3$ |
| H | H | 4-NCH$_3$—COOCH$_3$ |
| H | H | 3-OCO—CH$_3$ |
| H | H | 4-OCO—CH$_3$ |
| H | H | 3-OCO-t-C$_4$H$_9$ |
| H | H | 4-OCO-t-C$_4$H$_9$ |
| H | H | 3-SH |
| H | H | 4-SH |
| H | H | 3-SCH$_3$ |
| H | H | 4-SCH$_3$ |
| H | H | 3-S-t-C$_4$H$_9$ |
| H | H | 4-S-t-C$_4$H$_9$ |
| H | H | 3-SO—CH$_3$ |
| H | H | 4-SO—CH$_3$ |
| H | H | 3-SO$_2$CH$_3$ |
| H | H | 4-SO$_2$CH$_3$ |
| H | H | 3-CH=NCH$_3$ |
| H | H | 4-CH=NCH$_3$ |
| H | H | 3-C(CH$_3$)=NCH$_3$ |
| H | H | 4-C(CH$_3$)=NCH$_3$ |
| H | H | 3-C(SCH$_3$)=NOCH$_3$ |
| H | H | 4-C(SCH$_3$)=NOCH$_3$ |
| H | H | 3-C(OCH$_3$)=NOCH$_3$ |
| H | H | 4-C(OCH$_3$)=NOCH$_3$ |
| H | H | 3-C(NH$_2$)=NOCH$_3$ |
| H | H | 4-C(NH$_2$)=NOCH$_3$ |
| H | H | 3-C(NHCH$_3$)=NOCH$_3$ |
| H | H | 4-C(NHCH$_3$)=NOCH$_3$ |
| H | H | 3-CH=NOCH$_3$ |
| H | H | 4-CH=NOCH$_3$ |
| H | H | 3-C(CH$_3$)=NOCH$_3$ |
| H | H | 4-C(CH$_3$)=NOCH$_3$ |
| H | H | 3-C(CH$_3$)=NOC$_2$H$_5$ |
| H | H | 4-C(CH$_3$)=NOC$_2$H$_5$ |
| H | H | 3-C(CH$_3$)=NO-n-C$_3$H$_7$ |
| H | H | 4-C(CH$_3$)=NO-n-C$_3$H$_7$ |
| H | H | 3-C(CH$_3$)=NO-i-C$_3$H$_7$ |
| H | H | 4-C(CH$_3$)=NO-i-C$_3$H$_7$ |
| H | H | 3-C(CH$_3$)=NO-n-C$_4$H$_9$ |
| H | H | 4-C(CH$_3$)=NO-n-C$_4$H$_9$ |
| H | H | 3-C(CH$_3$)=NO-s-C$_4$H$_9$ |
| H | H | 4-C(CH$_3$)=NO-s-C$_4$H$_9$ |
| H | H | 3-C(CH$_3$)=NO-i-C$_4$H$_9$ |
| H | H | 4-C(CH$_3$)=NO-i-C$_4$H$_9$ |
| H | H | 3-C(CH$_3$)=NO-t-C$_4$H$_9$ |
| H | H | 4-C(CH$_3$)=NO-t-C$_4$H$_9$ |
| H | H | 3-C(CH$_3$)=NO-n-C$_5$H$_{11}$ |
| H | H | 4-C(CH$_3$)=NO-n-C$_5$H$_{11}$ |
| H | H | 3-C(CH$_3$)=NO-n-C$_6$H$_{13}$ |
| H | H | 4-C(CH$_3$)=NO-n-C$_6$H$_{13}$ |
| H | H | 2-Cl, 4-CH$_3$ |
| H | H | 2-Cl, 5-CH$_3$ |
| H | H | 3-Cl, 4-CH$_3$ |
| H | H | 3-Cl, 5-CH$_3$ |
| H | H | 2-CH$_3$, 4-Cl |
| H | H | 2-CH$_3$, 5-Cl |
| H | H | 3-CH$_3$, 4-Cl |
| H | H | 3-Cl, 5-t-C$_4$H$_9$ |
| H | H | 2-Cl, 4-t-C$_4$H$_9$ |
| H | H | 2-F, 4-CH$_3$ |
| H | H | 3-F, 4-CH$_3$ |
| H | H | 3-F, 5-CH$_3$ |
| H | H | 2-CH$_3$, 4-F |
| H | H | 3-CH$_3$, 4-F |
| H | H | 2-F, 4-t-C$_4$H$_9$ |
| H | H | 3-F, 4-t-C$_4$H$_9$ |
| H | H | 2-F, 4-OCH$_3$ |
| H | H | 2-Br, 4-CH$_3$ |
| H | H | 3-Br, 4-CH$_3$ |
| H | H | 3-Br, 5-CH$_3$ |
| H | H | 2-CH$_3$, 4-Br |
| H | H | 3-CH$_3$, 4-Br |
| H | H | 2-Br, 4-t-C$_4$H$_9$ |
| H | H | 2-Cl, 4-NO$_2$ |
| H | H | 3-Cl, 4-NO$_2$ |
| H | H | 3-Cl, 5-NO$_2$ |
| H | H | 3-NO$_2$, 4-Cl |
| H | H | 3-Cl, 4-OCH |
| H | H | 3-OCH$_3$, 4-Cl |
| H | H | 2-Cl, 5-CF$_3$ |
| H | H | 3-Cl, 4-CF$_3$ |
| H | H | 3-Cl, 5-CF$_3$ |
| H | H | 3-CF$_3$, 4-Cl |
| H | H | 3-Cl, 5-OCF$_3$ |
| H | H | 3-F, 5-CF$_3$ |
| H | H | 2-CH$_3$, 4-CN |
| H | H | 3-NO$_2$, 4-CH$_3$ |
| H | H | 2-CH$_3$, 4-OCH$_3$ |
| H | H | 3-CH$_3$, 4-OCH$_3$ |
| H | H | 3-CH$_3$, 5-OCH$_3$ |
| H | H | 3-OCH$_3$, 4-CH$_3$ |
| H | H | 2-CH$_3$, 4-O-i-C$_3$H$_7$ |
| H | H | 3-CH$_3$, 4-O-i-C$_3$H$_7$ |
| H | H | 3-O-i-C$_3$H$_7$, 4-CH$_3$ |
| H | H | 2-CH$_3$, 4-CF$_3$ |
| H | H | 2-CH$_3$, 5-CF$_3$ |
| H | H | 3-CH$_3$, 4-CF$_3$ |
| H | H | 3-CH$_3$, 5-CF$_3$ |
| H | H | 3-CF$_3$, 4-CH$_3$ |

TABLE A-continued

| R | A | Q_m |
|---|---|---|
| H | H | 3-CF$_3$, 4-OCH$_3$ |
| H | H | 3-OCH$_3$, 4-CF$_3$ |
| H | H | 2-CH$_3$, 4-C(CH$_3$)=NOCH$_3$ |
| H | H | 3-CH$_3$, 4-C(CH$_3$)=NOCH$_3$ |
| H | H | 2-OH, 5-CH$_3$ |
| H | H | 3-CH$_3$, 4-OC$_2$H$_5$ |
| H | H | 3-CH$_3$, 4-O-t-C$_4$H$_9$ |
| H | H | 3-OC$_2$H$_5$, 4-CH$_3$ |
| H | H | 3-O-t-C$_4$H$_9$, 4-CH$_3$ |
| H | H | 2-C(COOCH$_3$)=NOCH$_3$ |
| H | H | 2,3-Butadienyl |
| H | H | 3,4-Butadienyl |
| CH$_3$ | H | H |
| CH$_3$ | H | 2-F |
| CH$_3$ | H | 3-F |
| CH$_3$ | H | 4-F |
| CH$_3$ | H | 2,4-F$_2$ |
| CH$_3$ | H | 3,4-F$_2$ |
| CH$_3$ | H | 3,5-F$_2$ |
| CH$_3$ | H | 2-Cl |
| CH$_3$ | H | 3-Cl |
| CH$_3$ | H | 4-Cl |
| CH$_3$ | H | 2,4-Cl$_2$ |
| CH$_3$ | H | 3,4-Cl$_2$ |
| CH$_3$ | H | 3,5-Cl$_2$ |
| CH$_3$ | H | 2-Br |
| CH$_3$ | H | 3-Br |
| CH$_3$ | H | 4-Br |
| CH$_3$ | H | 3,5-Br$_2$ |
| CH$_3$ | H | 3-I |
| CH$_3$ | H | 4-I |
| CH$_3$ | H | 3-F, 5-Cl |
| CH$_3$ | H | 3-F, 5-Br |
| CH$_3$ | H | 3-Cl, 5-Br |
| CH$_3$ | H | 3-Br, 4-F |
| CH$_3$ | H | 2-NO$_2$ |
| CH$_3$ | H | 3-NO$_2$ |
| CH$_3$ | H | 4-NO$_2$ |
| CH$_3$ | H | 2-CN |
| CH$_3$ | H | 3-CN |
| CH$_3$ | H | 4-CN |
| CH$_3$ | H | 2-CH$_3$ |
| CH$_3$ | H | 3-CH$_3$ |
| CH$_3$ | H | 4-CH$_3$ |
| CH$_3$ | H | 2,4-(CH$_3$)$_2$ |
| CH$_3$ | H | 2,5-(CH$_3$)$_2$ |
| CH$_3$ | H | 3,4-(CH$_3$)$_2$ |
| CH$_3$ | H | 3,5-(CH$_3$)$_2$ |
| CH$_3$ | H | 2,4,5-(CH$_3$)$_3$ |
| CH$_3$ | H | 2,4,6-(CH$_3$)$_3$ |
| CH$_3$ | H | 3-C$_2$H$_5$ |
| CH$_3$ | H | 4-C$_2$H$_5$ |
| CH$_3$ | H | 3,4-(C$_2$H$_5$)$_2$ |
| CH$_3$ | H | 3,5-(C$_2$H$_5$)$_2$ |
| CH$_3$ | H | 3-n-C$_3$H$_7$ |
| CH$_3$ | H | 4-n-C$_3$H$_7$ |
| CH$_3$ | H | 3-i-C$_3$H$_7$ |
| CH$_3$ | H | 4-i-C$_3$H$_7$ |
| CH$_3$ | H | 3-Cyclopropyl |
| CH$_3$ | H | 4-Cyclopropyl |
| CH$_3$ | H | 3-n-C$_4$H$_9$ |
| CH$_3$ | H | 4-n-C$_4$H$_9$ |
| CH$_3$ | H | 3-t-C$_4$H$_9$ |
| CH$_3$ | H | 4-t-C$_4$H$_9$ |
| CH$_3$ | H | 3-n-C$_6$H$_{13}$ |
| CH$_3$ | H | 4-n-C$_6$H$_{13}$ |
| CH$_3$ | H | 3-Cyclohexyl |
| CH$_3$ | H | 4-Cyclohexyl |
| CH$_3$ | H | 3-Phenyl |
| CH$_3$ | H | 4-Phenyl |
| CH$_3$ | H | 4-Allyl |
| CH$_3$ | H | 4-Propargyl |
| CH$_3$ | H | 2-CH$_3$, 4-C$_2$H$_5$ |
| CH$_3$ | H | 2-CH$_3$, 4-i-C$_3$H$_7$ |
| CH$_3$ | H | 2-CH$_3$, 4-t-C$_4$H$_9$ |
| CH$_3$ | H | 2-CH$_3$, 4-phenyl |
| CH$_3$ | H | 3-CH$_3$, 4-phenyl |

TABLE A-continued

| R | A | Q_m |
|---|---|---|
| CH$_3$ | H | 3-OH |
| CH$_3$ | H | 4-OH |
| CH$_3$ | H | 3-OCH$_3$ |
| CH$_3$ | H | 4-OCH$_3$ |
| CH$_3$ | H | 3,4-(OCH$_3$)$_2$ |
| CH$_3$ | H | 3,5-(OCH$_3$)$_2$ |
| CH$_3$ | H | 3,4,5-(OCH$_3$)$_3$ |
| CH$_3$ | H | 4-OC$_2$H$_5$ |
| CH$_3$ | H | 4-O-i-C$_3$H$_7$ |
| CH$_3$ | H | 3-O-t-C$_4$H$_9$ |
| CH$_3$ | H | 4-O-t-C$_4$H$_9$ |
| CH$_3$ | H | 4-O-n-C$_6$H$_{13}$ |
| CH$_3$ | H | 3-O-Phenyl |
| CH$_3$ | H | 4-O-Phenyl |
| CH$_3$ | H | 4-O-Allyl |
| CH$_3$ | H | 2-CF$_3$ |
| CH$_3$ | H | 3-CF$_3$ |
| CH$_3$ | H | 4-CF$_3$ |
| CH$_3$ | H | 3,5-(CF$_3$)$_2$ |
| CH$_3$ | H | 4-CH$_2$CF$_3$ |
| CH$_3$ | H | 4-C$_2$F$_5$ |
| CH$_3$ | H | 4-CF$_2$CHF$_2$ |
| CH$_3$ | H | 3-OCF$_3$ |
| CH$_3$ | H | 4-OCF$_3$ |
| CH$_3$ | H | 4-OCH$_2$CF$_3$ |
| CH$_3$ | H | 4-OC$_2$F$_5$ |
| CH$_3$ | H | 4-OCF$_2$CHF$_2$ |
| CH$_3$ | H | 3-CH$_2$OCH$_3$ |
| CH$_3$ | H | 4-CH$_2$OCH$_3$ |
| CH$_3$ | H | 4-CH$_2$—O-t-C$_4$H$_9$ |
| CH$_3$ | H | 4-CH(OCH$_3$)$_2$ |
| CH$_3$ | H | 4-CH$_2$CN |
| CH$_3$ | H | 3-CHO |
| CH$_3$ | H | 4-CHO |
| CH$_3$ | H | 3-CO—CH$_3$ |
| CH$_3$ | H | 4-CO—CH$_3$ |
| CH$_3$ | H | 3-COOH |
| CH$_3$ | H | 4-COOH |
| CH$_3$ | H | 3-COOCH$_3$ |
| CH$_3$ | H | 4-COOCH$_3$ |
| CH$_3$ | H | 3-COOC$_2$H$_5$ |
| CH$_3$ | H | 4-COOC$_2$H$_5$ |
| CH$_3$ | H | 3-COO-i-C$_3$H$_7$ |
| CH$_3$ | H | 4-COO-i-C$_3$H$_7$ |
| CH$_3$ | H | 3-COO-t-C$_4$H$_9$ |
| CH$_3$ | H | 4-COO-t-C$_4$H$_9$ |
| CH$_3$ | H | 3-COO-n-C$_6$H$_{13}$ |
| CH$_3$ | H | 4-COO-n-C$_6$H$_{13}$ |
| CH$_3$ | H | 3-CONH$_2$ |
| CH$_3$ | H | 4-CONH$_2$ |
| CH$_3$ | H | 3-CONHCH$_3$ |
| CH$_3$ | H | 4-CONHCH$_3$ |
| CH$_3$ | H | 3-CON(CH$_3$)$_2$ |
| CH$_3$ | H | 4-CON(CH$_3$)$_2$ |
| CH$_3$ | H | 3-CSNH$_2$ |
| CH$_3$ | H | 4-CSNH$_2$ |
| CH$_3$ | H | 3-NH$_2$ |
| CH$_3$ | H | 4-NH$_2$ |
| CH$_3$ | H | 4-NHCH$_3$ |
| CH$_3$ | H | 4-N(CH$_3$)$_2$ |
| CH$_3$ | H | 3-NHCO—CH$_3$ |
| CH$_3$ | H | 4-NHCO—CH$_3$ |
| CH$_3$ | H | 4-NCH$_3$—CO—CH$_3$ |
| CH$_3$ | H | 4-NHCOOCH$_3$ |
| CH$_3$ | H | 4-NCH$_3$—COOCH$_3$ |
| CH$_3$ | H | 3-OCO—CH$_3$ |
| CH$_3$ | H | 4-OCO—CH$_3$ |
| CH$_3$ | H | 4-OCO-t-C$_4$H$_9$ |
| CH$_3$ | H | 4-SH |
| CH$_3$ | H | 4-SCH$_3$ |
| CH$_3$ | H | 4-S-t-C$_4$H$_9$ |
| CH$_3$ | H | 4-SO—CH$_3$ |
| CH$_3$ | H | 4-SO$_2$—CH$_3$ |
| CH$_3$ | H | 4-C(CH$_3$)=NCH$_3$ |
| CH$_3$ | H | 4-C(SCH$_3$)=NOCH$_3$ |
| CH$_3$ | H | 4-C(OCH$_3$)=NOCH$_3$ |
| CH$_3$ | H | 3-CH=NOCH$_3$ |

TABLE A-continued

| R | A | Q_m |
|---|---|-----|
| CH₃ | H | 4-CH=NOCH₃ |
| CH₃ | H | 3-C(CH₃)=NOCH₃ |
| CH₃ | H | 4-C(CH₃)=NOCH₃ |
| CH₃ | H | 4-C(CH₃)=NOC₂H₅ |
| CH₃ | H | 4-C(CH₃)=NO-n-C₃H₇ |
| CH₃ | H | 4-C(CH₃)=NO-i-C₃H₇ |
| CH₃ | H | 4-C(CH₃)=NO-n-C₄H₉ |
| CH₃ | H | 4-C(CH₃)=NO-t-C₄H₉ |
| CH₃ | H | 4-C(CH₃)=NO-n-C₅H₁₁ |
| CH₃ | H | 4-C(CH₃)=NO-n-C₆H₁₃ |
| CH₃ | H | 2-Cl, 4-CH₃ |
| CH₃ | H | 3-Cl, 5-CH₃ |
| CH₃ | H | 2-CH₃, 4-Cl |
| CH₃ | H | 3-CH₃, 4-Cl |
| CH₃ | H | 3-F, 5-CH₃ |
| CH₃ | H | 3-Br, 5-CH₃ |
| CH₃ | H | 3-Cl, 5-NO₂ |
| CH₃ | H | 3-NO₂, 4-Cl |
| CH₃ | H | 3-Cl, 4-OCH₃ |
| CH₃ | H | 3-OCH₃, 4-Cl |
| CH₃ | H | 3-Cl, 5-CF₃ |
| CH₃ | H | 3-Cl, 5-OCF₃ |
| CH₃ | H | 3-F, 5-CF₃ |
| CH₃ | H | 2-CH₃, 4-CN |
| CH₃ | H | 2-CH₃, 4-OCH₃ |
| CH₃ | H | 2-CH₃, 4-CF₃ |
| CH₃ | H | 2-CH₃, 4-C(CH₃)=NOCH₃ |
| CH₃ | H | 3-CH₃, 4-C(CH₃)=NOCH₃ |
| CH₃ | H | 2-OH, 5-CH₃ |
| CH₃ | H | 3-CH₃, 4-O-t-C₄H₉ |
| CH₃ | H | 2-C(COOCH₃)=NOCH₃ |
| CH₃ | H | 2,3-Butadienyl |
| CH₃ | H | 3,4-Butadienyl |
| H | CH₃ | H |
| H | CH₃ | 2-F |
| H | CH₃ | 3-F |
| H | CH₃ | 4-F |
| H | CH₃ | 2,3-F₂ |
| H | CH₃ | 2,4-F₂ |
| H | CH₃ | 2,5-F₂ |
| H | CH₃ | 2,6-F₂ |
| H | CH₃ | 3,4-F₂ |
| H | CH₃ | 3,5-F₂ |
| H | CH₃ | 2-Cl |
| H | CH₃ | 3-Cl |
| H | CH₃ | 4-Cl |
| H | CH₃ | 2,4-Cl₂ |
| H | CH₃ | 2,5-Cl₂ |
| H | CH₃ | 3,4-Cl₂ |
| H | CH₃ | 3,5-Cl₂ |
| H | CH₃ | 2-Br |
| H | CH₃ | 3-Br |
| H | CH₃ | 4-Br |
| H | CH₃ | 2,4-Br₂ |
| H | CH₃ | 3,4-Br₂ |
| H | CH₃ | 3,5-Br₂ |
| H | CH₃ | 2-I |
| H | CH₃ | 3-I |
| H | CH₃ | 4-I |
| H | CH₃ | 2-F, 4-Cl |
| H | CH₃ | 2-F, 5-Cl |
| H | CH₃ | 2-F, 4-Br |
| H | CH₃ | 2-F, 5-Br |
| H | CH₃ | 2-Cl, 4-Br |
| H | CH₃ | 2-Cl, 5-Br |
| H | CH₃ | 3-F, 4-Cl |
| H | CH₃ | 3-F, 5-Cl |
| H | CH₃ | 3-F, 4-Br |
| H | CH₃ | 3-F, 5-Br |
| H | CH₃ | 3-Cl, 4-Br |
| H | CH₃ | 3-Cl, 5-Br |
| H | CH₃ | 3-Cl, 4-F |
| H | CH₃ | 3-Br, 4-F |
| H | CH₃ | 3-Br, 4-Cl |
| H | CH₃ | 2-NO₂ |
| H | CH₃ | 3-NO₂ |
| H | CH₃ | 4-NO₂ |
| H | CH₃ | 2-CN |
| H | CH₃ | 3-CN |
| H | CH₃ | 4-CN |
| H | CH₃ | 2-CH₃ |
| H | CH₃ | 3-CH₃ |
| H | CH₃ | 4-CH₃ |
| H | CH₃ | 2,3-(CH₃)₂ |
| H | CH₃ | 2,4-(CH₃)₂ |
| H | CH₃ | 2,5-(CH₃)₂ |
| H | CH₃ | 2,6-(CH₃)₂ |
| H | CH₃ | 3,4-(CH₃)₂ |
| H | CH₃ | 3,5-(CH₃)₂ |
| H | CH₃ | 2,4,5-(CH₃)₃ |
| H | CH₃ | 2,4,6-(CH₃)₃ |
| H | CH₃ | 3,4,5-(CH₃)₃ |
| H | CH₃ | 2-C₂H₅ |
| H | CH₃ | 3-C₂H₅ |
| H | CH₃ | 4-C₂H₅ |
| H | CH₃ | 3,4-(C₂H₅)₂ |
| H | CH₃ | 3,5-(C₂H₅)₂ |
| H | CH₃ | 3-n-C₃H₇ |
| H | CH₃ | 4-n-C₃H₇ |
| H | CH₃ | 3,4-(n-C₃H₇)₂ |
| H | CH₃ | 3,5-(n-C₃H₇)₂ |
| H | CH₃ | 3-i-C₃H₇ |
| H | CH₃ | 4-i-C₃H₇ |
| H | CH₃ | 3,4-(i-C₃H₇)₂ |
| H | CH₃ | 3,5-(i-C₃H₇)₂ |
| H | CH₃ | 3-Cyclopropyl |
| H | CH₃ | 4-Cyclopropyl |
| H | CH₃ | 3-n-C₄H₉ |
| H | CH₃ | 4-n-C₄H₉ |
| H | CH₃ | 3,4-(n-C₄H₉)₂ |
| H | CH₃ | 3,5-(n-C₄H₉)₂ |
| H | CH₃ | 3-s-C₄H₉ |
| H | CH₃ | 4-s-C₄H₉ |
| H | CH₃ | 3-i-C₄H₉ |
| H | CH₃ | 4-i-C₄H₉ |
| H | CH₃ | 3-t-C₄H₉ |
| H | CH₃ | 4-t-C₄H₉ |
| H | CH₃ | 3,4-(t-C₄H₉)₂ |
| H | CH₃ | 3,5-(t-C₄H₉)₂ |
| H | CH₃ | 3-n-C₅H₁₁ |
| H | CH₃ | 4-n-C₅H₁₁ |
| H | CH₃ | 3-n-C₆H₁₃ |
| H | CH₃ | 4-n-C₆H₁₃ |
| H | CH₃ | 3-Cyclohexyl |
| H | CH₃ | 4-Cyclohexyl |
| H | CH₃ | 3-Phenyl |
| H | CH₃ | 4-Phenyl |
| H | CH₃ | 3-Vinyl |
| H | CH₃ | 4-Vinyl |
| H | CH₃ | 3-Allyl |
| H | CH₃ | 4-Allyl |
| H | CH₃ | 3-Propargyl |
| H | CH₃ | 4-Propargyl |
| H | CH₃ | 3-(Propen-2-yl) |
| H | CH₃ | 4-(Propen-2-yl) |
| H | CH₃ | 2-CH₃, 4-C₂H₅ |
| H | CH₃ | 2-CH₃, 5-C₂H₅ |
| H | CH₃ | 2-CH₃—, 4-n-C₃H₇ |
| H | CH₃ | 2-CH₃, 5-n-C₃H₇ |
| H | CH₃ | 2-CH₃, 4-i-C₃H₇ |
| H | CH₃ | 2-CH₃, 5-i-C₃H₇ |
| H | CH₃ | 2-CH₃, 4-n-C₄H₉ |
| H | CH₃ | 2-CH₃, 4-s-C₄H₉ |
| H | CH₃ | 2-CH₃, 4-i-C₄H₉ |
| H | CH₃ | 2-CH₃, 4-t-C₄H₉ |
| H | CH₃ | 2-CH₃, 4-phenyl |
| H | CH₃ | 2-CH₃, 5-phenyl |
| H | CH₃ | 2-CH₃, 4-vinyl |
| H | CH₃ | 2-CH₃, 4-allyl |
| H | CH₃ | 2-CH₃, 4-propargyl |
| H | CH₃ | 2-CH₃, 4-(propen-2-yl) |
| H | CH₃ | 3-CH₃, 4-C₂H₅ |
| H | CH₃ | 3-CH₃, 5-C₂H₅ |
| H | CH₃ | 3-CH₃, 4-n-C₃H₇ |

TABLE A-continued

| R | A | Q_m |
|---|---|---|
| H | $CH_3$ | 3-$CH_3$, 5-n-$C_3H_7$ |
| H | $CH_3$ | 3-$CH_3$, 4-i-$C_3H_7$ |
| H | $CH_3$ | 3-$CH_3$, 5-i-$C_3H_7$ |
| H | $CH_3$ | 3-$CH_3$, 4-cyclopropyl |
| H | $CH_3$ | 3-$CH_3$, 4-t-$C_4H_9$ |
| H | $CH_3$ | 3-$CH_3$, 5-t-$C_4H_9$ |
| H | $CH_3$ | 3-$CH_3$, 4-phenyl |
| H | $CH_3$ | 3-$CH_3$, 5-phenyl |
| H | $CH_3$ | 3-$CH_3$, 4-vinyl |
| H | $CH_3$ | 3-$CH_3$, 4-allyl |
| H | $CH_3$ | 3-$CH_3$, 4-propargyl |
| H | $CH_3$ | 3-$CH_3$, 4-propen-2-yl |
| H | $CH_3$ | 3-$C_2H_5$, 4-$CH_3$ |
| H | $CH_3$ | 3-i-$C_3H_7$, 4-$CH_3$ |
| H | $CH_3$ | 3-t-$C_4H_9$, 4-$CH_3$ |
| H | $CH_3$ | 3-Phenyl, 4-$CH_3$ |
| H | $CH_3$ | 2-OH |
| H | $CH_3$ | 3-OH |
| H | $CH_3$ | 4-OH |
| H | $CH_3$ | 2-$OCH_3$ |
| H | $CH_3$ | 3-$OCH_3$ |
| H | $CH_3$ | 4-$OCH_3$ |
| H | $CH_3$ | 2,3-$(OCH_3)_2$ |
| H | $CH_3$ | 2,4-$(OCH_3)_2$ |
| H | $CH_3$ | 2,5-$(OCH_3)_2$ |
| H | $CH_3$ | 3,4-$(OCH_3)_2$ |
| H | $CH_3$ | 3,5-$(OCH_3)_2$ |
| H | $CH_3$ | 3,4,5-$(OCH_3)_3$ |
| H | $CH_3$ | 3-$OC_2H_5$ |
| H | $CH_3$ | 4-$OC_2H_5$ |
| H | $CH_3$ | 3,4-$(OC_2H_5)_2$ |
| H | $CH_3$ | 3,5-$(OC_2H_5)_2$ |
| H | $CH_3$ | 3-O-n-$C_3H_7$ |
| H | $CH_3$ | 4-O-n-$C_3H_7$ |
| H | $CH_3$ | 3-O-i-$C_3H_7$ |
| H | $CH_3$ | 4-O-i-$C_3H_7$ |
| H | $CH_3$ | 3-O-Cyclopropyl |
| H | $CH_3$ | 4-O-Cyclopropyl |
| H | $CH_3$ | 3-O-n-$C_4H_9$ |
| H | $CH_3$ | 4-O-n-$C_4H_9$ |
| H | $CH_3$ | 3-O-s-$C_4H_9$ |
| H | $CH_3$ | 4-O-s-$C_4H_9$ |
| H | $CH_3$ | 3-O-i-$C_4H_9$ |
| H | $CH_3$ | 4-O-i-$C_4H_9$ |
| H | $CH_3$ | 3-O-t-$C_4H_9$ |
| H | $CH_3$ | 4-O-t-$C_4H_9$ |
| H | $CH_3$ | 3-O-n-$C_5H_{11}$ |
| H | $CH_3$ | 4-O-n-$C_5H_{11}$ |
| H | $CH_3$ | 3-O-n-$C_6H_{13}$ |
| H | $CH_3$ | 4-O-n-$C_6H_{13}$ |
| H | $CH_3$ | 3-O-Cyclohexyl |
| H | $CH_3$ | 4-O-Cyclohexyl |
| H | $CH_3$ | 3-O-Phenyl |
| H | $CH_3$ | 4-O-Phenyl |
| H | $CH_3$ | 3-O-Allyl |
| H | $CH_3$ | 4-O-Allyl |
| H | $CH_3$ | 2-$CF_3$ |
| H | $CH_3$ | 3-$CF_3$ |
| H | $CH_3$ | 4-$CF_3$ |
| H | $CH_3$ | 2,4-$(CF_3)_2$ |
| H | $CH_3$ | 3,5-$(CF_3)_2$ |
| H | $CH_3$ | 3-$CF_2Cl$ |
| H | $CH_3$ | 4-$CF_2Cl$ |
| H | $CH_3$ | 3-$CFCl_2$ |
| H | $CH_3$ | 4-$CFCl_2$ |
| H | $CH_3$ | 3-$CCl_3$ |
| H | $CH_3$ | 4-$CCl_3$ |
| H | $CH_3$ | 3-$CH_2CH_2F$ |
| H | $CH_3$ | 4-$CH_2CH_2F$ |
| H | $CH_3$ | 3-$CH_2CF_3$ |
| H | $CH_3$ | 4-$CH_2CF_3$ |
| H | $CH_3$ | 3-$C_2F_5$ |
| H | $CH_3$ | 4-$C_2F_5$ |
| H | $CH_3$ | 3-$CHCl_2$ |
| H | $CH_3$ | 4-$CHCl_2$ |
| H | $CH_3$ | 3-$CH_2Cl$ |
| H | $CH_3$ | 4-$CH_2Cl$ |
| H | $CH_3$ | 3-$CF_2CHF_2$ |
| H | $CH_3$ | 4-$CF_2CHF_2$ |
| H | $CH_3$ | 3-$CH_2CH_2Cl$ |
| H | $CH_3$ | 4-$CH_2CH_2Cl$ |
| H | $CH_3$ | 2-$OCF_3$ |
| H | $CH_3$ | 3-$OCF_3$ |
| H | $CH_3$ | 4-$OCF_3$ |
| H | $CH_3$ | 3-$OCHF_2$ |
| H | $CH_3$ | 4-$OCHF_2$ |
| H | $CH_3$ | 3-$OC_2F_5$ |
| H | $CH_3$ | 4-$OC_2F_5$ |
| H | $CH_3$ | 3-$OCF_2CHF_2$ |
| H | $CH_3$ | 4-$OCF_2CHF_2$ |
| H | $CH_3$ | 3-$CH_2OCH_3$ |
| H | $CH_3$ | 4-$CH_2OCH_3$ |
| H | $CH_3$ | 3-$CH_2$O-t-$C_4H_9$ |
| H | $CH_3$ | 4-$CH_2$O-t-$C_4H_9$ |
| H | $CH_3$ | 3-$C(CH_3)(OCH_3)_2$ |
| H | $CH_3$ | 4-$C(CH_3)(OCH_3)_2$ |
| H | $CH_3$ | 3-$CH(OCH_3)_2$ |
| H | $CH_3$ | 4-$CH(OCH_3)_2$ |
| H | $CH_3$ | 3-$CH_2CN$ |
| H | $CH_3$ | 4-$CH_2CN$ |
| H | $CH_3$ | 3-CHO |
| H | $CH_3$ | 4-CHO |
| H | $CH_3$ | 3-CO—$CH_3$ |
| H | $CH_3$ | 4-CO—$CH_3$ |
| H | $CH_3$ | 3-CO—$C_2H_5$ |
| H | $CH_3$ | 4-CO—$C_2H_5$ |
| H | $CH_3$ | 2-COOH |
| H | $CH_3$ | 3-COOH |
| H | $CH_3$ | 4-COOH |
| H | $CH_3$ | 3-$COOCH_3$ |
| H | $CH_3$ | 4-$COOCH_3$ |
| H | $CH_3$ | 3-$COOC_2H_5$ |
| H | $CH_3$ | 4-$COOC_2H_5$ |
| H | $CH_3$ | 3-COO-n-$C_3H_7$ |
| H | $CH_3$ | 4-COO-n-$C_3H_7$ |
| H | $CH_3$ | 3-COO-i-$C_3H_7$ |
| H | $CH_3$ | 4-COO-i-$C_3H_7$ |
| H | $CH_3$ | 3-COO-n-$C_4H_9$ |
| H | $CH_3$ | 4-COO-n-$C_4H_9$ |
| H | $CH_3$ | 3-COO-s-$C_4H_9$ |
| H | $CH_3$ | 4-COO-s-$C_4H_9$ |
| H | $CH_3$ | 3-COO-i-$C_4H_9$ |
| H | $CH_3$ | 4-COO-i-$C_4H_9$ |
| H | $CH_3$ | 3-COO-t-$C_4H_9$ |
| H | $CH_3$ | 4-COO-t-$C_4H_9$ |
| H | $CH_3$ | 3-COO-n-$C_5H_{11}$ |
| H | $CH_3$ | 4-COO-n-$C_5H_{11}$ |
| H | $CH_3$ | 3-COO-n-$C_6H_{13}$ |
| H | $CH_3$ | 4-COO-n-$C_6H_{13}$ |
| H | $CH_3$ | 2-$CONH_2$ |
| H | $CH_3$ | 3-$CONH_2$ |
| H | $CH_3$ | 4-$CONH_2$ |
| H | $CH_3$ | 3-$CONHCH_3$ |
| H | $CH_3$ | 4-$CONHCH_3$ |
| H | $CH_3$ | 3-$CON(CH_3)_2$ |
| H | $CH_3$ | 4-$CON(CH_3)_2$ |
| H | $CH_3$ | 3-$CON(C_2H_5)_2$ |
| H | $CH_3$ | 4-$CON(C_2H_5)_2$ |
| H | $CH_3$ | 2-$CSNH_2$ |
| H | $CH_3$ | 3-$CSNH_2$ |
| H | $CH_3$ | 4-$CSNH_2$ |
| H | $CH_3$ | 2-$NH_2$ |
| H | $CH_3$ | 3-$NH_2$ |
| H | $CH_3$ | 4-$NH_2$ |
| H | $CH_3$ | 3-$NHCH_3$ |
| H | $CH_3$ | 4-$NHCH_3$ |
| H | $CH_3$ | 3-$N(CH_3)_2$ |
| H | $CH_3$ | 4-$N(CH_3)_2$ |
| H | $CH_3$ | 3-NHCO—$CH_3$ |
| H | $CH_3$ | 4-NHCO—$CH_3$ |
| H | $CH_3$ | 3-$NCH_3$—CO—$CH_3$ |
| H | $CH_3$ | 4-$NCH_3$—CO—$CH_3$ |
| H | $CH_3$ | 3-$NHCOOCH_3$ |
| H | $CH_3$ | 4-$NHCOOCH_3$ |

TABLE A-continued

| R | A | $Q_m$ |
|---|---|---|
| H | $CH_3$ | 3-$NCH_3$—$COOCH_3$ |
| H | $CH_3$ | 4-$NCH_3$—$COOCH_3$ |
| H | $CH_3$ | 3-OCO—$CH_3$ |
| H | $CH_3$ | 4-OCO—$CH_3$ |
| H | $CH_3$ | 3-OCO-t-$C_4H_9$ |
| H | $CH_3$ | 4-OCO-t-$C_4H_9$ |
| H | $CH_3$ | 3-SH |
| H | $CH_3$ | 4-SH |
| H | $CH_3$ | 3-$SCH_3$ |
| H | $CH_3$ | 4-$SCH_3$ |
| H | $CH_3$ | 3-S-t-$C_4H_9$ |
| H | $CH_3$ | 4-S-t-$C_4H_9$ |
| H | $CH_3$ | 3-SO—$CH_3$ |
| H | $CH_3$ | 4-SO—$CH_3$ |
| H | $CH_3$ | 3-$SO_2CH_3$ |
| H | $CH_3$ | 4-$SO_2CH_3$ |
| H | $CH_3$ | 3-CH=$NCH_3$ |
| H | $CH_3$ | 4-CH=$NCH_3$ |
| H | $CH_3$ | 3-C($CH_3$)=$NCH_3$ |
| H | $CH_3$ | 4-C($CH_3$)=$NCH_3$ |
| H | $CH_3$ | 3-C($SCH_3$)=$NOCH_3$ |
| H | $CH_3$ | 4-C($SCH_3$)=$NOCH_3$ |
| H | $CH_3$ | 3-C($OCH_3$)=$NOCH_3$ |
| H | $CH_3$ | 4-C($OCH_3$)=$NOCH_3$ |
| H | $CH_3$ | 3-C($NH_2$)=$NOCH_3$ |
| H | $CH_3$ | 4-C($NH_2$)=$NOCH_3$ |
| H | $CH_3$ | 3-C($NHCH_3$)=$NOCH_3$ |
| H | $CH_3$ | 4-C($NHCH_3$)=$NOCH_3$ |
| H | $CH_3$ | 3-CH=$NOCH_3$ |
| H | $CH_3$ | 4-CH=$NOCH_3$ |
| H | $CH_3$ | 3-C($CH_3$)=$NOCH_3$ |
| H | $CH_3$ | 4-C($CH_3$)=$NOCH_3$ |
| H | $CH_3$ | 3-C($CH_3$)=$NOC_2H_5$ |
| H | $CH_3$ | 4-C($CH_3$)=$NOC_2H_5$ |
| H | $CH_3$ | 3-C($CH_3$)=NO-n-$C_3H_7$ |
| H | $CH_3$ | 4-C($CH_3$)=NO-n-$C_3H_7$ |
| H | $CH_3$ | 3-C($CH_3$)=NO-i-$C_3H_7$ |
| H | $CH_3$ | 4-C($CH_3$)=NO-i-$C_3H_7$ |
| H | $CH_3$ | 3-C($CH_3$)=NO-n-$C_4H_9$ |
| H | $CH_3$ | 4-C($CH_3$)=NO-n-$C_4H_9$ |
| H | $CH_3$ | 3-C($CH_3$)=NO-s-$C_4H_9$ |
| H | $CH_3$ | 4-C($CH_3$)=NO-s-$C_4H_9$ |
| H | $CH_3$ | 3-C($CH_3$)=NO-i-$C_4H_9$ |
| H | $CH_3$ | 4-C($CH_3$)=NO-i-$C_4H_9$ |
| H | $CH_3$ | 3-C($CH_3$)=NO-t-$C_4H_9$ |
| H | $CH_3$ | 4-C($CH_3$)=NO-t-$C_4H_9$ |
| H | $CH_3$ | 3-C($CH_3$)=NO-n-$C_5H_{11}$ |
| H | $CH_3$ | 4-C($CH_3$)=NO-n-$C_5H_{11}$ |
| H | $CH_3$ | 3-C($CH_3$)=NO-n-$C_6H_{13}$ |
| H | $CH_3$ | 4-C($CH_3$)=NO-n-$C_6H_{13}$ |
| H | $CH_3$ | 2-Cl, 4-$CH_3$ |
| H | $CH_3$ | 2-Cl, 5-$CH_3$ |
| H | $CH_3$ | 3-Cl, 4-$CH_3$ |
| H | $CH_3$ | 3-Cl, 5-$CH_3$ |
| H | $CH_3$ | 2-$CH_3$, 4-Cl |
| H | $CH_3$ | 2-$CH_3$, 5-Cl |
| H | $CH_3$ | 3-$CH_3$, 4-Cl |
| H | $CH_3$ | 3-Cl, 5-t-$C_4H_9$ |
| H | $CH_3$ | 2-Cl, 4-t-$C_4H_9$ |
| H | $CH_3$ | 2-F, 4-$CH_3$ |
| H | $CH_3$ | 3-F, 4-$CH_3$ |
| H | $CH_3$ | 3-F, 5-$CH_3$ |
| H | $CH_3$ | 2-$CH_3$, 4-F |
| H | $CH_3$ | 3-$CH_3$, 4-F |
| H | $CH_3$ | 2-F, 4-t-$C_4H_9$ |
| H | $CH_3$ | 3-F, 4-t-$C_4H_9$ |
| H | $CH_3$ | 2-F, 4-$OCH_3$ |
| H | $CH_3$ | 2-Br, 4-$CH_3$ |
| H | $CH_3$ | 3-Br, 4-$CH_3$ |
| H | $CH_3$ | 3-Br, 5-$CH_3$ |
| H | $CH_3$ | 2-$CH_3$, 4-Br |
| H | $CH_3$ | 3-$CH_3$, 4-Br |
| H | $CH_3$ | 2-Br, 4-t-$C_4H_9$ |
| H | $CH_3$ | 2-Cl, 4-$NO_2$ |
| H | $CH_3$ | 3-Cl, 4-$NO_2$ |
| H | $CH_3$ | 3-Cl, 5-$NO_2$ |
| H | $CH_3$ | 3-$NO_2$, 4-Cl |
| H | $CH_3$ | 3-Cl, 4-OCH |
| H | $CH_3$ | 3-$OCH_3$, 4-Cl |
| H | $CH_3$ | 2-Cl, 5-$CF_3$ |
| H | $CH_3$ | 3-Cl, 4-$CF_3$ |
| H | $CH_3$ | 3-Cl, 5-$CF_3$ |
| H | $CH_3$ | 3-$CF_3$, 4-Cl |
| H | $CH_3$ | 3-Cl, 5-$OCF_3$ |
| H | $CH_3$ | 3-F, 5-$CF_3$ |
| H | $CH_3$ | 2-$CH_3$, 4-CN |
| H | $CH_3$ | 3-$NO_2$, 4-$CH_3$ |
| H | $CH_3$ | 2-$CH_3$, 4-$OCH_3$ |
| H | $CH_3$ | 3-$CH_3$, 4-$OCH_3$ |
| H | $CH_3$ | 3-$CH_3$, 5-$OCH_3$ |
| H | $CH_3$ | 3-$OCH_3$, 4-$CH_3$ |
| H | $CH_3$ | 2-$CH_3$, 4-O-i-$C_3H_7$ |
| H | $CH_3$ | 3-$CH_3$, 4-O-i-$C_3H_7$ |
| H | $CH_3$ | 3-O-i-$C_3H_7$, 4-$CH_3$ |
| H | $CH_3$ | 2-$CH_3$, 4-$CF_3$ |
| H | $CH_3$ | 2-$CH_3$, 5-$CF_3$ |
| H | $CH_3$ | 3-$CH_3$, 4-$CF_3$ |
| H | $CH_3$ | 3-$CH_3$, 5-$CF_3$ |
| H | $CH_3$ | 3-$CF_3$, 4-$CH_3$ |
| H | $CH_3$ | 3-$CF_3$, 4-$OCH_3$ |
| H | $CH_3$ | 3-$OCH_3$, 4-$CF_3$ |
| H | $CH_3$ | 2-$CH_3$, 4-C($CH_3$)=$NOCH_3$ |
| H | $CH_3$ | 3-$CH_3$, 4-C($CH_3$)=$NOCH_3$ |
| H | $CH_3$ | 2-OH, 5-$CH_3$ |
| H | $CH_3$ | 3-$CH_3$, 4-$OC_2H_5$ |
| H | $CH_3$ | 3-$CH_3$, 4-O-t-$C_4H_9$ |
| H | $CH_3$ | 3-$OC_2H_5$, 4-$CH_3$ |
| H | $CH_3$ | 3-O-t-$C_4H_9$, 4-$CH_3$ |
| H | $CH_3$ | 2-C($COOCH_3$)=$NOCH_3$ |
| H | $CH_3$ | 2,3-Butadienyl |
| H | $CH_3$ | 3,4-Butadienyl |
| $CH_3$ | $CH_3$ | H |
| $CH_3$ | $CH_3$ | 2-F |
| $CH_3$ | $CH_3$ | 3-F |
| $CH_3$ | $CH_3$ | 4-F |
| $CH_3$ | $CH_3$ | 2,4-$F_2$ |
| $CH_3$ | $CH_3$ | 3,4-$F_2$ |
| $CH_3$ | $CH_3$ | 3,5-$F_2$ |
| $CH_3$ | $CH_3$ | 2-Cl |
| $CH_3$ | $CH_3$ | 3-Cl |
| $CH_3$ | $CH_3$ | 4-Cl |
| $CH_3$ | $CH_3$ | 2,4-$Cl_2$ |
| $CH_3$ | $CH_3$ | 3,4-$Cl_2$ |
| $CH_3$ | $CH_3$ | 3,5-$Cl_2$ |
| $CH_3$ | $CH_3$ | 2-Br |
| $CH_3$ | $CH_3$ | 3-Br |
| $CH_3$ | $CH_3$ | 4-Br |
| $CH_3$ | $CH_3$ | 3,5-$Br_2$ |
| $CH_3$ | $CH_3$ | 3-I |
| $CH_3$ | $CH_3$ | 4-I |
| $CH_3$ | $CH_3$ | 3-F, 5-Cl |
| $CH_3$ | $CH_3$ | 3-F, 5-Br |
| $CH_3$ | $CH_3$ | 3-Cl, 5-Br |
| $CH_3$ | $CH_3$ | 3-Br, 4-F |
| $CH_3$ | $CH_3$ | 2-$NO_2$ |
| $CH_3$ | $CH_3$ | 3-$NO_2$ |
| $CH_3$ | $CH_3$ | 4-$NO_2$ |
| $CH_3$ | $CH_3$ | 2-CN |
| $CH_3$ | $CH_3$ | 3-CN |
| $CH_3$ | $CH_3$ | 4-CN |
| $CH_3$ | $CH_3$ | 2-$CH_3$ |
| $CH_3$ | $CH_3$ | 3-$CH_3$ |
| $CH_3$ | $CH_3$ | 4-$CH_3$ |
| $CH_3$ | $CH_3$ | 2,4-($CH_3$)$_2$ |
| $CH_3$ | $CH_3$ | 2,5-($CH_3$)$_2$ |
| $CH_3$ | $CH_3$ | 3,4-($CH_3$)$_2$ |
| $CH_3$ | $CH_3$ | 3,5-($CH_3$)$_2$ |
| $CH_3$ | $CH_3$ | 2,4,5-($CH_3$)$_3$ |
| $CH_3$ | $CH_3$ | 2,4,6-($CH_3$)$_3$ |
| $CH_3$ | $CH_3$ | 3-$C_2H_5$ |
| $CH_3$ | $CH_3$ | 4-$C_2H_5$ |
| $CH_3$ | $CH_3$ | 3,4-($C_2H_5$)$_2$ |
| $CH_3$ | $CH_3$ | 3,5-($C_2H_5$)$_2$ |
| $CH_3$ | $CH_3$ | 3-n-$C_3H_7$ |

TABLE A-continued

| R | A | Q_m |
|---|---|-----|
| CH$_3$ | CH$_3$ | 4-n-C$_3$H$_7$ |
| CH$_3$ | CH$_3$ | 3-i-C$_3$H$_7$ |
| CH$_3$ | CH$_3$ | 4-i-C$_3$H$_7$ |
| CH$_3$ | CH$_3$ | 3-Cyclopropyl |
| CH$_3$ | CH$_3$ | 4-Cyclopropyl |
| CH$_3$ | CH$_3$ | 3-n-C$_4$H$_9$ |
| CH$_3$ | CH$_3$ | 4-n-C$_4$H$_9$ |
| CH$_3$ | CH$_3$ | 3-t-C$_4$H$_9$ |
| CH$_3$ | CH$_3$ | 4-t-C$_4$H$_9$ |
| CH$_3$ | CH$_3$ | 3-n-C$_6$H$_{13}$ |
| CH$_3$ | CH$_3$ | 4-n-C$_6$H$_{13}$ |
| CH$_3$ | CH$_3$ | 3-Cyclohexyl |
| CH$_3$ | CH$_3$ | 4-Cyclohexyl |
| CH$_3$ | CH$_3$ | 3-Phenyl |
| CH$_3$ | CH$_3$ | 4-Phenyl |
| CH$_3$ | CH$_3$ | 4-Allyl |
| CH$_3$ | CH$_3$ | 4-Propargyl |
| CH$_3$ | CH$_3$ | 2-CH$_3$, 4-C$_2$H$_5$ |
| CH$_3$ | CH$_3$ | 2-CH$_3$, 4-i-C$_3$H$_7$ |
| CH$_3$ | CH$_3$ | 2-CH$_3$, 4-t-C$_4$H$_9$ |
| CH$_3$ | CH$_3$ | 2-CH$_3$, 4-phenyl |
| CH$_3$ | CH$_3$ | 3-CH$_3$, 4-phenyl |
| CH$_3$ | CH$_3$ | 3-OH |
| CH$_3$ | CH$_3$ | 4-OH |
| CH$_3$ | CH$_3$ | 3-OCH$_3$ |
| CH$_3$ | CH$_3$ | 4-OCH$_3$ |
| CH$_3$ | CH$_3$ | 3,4-(OCH$_3$)$_2$ |
| CH$_3$ | CH$_3$ | 3,5-(OCH$_3$)$_2$ |
| CH$_3$ | CH$_3$ | 3,4,5-(OCH$_3$)$_3$ |
| CH$_3$ | CH$_3$ | 4-OC$_2$H$_5$ |
| CH$_3$ | CH$_3$ | 4-O-i-C$_3$H$_7$ |
| CH$_3$ | CH$_3$ | 3-O-t-C$_4$H$_9$ |
| CH$_3$ | CH$_3$ | 4-O-t-C$_4$H$_9$ |
| CH$_3$ | CH$_3$ | 4-O-n-C$_6$H$_{13}$ |
| CH$_3$ | CH$_3$ | 3-O-Phenyl |
| CH$_3$ | CH$_3$ | 4-O-Phenyl |
| CH$_3$ | CH$_3$ | 4-O-Allyl |
| CH$_3$ | CH$_3$ | 2-CF$_3$ |
| CH$_3$ | CH$_3$ | 3-CF$_3$ |
| CH$_3$ | CH$_3$ | 4-CF$_3$ |
| CH$_3$ | CH$_3$ | 3,5-(CF$_3$)$_2$ |
| CH$_3$ | CH$_3$ | 4-CH$_2$CF$_3$ |
| CH$_3$ | CH$_3$ | 4-C$_2$F$_5$ |
| CH$_3$ | CH$_3$ | 4-CF$_2$CHF$_2$ |
| CH$_3$ | CH$_3$ | 3-OCF$_3$ |
| CH$_3$ | CH$_3$ | 4-OCF$_3$ |
| CH$_3$ | CH$_3$ | 4-OCH$_2$CF$_3$ |
| CH$_3$ | CH$_3$ | 4-OC$_2$F$_5$ |
| CH$_3$ | CH$_3$ | 4-OCF$_2$CHF$_2$ |
| CH$_3$ | CH$_3$ | 3-CH$_2$OCH$_3$ |
| CH$_3$ | CH$_3$ | 4-CH$_2$OCH$_3$ |
| CH$_3$ | CH$_3$ | 4-CH$_2$—O-t-C$_4$H$_9$ |
| CH$_3$ | CH$_3$ | 4-CH(OCH$_3$)$_2$ |
| CH$_3$ | CH$_3$ | 4-CH$_2$CN |
| CH$_3$ | CH$_3$ | 3-CHO |
| CH$_3$ | CH$_3$ | 4-CHO |
| CH$_3$ | CH$_3$ | 3-CO—CH$_3$ |
| CH$_3$ | CH$_3$ | 4-CO—CH$_3$ |
| CH$_3$ | CH$_3$ | 3-COOH |
| CH$_3$ | CH$_3$ | 4-COOH |
| CH$_3$ | CH$_3$ | 3-COOCH$_3$ |
| CH$_3$ | CH$_3$ | 4-COOCH$_3$ |
| CH$_3$ | CH$_3$ | 3-COOC$_2$H$_5$ |
| CH$_3$ | CH$_3$ | 4-COOC$_2$H$_5$ |
| CH$_3$ | CH$_3$ | 3-COO-i-C$_3$H$_7$ |
| CH$_3$ | CH$_3$ | 4-COO-i-C$_3$H$_7$ |
| CH$_3$ | CH$_3$ | 3-COO-t-C$_4$H$_9$ |
| CH$_3$ | CH$_3$ | 4-COO-t-C$_4$H$_9$ |
| CH$_3$ | CH$_3$ | 3-COO-n-C$_6$H$_{13}$ |
| CH$_3$ | CH$_3$ | 4-COO-n-C$_6$H$_{13}$ |
| CH$_3$ | CH$_3$ | 3-CONH$_2$ |
| CH$_3$ | CH$_3$ | 4-CONH$_2$ |
| CH$_3$ | CH$_3$ | 3-CONHCH$_3$ |
| CH$_3$ | CH$_3$ | 4-CONHCH$_3$ |
| CH$_3$ | CH$_3$ | 3-CON(CH$_3$)$_2$ |
| CH$_3$ | CH$_3$ | 4-CON(CH$_3$)$_2$ |
| CH$_3$ | CH$_3$ | 3-CSNH$_2$ |
| CH$_3$ | CH$_3$ | 4-CSNH$_2$ |
| CH$_3$ | CH$_3$ | 3-NH$_2$ |
| CH$_3$ | CH$_3$ | 4-NH$_2$ |
| CH$_3$ | CH$_3$ | 4-NHCH$_3$ |
| CH$_3$ | CH$_3$ | 4-N(CH$_3$)$_2$ |
| CH$_3$ | CH$_3$ | 3-NHCO—CH$_3$ |
| CH$_3$ | CH$_3$ | 4-NHCO—CH$_3$ |
| CH$_3$ | CH$_3$ | 4-NCH$_3$—CO—CH$_3$ |
| CH$_3$ | CH$_3$ | 4-NHCOOCH$_3$ |
| CH$_3$ | CH$_3$ | 4-NCH$_3$—COOCH$_3$ |
| CH$_3$ | CH$_3$ | 3-OCO—CH$_3$ |
| CH$_3$ | CH$_3$ | 4-OCO—CH$_3$ |
| CH$_3$ | CH$_3$ | 4-OCO-t-C$_4$H$_9$ |
| CH$_3$ | CH$_3$ | 4-SH |
| CH$_3$ | CH$_3$ | 4-SCH$_3$ |
| CH$_3$ | CH$_3$ | 4-S-t-C$_4$H$_9$ |
| CH$_3$ | CH$_3$ | 4-SO—CH$_3$ |
| CH$_3$ | CH$_3$ | 4-SO$_2$—CH$_3$ |
| CH$_3$ | CH$_3$ | 4-C(CH$_3$)=NCH$_3$ |
| CH$_3$ | CH$_3$ | 4-C(SCH$_3$)=NOCH$_3$ |
| CH$_3$ | CH$_3$ | 4-C(OCH$_3$)=NOCH$_3$ |
| CH$_3$ | CH$_3$ | 3-CH=NOCH$_3$ |
| CH$_3$ | CH$_3$ | 4-CH=NOCH$_3$ |
| CH$_3$ | CH$_3$ | 3-C(CH$_3$)=NOCH$_3$ |
| CH$_3$ | CH$_3$ | 4-C(CH$_3$)=NOCH$_3$ |
| CH$_3$ | CH$_3$ | 4-C(CH$_3$)=NOC$_2$H$_5$ |
| CH$_3$ | CH$_3$ | 4-C(CH$_3$)=NO-n-C$_3$H$_7$ |
| CH$_3$ | CH$_3$ | 4-C(CH$_3$)=NO-i-C$_3$H$_7$ |
| CH$_3$ | CH$_3$ | 4-C(CH$_3$)=NO-n-C$_4$H$_9$ |
| CH$_3$ | CH$_3$ | 4-C(CH$_3$)=NO-t-C$_4$H$_9$ |
| CH$_3$ | CH$_3$ | 4-C(CH$_3$)=NO-n-C$_5$H$_{11}$ |
| CH$_3$ | CH$_3$ | 4-C(CH$_3$)=NO-n-C$_6$H$_{13}$ |
| CH$_3$ | CH$_3$ | 2-Cl, 4-CH$_3$ |
| CH$_3$ | CH$_3$ | 3-Cl, 5-CH$_3$ |
| CH$_3$ | CH$_3$ | 2-CH$_3$, 4-Cl |
| CH$_3$ | CH$_3$ | 3-CH$_3$, 4-Cl |
| CH$_3$ | CH$_3$ | 3-F, 5-CH$_3$ |
| CH$_3$ | CH$_3$ | 3-Br, 5-CH$_3$ |
| CH$_3$ | CH$_3$ | 3-Cl, 5-NO$_2$ |
| CH$_3$ | CH$_3$ | 3-NO$_2$, 4-Cl |
| CH$_3$ | CH$_3$ | 3-Cl, 4-OCH$_3$ |
| CH$_3$ | CH$_3$ | 3-OCH$_3$, 4-Cl |
| CH$_3$ | CH$_3$ | 3-Cl, 5-CF$_3$ |
| CH$_3$ | CH$_3$ | 3-Cl, 5-OCF$_3$ |
| CH$_3$ | CH$_3$ | 3-F, 5-CF$_3$ |
| CH$_3$ | CH$_3$ | 2-CH$_3$, 4-CN |
| CH$_3$ | CH$_3$ | 2-CH$_3$, 4-OCH$_3$ |
| CH$_3$ | CH$_3$ | 2-CH$_3$, 4-CF$_3$ |
| CH$_3$ | CH$_3$ | 2-CH$_3$, 4-C(CH$_3$)=NOCH$_3$ |
| CH$_3$ | CH$_3$ | 3-CH$_3$, 4-C(CH$_3$)=NOCH$_3$ |
| CH$_3$ | CH$_3$ | 2-OH, 5-CH$_3$ |
| CH$_3$ | CH$_3$ | 3-CH$_3$, 4-O-t-C$_4$H$_9$ |
| CH$_3$ | CH$_3$ | 2-C(COOCH$_3$)=NOCH$_3$ |
| CH$_3$ | CH$_3$ | 2,3-Butadienyl |
| CH$_3$ | CH$_3$ | 3,4-Butadienyl |
| H | Cyclopropyl | H |
| H | Cyclopropyl | 2-F |
| H | Cyclopropyl | 3-F |
| H | Cyclopropyl | 4-F |
| H | Cyclopropyl | 2,3-F$_2$ |
| H | Cyclopropyl | 2,4-F$_2$ |
| H | Cyclopropyl | 2,5-F$_2$ |
| H | Cyclopropyl | 2,6-F$_2$ |
| H | Cyclopropyl | 3,4-F$_2$ |
| H | Cyclopropyl | 3,5-F$_2$ |
| H | Cyclopropyl | 2-Cl |
| H | Cyclopropyl | 3-Cl |
| H | Cyclopropyl | 4-Cl |
| H | Cyclopropyl | 2,4-Cl$_2$ |
| H | Cyclopropyl | 2,5-Cl$_2$ |
| H | Cyclopropyl | 3,4-Cl$_2$ |
| H | Cyclopropyl | 3,5-Cl$_2$ |
| H | Cyclopropyl | 2-Br |
| H | Cyclopropyl | 3-Br |
| H | Cyclopropyl | 4-Br |
| H | Cyclopropyl | 2,4-Br$_2$ |
| H | Cyclopropyl | 3,4-Br$_2$ |

TABLE A-continued

| R | A | Q_m |
|---|---|---|
| H | Cyclopropyl | 3,5-Br$_2$ |
| H | Cyclopropyl | 2-I |
| H | Cyclopropyl | 3-I |
| H | Cyclopropyl | 4-I |
| H | Cyclopropyl | 2-F, 4-Cl |
| H | Cyclopropyl | 2-F, 5-Cl |
| H | Cyclopropyl | 2-F, 4-Br |
| H | Cyclopropyl | 2-F, 5-Br |
| H | Cyclopropyl | 2-Cl, 4-Br |
| H | Cyclopropyl | 2-Cl, 5-Br |
| H | Cyclopropyl | 3-F, 4-Cl |
| H | Cyclopropyl | 3-F, 5-Cl |
| H | Cyclopropyl | 3-F, 4-Br |
| H | Cyclopropyl | 3-F, 5-Br |
| H | Cyclopropyl | 3-Cl, 4-Br |
| H | Cyclopropyl | 3-Cl, 5-Br |
| H | Cyclopropyl | 3-Cl, 4-F |
| H | Cyclopropyl | 3-Br, 4-F |
| H | Cyclopropyl | 3-Br, 4-Cl |
| H | Cyclopropyl | 2-NO$_2$ |
| H | Cyclopropyl | 3-NO$_2$ |
| H | Cyclopropyl | 4-NO$_2$ |
| H | Cyclopropyl | 2-CN |
| H | Cyclopropyl | 3-CN |
| H | Cyclopropyl | 4-CN |
| H | Cyclopropyl | 2-CH$_3$ |
| H | Cyclopropyl | 3-CH$_3$ |
| H | Cyclopropyl | 4-CH$_3$ |
| H | Cyclopropyl | 2,3-(CH$_3$)$_2$ |
| H | Cyclopropyl | 2,4-(CH$_3$)$_2$ |
| H | Cyclopropyl | 2,5-(CH$_3$)$_2$ |
| H | Cyclopropyl | 2,6-(CH$_3$)$_2$ |
| H | Cyclopropyl | 3,4-(CH$_3$)$_2$ |
| H | Cyclopropyl | 3,5-(CH$_3$)$_2$ |
| H | Cyclopropyl | 2,4,5-(CH$_3$)$_3$ |
| H | Cyclopropyl | 2,4,6-(CH$_3$)$_3$ |
| H | Cyclopropyl | 3,4,5-(CH$_3$)$_3$ |
| H | Cyclopropyl | 2-C$_2$H$_5$ |
| H | Cyclopropyl | 3-C$_2$H$_5$ |
| H | Cyclopropyl | 4-C$_2$H$_5$ |
| H | Cyclopropyl | 3,4-(C$_2$H$_5$)$_2$ |
| H | Cyclopropyl | 3,5-(C$_2$H$_5$)$_2$ |
| H | Cyclopropyl | 3-n-C$_3$H$_7$ |
| H | Cyclopropyl | 4-n-C$_3$H$_7$ |
| H | Cyclopropyl | 3,4-(n-C$_3$H$_7$)$_2$ |
| H | Cyclopropyl | 3,5-(n-C$_3$H$_7$)$_2$ |
| H | Cyclopropyl | 3-i-C$_3$H$_7$ |
| H | Cyclopropyl | 4-i-C$_3$H$_7$ |
| H | Cyclopropyl | 3,4-(i-C$_3$H$_7$)$_2$ |
| H | Cyclopropyl | 3,5-(i-C$_3$H$_7$)$_2$ |
| H | Cyclopropyl | 3-Cyclopropyl |
| H | Cyclopropyl | 4-Cyclopropyl |
| H | Cyclopropyl | 3-n-C$_4$H$_9$ |
| H | Cyclopropyl | 4-n-C$_4$H$_9$ |
| H | Cyclopropyl | 3,4-(n-C$_4$H$_9$)$_2$ |
| H | Cyclopropyl | 3,5-(n-C$_4$H$_9$)$_2$ |
| H | Cyclopropyl | 3-s-C$_4$H$_9$ |
| H | Cyclopropyl | 4-s-C$_4$H$_9$ |
| H | Cyclopropyl | 3-i-C$_4$H$_9$ |
| H | Cyclopropyl | 4-i-C$_4$H$_9$ |
| H | Cyclopropyl | 3-t-C$_4$H$_9$ |
| H | Cyclopropyl | 4-t-C$_4$H$_9$ |
| H | Cyclopropyl | 3,4-(t-C$_4$H$_9$)$_2$ |
| H | Cyclopropyl | 3,5-(t-C$_4$H$_9$)$_2$ |
| H | Cyclopropyl | 3-n-C$_5$H$_{11}$ |
| H | Cyclopropyl | 4-n-C$_5$H$_{11}$ |
| H | Cyclopropyl | 3-n-C$_6$H$_{13}$ |
| H | Cyclopropyl | 4-n-C$_6$H$_{13}$ |
| H | Cyclopropyl | 3-Cyclohexyl |
| H | Cyclopropyl | 4-Cyclohexyl |
| H | Cyclopropyl | 3-Phenyl |
| H | Cyclopropyl | 4-Phenyl |
| H | Cyclopropyl | 3-Vinyl |
| H | Cyclopropyl | 4-Vinyl |
| H | Cyclopropyl | 3-Allyl |
| H | Cyclopropyl | 4-Allyl |
| H | Cyclopropyl | 3-Propargyl |
| H | Cyclopropyl | 4-Propargyl |
| H | Cyclopropyl | 3-(Propen-2-yl) |
| H | Cyclopropyl | 4-(Propen-2-yl) |
| H | Cyclopropyl | 2-CH$_3$, 4-C$_2$H$_5$ |
| H | Cyclopropyl | 2-CH$_3$, 5-C$_2$H$_5$ |
| H | Cyclopropyl | 2-CH$_3$—, 4-n-C$_3$H$_7$ |
| H | Cyclopropyl | 2-CH$_3$, 5-n-C$_3$H$_7$ |
| H | Cyclopropyl | 2-CH$_3$, 4-i-C$_3$H$_7$ |
| H | Cyclopropyl | 2-CH$_3$, 5-i-C$_3$H$_7$ |
| H | Cyclopropyl | 2-CH$_3$, 4-n-C$_4$H$_9$ |
| H | Cyclopropyl | 2-CH$_3$, 4-s-C$_4$H$_9$ |
| H | Cyclopropyl | 2-CH$_3$, 4-i-C$_4$H$_9$ |
| H | Cyclopropyl | 2-CH$_3$, 4-t-C$_4$H$_9$ |
| H | Cyclopropyl | 2-CH$_3$, 4-phenyl |
| H | Cyclopropyl | 2-CH$_3$, 5-phenyl |
| H | Cyclopropyl | 2-CH$_3$, 4-vinyl |
| H | Cyclopropyl | 2-CH$_3$, 4-allyl |
| H | Cyclopropyl | 2-CH$_3$, 4-propargyl |
| H | Cyclopropyl | 2-CH$_3$, 4-(propen-2-yl) |
| H | Cyclopropyl | 3-CH$_3$, 4-C$_2$H$_5$ |
| H | Cyclopropyl | 3-CH$_3$, 5-C$_2$H$_5$ |
| H | Cyclopropyl | 3-CH$_3$, 4-n-C$_3$H$_7$ |
| H | Cyclopropyl | 3-CH$_3$, 5-n-C$_3$H$_7$ |
| H | Cyclopropyl | 3-CH$_3$, 4-i-C$_3$H$_7$ |
| H | Cyclopropyl | 3-CH$_3$, 5-i-C$_3$H$_7$ |
| H | Cyclopropyl | 3-CH$_3$, 4-cyclopropyl |
| H | Cyclopropyl | 3-CH$_3$, 4-t-C$_4$H$_9$ |
| H | Cyclopropyl | 3-CH$_3$, 5-t-C$_4$H$_9$ |
| H | Cyclopropyl | 3-CH$_3$, 4-phenyl |
| H | Cyclopropyl | 3-CH$_3$, 5-Phenyl |
| H | Cyclopropyl | 3-CH$_3$, 4-vinyl |
| H | Cyclopropyl | 3-CH$_3$, 4-allyl |
| H | Cyclopropyl | 3-CH$_3$, 4-propargyl |
| H | Cyclopropyl | 3-CH$_3$, 4-propen-2-yl |
| H | Cyclopropyl | 3-C$_2$H$_5$, 4-CH$_3$ |
| H | Cyclopropyl | 3-i-C$_3$H$_7$, 4-CH$_3$ |
| H | Cyclopropyl | 3-t-C$_4$H$_9$, 4-CH$_3$ |
| H | Cyclopropyl | 3-Phenyl, 4-CH$_3$ |
| H | Cyclopropyl | 2-OH |
| H | Cyclopropyl | 3-OH |
| H | Cyclopropyl | 4-OH |
| H | Cyclopropyl | 2-OCH$_3$ |
| H | Cyclopropyl | 3-OCH$_3$ |
| H | Cyclopropyl | 4-OCH$_3$ |
| H | Cyclopropyl | 2,3-(OCH$_3$)$_2$ |
| H | Cyclopropyl | 2,4-(OCH$_3$)$_2$ |
| H | Cyclopropyl | 2,5-(OCH$_3$)$_2$ |
| H | Cyclopropyl | 3,4-(OCH$_3$)$_2$ |
| H | Cyclopropyl | 3,5-(OCH$_3$)$_2$ |
| H | Cyclopropyl | 3,4,5-(OCH$_3$)$_3$ |
| H | Cyclopropyl | 3-OC$_2$H$_5$ |
| H | Cyclopropyl | 4-OC$_2$H$_5$ |
| H | Cyclopropyl | 3,4-(OC$_2$H$_5$)$_2$ |
| H | Cyclopropyl | 3,5-(OC$_2$H$_5$)$_2$ |
| H | Cyclopropyl | 3-O-n-C$_3$H$_7$ |
| H | Cyclopropyl | 4-O-n-C$_3$H$_7$ |
| H | Cyclopropyl | 3-O-i-C$_3$H$_7$ |
| H | Cyclopropyl | 4-O-i-C$_3$H$_7$ |
| H | Cyclopropyl | 3-O-Cyclopropyl |
| H | Cyclopropyl | 4-O-Cyclopropyl |
| H | Cyclopropyl | 3-O-n-C$_4$H$_9$ |
| H | Cyclopropyl | 4-O-n-C$_4$H$_9$ |
| H | Cyclopropyl | 3-O-s-C$_4$H$_9$ |
| H | Cyclopropyl | 4-O-s-C$_4$H$_9$ |
| H | Cyclopropyl | 3-O-i-C$_4$H$_9$ |
| H | Cyclopropyl | 4-O-i-C$_4$H$_9$ |
| H | Cyclopropyl | 3-O-t-C$_4$H$_9$ |
| H | Cyclopropyl | 4-O-t-C$_4$H$_9$ |
| H | Cyclopropyl | 3-O-n-C$_5$H$_{11}$ |
| H | Cyclopropyl | 4-O-n-C$_5$H$_{11}$ |
| H | Cyclopropyl | 3-O-n-C$_6$H$_{13}$ |
| H | Cyclopropyl | 4-O-n-C$_6$H$_{13}$ |
| H | Cyclopropyl | 3-O-Cyclohexyl |
| H | Cyclopropyl | 4-O-Cyclohexyl |
| H | Cyclopropyl | 3-O-Phenyl |
| H | Cyclopropyl | 4-O-Phenyl |
| H | Cyclopropyl | 3-O-Allyl |

TABLE A-continued

| R | A | Q_m |
|---|---|---|
| H | Cyclopropyl | 4-O-Allyl |
| H | Cyclopropyl | 2-CF$_3$ |
| H | Cyclopropyl | 3-CF$_3$ |
| H | Cyclopropyl | 4-CF$_3$ |
| H | Cyclopropyl | 2,4-(CF$_3$)$_2$ |
| H | Cyclopropyl | 3,5-(CF$_3$)$_2$ |
| H | Cyclopropyl | 3-CF$_2$Cl |
| H | Cyclopropyl | 4-CF$_2$Cl |
| H | Cyclopropyl | 3-CFCl$_2$ |
| H | Cyclopropyl | 4-CFCl$_2$ |
| H | Cyclopropyl | 3-CCl$_3$ |
| H | Cyclopropyl | 4-CCl$_3$ |
| H | Cyclopropyl | 3-CH$_2$CH$_2$F |
| H | Cyclopropyl | 4-CH$_2$CH$_2$F |
| H | Cyclopropyl | 3-CH$_2$CF$_3$ |
| H | Cyclopropyl | 4-CH$_2$CF$_3$ |
| H | Cyclopropyl | 3-C$_2$F$_5$ |
| H | Cyclopropyl | 4-C$_2$F$_5$ |
| H | Cyclopropyl | 3-CHCl$_2$ |
| H | Cyclopropyl | 4-CHCl$_2$ |
| H | Cyclopropyl | 3-CH$_2$Cl |
| H | Cyclopropyl | 4-CH$_2$Cl |
| H | Cyclopropyl | 3-CF$_2$CHF$_2$ |
| H | Cyclopropyl | 4-CF$_2$CHF$_2$ |
| H | Cyclopropyl | 3-CH$_2$CH$_2$Cl |
| H | Cyclopropyl | 4-CH$_2$CH$_2$Cl |
| H | Cyclopropyl | 2-OCF$_3$ |
| H | Cyclopropyl | 3-OCF$_3$ |
| H | Cyclopropyl | 4-OCF$_3$ |
| H | Cyclopropyl | 3-OCHF$_2$ |
| H | Cyclopropyl | 4-OCHF$_2$ |
| H | Cyclopropyl | 3-OC$_2$F$_5$ |
| H | Cyclopropyl | 4-OC$_2$F$_5$ |
| H | Cyclopropyl | 3-OCF$_2$CHF$_2$ |
| H | Cyclopropyl | 4-OCF$_2$CHF$_2$ |
| H | Cyclopropyl | 3-CH$_2$OCH$_3$ |
| H | Cyclopropyl | 4-CH$_2$OCH$_3$ |
| H | Cyclopropyl | 3-CH$_2$O-t-C$_4$H$_9$ |
| H | Cyclopropyl | 4-CH$_2$O-t-C$_4$H$_9$ |
| H | Cyclopropyl | 3-C(CH$_3$)(OCH$_3$)$_2$ |
| H | Cyclopropyl | 4-C(CH$_3$)(OCH$_3$)$_2$ |
| H | Cyclopropyl | 3-CH(OCH$_3$)$_2$ |
| H | Cyclopropyl | 4-CH(OCH$_3$)$_2$ |
| H | Cyclopropyl | 3-CH$_2$CN |
| H | Cyclopropyl | 4-CH$_2$CN |
| H | Cyclopropyl | 3-CHO |
| H | Cyclopropyl | 4-CHO |
| H | Cyclopropyl | 3-CO—CH$_3$ |
| H | Cyclopropyl | 4-CO—CH$_3$ |
| H | Cyclopropyl | 3-CO—C$_2$H$_5$ |
| H | Cyclopropyl | 4-CO—C$_2$H$_5$ |
| H | Cyclopropyl | 2-COOH |
| H | Cyclopropyl | 3-COOH |
| H | Cyclopropyl | 4-COOH |
| H | Cyclopropyl | 3-COOCH$_3$ |
| H | Cyclopropyl | 4-COOCH$_3$ |
| H | Cyclopropyl | 3-COOC$_2$H$_5$ |
| H | Cyclopropyl | 4-COOC$_2$H$_5$ |
| H | Cyclopropyl | 3-COO-n-C$_3$H$_7$ |
| H | Cyclopropyl | 4-COO-n-C$_3$H$_7$ |
| H | Cyclopropyl | 3-COO-i-C$_3$H$_7$ |
| H | Cyclopropyl | 4-COO-i-C$_3$H$_7$ |
| H | Cyclopropyl | 3-COO-n-C$_4$H$_9$ |
| H | Cyclopropyl | 4-COO-n-C$_4$H$_9$ |
| H | Cyclopropyl | 3-COO-s-C$_4$H$_9$ |
| H | Cyclopropyl | 4-COO-s-C$_4$H$_9$ |
| H | Cyclopropyl | 3-COO-i-C$_4$H$_9$ |
| H | Cyclopropyl | 4-COO-i-C$_4$H$_9$ |
| H | Cyclopropyl | 3-COO-t-C$_4$H$_9$ |
| H | Cyclopropyl | 4-COO-t-C$_4$H$_9$ |
| H | Cyclopropyl | 3-COO-n-C$_5$H$_{11}$ |
| H | Cyclopropyl | 4-COO-n-C$_5$H$_{11}$ |
| H | Cyclopropyl | 3-COO-n-C$_6$H$_{13}$ |
| H | Cyclopropyl | 4-COO-n-C$_6$H$_{13}$ |
| H | Cyclopropyl | 2-CONH$_2$ |
| H | Cyclopropyl | 3-CONH$_2$ |
| H | Cyclopropyl | 4-CONH$_2$ |
| H | Cyclopropyl | 3-CONHCH$_3$ |
| H | Cyclopropyl | 4-CONHCH$_3$ |
| H | Cyclopropyl | 3-CON(CH$_3$)$_2$ |
| H | Cyclopropyl | 4-CON(CH$_3$)$_2$ |
| H | Cyclopropyl | 3-CON(C$_2$H$_5$)$_2$ |
| H | Cyclopropyl | 4-CON(C$_2$H$_5$)$_2$ |
| H | Cyclopropyl | 2-CSNH$_2$ |
| H | Cyclopropyl | 3-CSNH$_2$ |
| H | Cyclopropyl | 4-CSNH$_2$ |
| H | Cyclopropyl | 2-NH$_2$ |
| H | Cyclopropyl | 3-NH$_2$ |
| H | Cyclopropyl | 4-NH$_2$ |
| H | Cyclopropyl | 3-NHCH$_3$ |
| H | Cyclopropyl | 4-NHCH$_3$ |
| H | Cyclopropyl | 3-N(CH$_3$)$_2$ |
| H | Cyclopropyl | 4-N(CH$_3$)$_2$ |
| H | Cyclopropyl | 3-NHCO—CH$_3$ |
| H | Cyclopropyl | 4-NHCO—CH$_3$ |
| H | Cyclopropyl | 3-NCH$_3$—CO—CH$_3$ |
| H | Cyclopropyl | 4-NCH$_3$—CO—CH$_3$ |
| H | Cyclopropyl | 3-NHCOOCH$_3$ |
| H | Cyclopropyl | 4-NHCOOCH$_3$ |
| H | Cyclopropyl | 3-NCH$_3$—COOCH$_3$ |
| H | Cyclopropyl | 4-NCH$_3$—COOCH$_3$ |
| H | Cyclopropyl | 3-OCO—CH$_3$ |
| H | Cyclopropyl | 4-OCO—CH$_3$ |
| H | Cyclopropyl | 3-OCO-t-C$_4$H$_9$ |
| H | Cyclopropyl | 4-OCO-t-C$_4$H$_9$ |
| H | Cyclopropyl | 3-SH |
| H | Cyclopropyl | 4-SH |
| H | Cyclopropyl | 3-SCH$_3$ |
| H | Cyclopropyl | 4-SCH$_3$ |
| H | Cyclopropyl | 3-S-t-C$_4$H$_9$ |
| H | Cyclopropyl | 4-S-t-C$_4$H$_9$ |
| H | Cyclopropyl | 3-SO—CH$_3$ |
| H | Cyclopropyl | 4-SO—CH$_3$ |
| H | Cyclopropyl | 3-SO$_2$CH$_3$ |
| H | Cyclopropyl | 4-SO$_2$CH$_3$ |
| H | Cyclopropyl | 3-CH=NCH$_3$ |
| H | Cyclopropyl | 4-CH=NCH$_3$ |
| H | Cyclopropyl | 3-C(CH$_3$)=NCH$_3$ |
| H | Cyclopropyl | 4-C(CH$_3$)=NCH$_3$ |
| H | Cyclopropyl | 3-C(SCH$_3$)=NOCH$_3$ |
| H | Cyclopropyl | 4-C(SCH$_3$)=NOCH$_3$ |
| H | Cyclopropyl | 3-C(OCH$_3$)=NOCH$_3$ |
| H | Cyclopropyl | 4-C(OCH$_3$)=NOCH$_3$ |
| H | Cyclopropyl | 3-C(NH$_2$)=NOCH$_3$ |
| H | Cyclopropyl | 4-C(NH$_2$)=NOCH$_3$ |
| H | Cyclopropyl | 3-C(NHCH$_3$)=NOCH$_3$ |
| H | Cyclopropyl | 4-C(NHCH$_3$)=NOCH$_3$ |
| H | Cyclopropyl | 3-CH=NOCH$_3$ |
| H | Cyclopropyl | 4-CH=NOCH$_3$ |
| H | Cyclopropyl | 3-C(CH$_3$)=NOCH$_3$ |
| H | Cyclopropyl | 4-C(CH$_3$)=NOCH$_3$ |
| H | Cyclopropyl | 3-C(CH$_3$)=NOC$_2$H$_5$ |
| H | Cyclopropyl | 4-C(CH$_3$)=NOC$_2$H$_5$ |
| H | Cyclopropyl | 3-C(CH$_3$)=NO-n-C$_3$H$_7$ |
| H | Cyclopropyl | 4-C(CH$_3$)=NO-n-C$_3$H$_7$ |
| H | Cyclopropyl | 3-C(CH$_3$)=NO-i-C$_3$H$_7$ |
| H | Cyclopropyl | 4-C(CH$_3$)=NO-i-C$_3$H$_7$ |
| H | Cyclopropyl | 3-C(CH$_3$)=NO-n-C$_4$H$_9$ |
| H | Cyclopropyl | 4-C(CH$_3$)=NO-n-C$_4$H$_9$ |
| H | Cyclopropyl | 3-C(CH$_3$)=NO-s-C$_4$H$_9$ |
| H | Cyclopropyl | 4-C(CH$_3$)=NO-s-C$_4$H$_9$ |
| H | Cyclopropyl | 3-C(CH$_3$)=NO-i-C$_4$H$_9$ |
| H | Cyclopropyl | 4-C(CH$_3$)=NO-i-C$_4$H$_9$ |
| H | Cyclopropyl | 3-C(CH$_3$)=NO-t-C$_4$H$_9$ |
| H | Cyclopropyl | 4-C(CH$_3$)=NO-t-C$_4$H$_9$ |
| H | Cyclopropyl | 3-C(CH$_3$)=NO-n-C$_5$H$_{11}$ |
| H | Cyclopropyl | 4-C(CH$_3$)=NO-n-C$_5$H$_{11}$ |
| H | Cyclopropyl | 3-C(CH$_3$)=NO-n-C$_6$H$_{13}$ |
| H | Cyclopropyl | 4-C(CH$_3$)=NO-n-C$_6$H$_{13}$ |
| H | Cyclopropyl | 2-Cl, 4-CH$_3$ |
| H | Cyclopropyl | 2-Cl, 5-CH$_3$ |
| H | Cyclopropyl | 3-Cl, 4-CH$_3$ |
| H | Cyclopropyl | 3-Cl, 5-CH$_3$ |
| H | Cyclopropyl | 2-CH$_3$, 4-Cl |

TABLE A-continued

| R | A | Q_m |
|---|---|---|
| H | Cyclopropyl | 2-CH$_3$, 5-Cl |
| H | Cyclopropyl | 3-CH$_3$, 4-Cl |
| H | Cyclopropyl | 3-Cl, 5-t-C$_4$H$_9$ |
| H | Cyclopropyl | 2-Cl, 4-t-C$_4$H$_9$ |
| H | Cyclopropyl | 2-F, 4-CH$_3$ |
| H | Cyclopropyl | 3-F, 4-CH$_3$ |
| H | Cyclopropyl | 3-F, 5-CH$_3$ |
| H | Cyclopropyl | 2-CH$_3$, 4-F |
| H | Cyclopropyl | 3-CH$_3$, 4-F |
| H | Cyclopropyl | 2-F, 4-t-C$_4$H$_9$ |
| H | Cyclopropyl | 3-F, 4-t-C$_4$H$_9$ |
| H | Cyclopropyl | 2-F, 4-OCH$_3$ |
| H | Cyclopropyl | 2-Br, 4-CH$_3$ |
| H | Cyclopropyl | 3-Br, 4-CH$_3$ |
| H | Cyclopropyl | 3-Br, 5-CH$_3$ |
| H | Cyclopropyl | 2-CH$_3$, 4-Br |
| H | Cyclopropyl | 3-CH$_3$, 4-Br |
| H | Cyclopropyl | 2-Br, 4-t-C$_4$H$_9$ |
| H | Cyclopropyl | 2-Cl, 4-NO$_2$ |
| H | Cyclopropyl | 3-Cl, 4-NO$_2$ |
| H | Cyclopropyl | 3-Cl, 5-NO$_2$ |
| H | Cyclopropyl | 3-NO$_2$, 4-Cl |
| H | Cyclopropyl | 3-Cl, 4-OCH$_3$ |
| H | Cyclopropyl | 3-OCH$_3$, 4-Cl |
| H | Cyclopropyl | 2-Cl, 5-CF$_3$ |
| H | Cyclopropyl | 3-Cl, 4-CF$_3$ |
| H | Cyclopropyl | 3-Cl, 5-CF$_3$ |
| H | Cyclopropyl | 3-CF$_3$, 4-Cl |
| H | Cyclopropyl | 3-Cl, 5-OCF$_3$ |
| H | Cyclopropyl | 3-F, 5-CF$_3$ |
| H | Cyclopropyl | 2-CH$_3$, 4-CN |
| H | Cyclopropyl | 3-NO$_2$, 4-CH$_3$ |
| H | Cyclopropyl | 2-CH$_3$, 4-OCH$_3$ |
| H | Cyclopropyl | 3-CH$_3$, 4-OCH$_3$ |
| H | Cyclopropyl | 3-CH$_3$, 5-OCH$_3$ |
| H | Cyclopropyl | 3-OCH$_3$, 4-CH$_3$ |
| H | Cyclopropyl | 2-CH$_3$, 4-O-i-C$_3$H$_7$ |
| H | Cyclopropyl | 3-CH$_3$, 4-O-i-C$_3$H$_7$ |
| H | Cyclopropyl | 3-O-i-C$_3$H$_7$, 4-CH$_3$ |
| H | Cyclopropyl | 2-CH$_3$, 4-CF$_3$ |
| H | Cyclopropyl | 2-CH$_3$, 5-CF$_3$ |
| H | Cyclopropyl | 3-CH$_3$, 4-CF$_3$ |
| H | Cyclopropyl | 3-CH$_3$, 5-CF$_3$ |
| H | Cyclopropyl | 3-CF$_3$, 4-CH$_3$ |
| H | Cyclopropyl | 3-CF$_3$, 4-OCH$_3$ |
| H | Cyclopropyl | 3-OCH$_3$, 4-CF$_3$ |
| H | Cyclopropyl | 2-CH$_3$, 4-C(CH$_3$)=NOCH$_3$ |
| H | Cyclopropyl | 3-CH$_3$, 4-C(CH$_3$)=NOCH$_3$ |
| H | Cyclopropyl | 2-OH, 5-CH$_3$ |
| H | Cyclopropyl | 3-CH$_3$, 4-OC$_2$H$_5$ |
| H | Cyclopropyl | 3-CH$_3$, 4-O-t-C$_4$H$_9$ |
| H | Cyclopropyl | 3-OC$_2$H$_5$, 4-CH$_3$ |
| H | Cyclopropyl | 3-O-t-C$_4$H$_9$, 4-CH$_3$ |
| H | Cyclopropyl | 2-C(COOCH$_3$)=NOCH$_3$ |
| H | Cyclopropyl | 2,3-Butadienyl |
| H | Cyclopropyl | 3,4-Butadienyl |
| CH$_3$ | Cyclopropyl | H |
| CH$_3$ | Cyclopropyl | 2-F |
| CH$_3$ | Cyclopropyl | 3-F |
| CH$_3$ | Cyclopropyl | 4-F |
| CH$_3$ | Cyclopropyl | 2,4-F$_2$ |
| CH$_3$ | Cyclopropyl | 3,4-F$_2$ |
| CH$_3$ | Cyclopropyl | 3,5-F$_2$ |
| CH$_3$ | Cyclopropyl | 2-Cl |
| CH$_3$ | Cyclopropyl | 3-Cl |
| CH$_3$ | Cyclopropyl | 4-Cl |
| CH$_3$ | Cyclopropyl | 2,4-Cl$_2$ |
| CH$_3$ | Cyclopropyl | 3,4-Cl$_2$ |
| CH$_3$ | Cyclopropyl | 3,5-Cl$_2$ |
| CH$_3$ | Cyclopropyl | 2-Br |
| CH$_3$ | Cyclopropyl | 3-Br |
| CH$_3$ | Cyclopropyl | 4-Br |
| CH$_3$ | Cyclopropyl | 3,5-Br$_2$ |
| CH$_3$ | Cyclopropyl | 3-I |
| CH$_3$ | Cyclopropyl | 4-I |
| CH$_3$ | Cyclopropyl | 3-F, 5-Cl |
| CH$_3$ | Cyclopropyl | 3-F, 5-Br |
| CH$_3$ | Cyclopropyl | 3-Cl, 5-Br |
| CH$_3$ | Cyclopropyl | 3-Br, 4-F |
| CH$_3$ | Cyclopropyl | 2-NO$_2$ |
| CH$_3$ | Cyclopropyl | 3-NO$_2$ |
| CH$_3$ | Cyclopropyl | 4-NO$_2$ |
| CH$_3$ | Cyclopropyl | 2-CN |
| CH$_3$ | Cyclopropyl | 3-CN |
| CH$_3$ | Cyclopropyl | 4-CN |
| CH$_3$ | Cyclopropyl | 2-CH$_3$ |
| CH$_3$ | Cyclopropyl | 3-CH$_3$ |
| CH$_3$ | Cyclopropyl | 4-CH$_3$ |
| CH$_3$ | Cyclopropyl | 2,4-(CH$_3$)$_2$ |
| CH$_3$ | Cyclopropyl | 2,5-(CH$_3$)$_2$ |
| CH$_3$ | Cyclopropyl | 3,4-(CH$_3$)$_2$ |
| CH$_3$ | Cyclopropyl | 3,5-(CH$_3$)$_2$ |
| CH$_3$ | Cyclopropyl | 2,4,5-(CH$_3$)$_3$ |
| CH$_3$ | Cyclopropyl | 2,4,6-(CH$_3$)$_3$ |
| CH$_3$ | Cyclopropyl | 3-C$_2$H$_5$ |
| CH$_3$ | Cyclopropyl | 4-C$_2$H$_5$ |
| CH$_3$ | Cyclopropyl | 3,4-(C$_2$H$_5$)$_2$ |
| CH$_3$ | Cyclopropyl | 3,5-(C$_2$H$_5$)$_2$ |
| CH$_3$ | Cyclopropyl | 3-n-C$_3$H$_7$ |
| CH$_3$ | Cyclopropyl | 4-n-C$_3$H$_7$ |
| CH$_3$ | Cyclopropyl | 3-i-C$_3$H$_7$ |
| CH$_3$ | Cyclopropyl | 4-i-C$_3$H$_7$ |
| CH$_3$ | Cyclopropyl | 3-Cyclopropyl |
| CH$_3$ | Cyclopropyl | 4-Cyclopropyl |
| CH$_3$ | Cyclopropyl | 3-n-C$_4$H$_9$ |
| CH$_3$ | Cyclopropyl | 4-n-C$_4$H$_9$ |
| CH$_3$ | Cyclopropyl | 3-t-C$_4$H$_9$ |
| CH$_3$ | Cyclopropyl | 4-t-C$_4$H$_9$ |
| CH$_3$ | Cyclopropyl | 3-n-C$_6$H$_{13}$ |
| CH$_3$ | Cyclopropyl | 4-n-C$_6$H$_{13}$ |
| CH$_3$ | Cyclopropyl | 3-Cyclohexyl |
| CH$_3$ | Cyclopropyl | 4-Cyclohexyl |
| CH$_3$ | Cyclopropyl | 3-Phenyl |
| CH$_3$ | Cyclopropyl | 4-Phenyl |
| CH$_3$ | Cyclopropyl | 4-Allyl |
| CH$_3$ | Cyclopropyl | 4-Propargyl |
| CH$_3$ | Cyclopropyl | 2-CH$_3$, 4-C$_2$H$_5$ |
| CH$_3$ | Cyclopropyl | 2-CH$_3$, 4-i-C$_3$H$_7$ |
| CH$_3$ | Cyclopropyl | 2-CH$_3$, 4-t-C$_4$H$_9$ |
| CH$_3$ | Cyclopropyl | 2-CH$_3$, 4-phenyl |
| CH$_3$ | Cyclopropyl | 3-CH$_3$, 4-phenyl |
| CH$_3$ | Cyclopropyl | 3-OH |
| CH$_3$ | Cyclopropyl | 4-OH |
| CH$_3$ | Cyclopropyl | 3-OCH$_3$ |
| CH$_3$ | Cyclopropyl | 4-OCH$_3$ |
| CH$_3$ | Cyclopropyl | 3,4-(OCH$_3$)$_2$ |
| CH$_3$ | Cyclopropyl | 3,5-(OCH$_3$)$_2$ |
| CH$_3$ | Cyclopropyl | 3,4,5-(OCH$_3$)$_3$ |
| CH$_3$ | Cyclopropyl | 4-OC$_2$H$_5$ |
| CH$_3$ | Cyclopropyl | 4-O-i-C$_3$H$_7$ |
| CH$_3$ | Cyclopropyl | 3-O-t-C$_4$H$_9$ |
| CH$_3$ | Cyclopropyl | 4-O-t-C$_4$H$_9$ |
| CH$_3$ | Cyclopropyl | 4-O-n-C$_6$H$_{13}$ |
| CH$_3$ | Cyclopropyl | 3-O-Phenyl |
| CH$_3$ | Cyclopropyl | 4-O-Phenyl |
| CH$_3$ | Cyclopropyl | 4-O-Allyl |
| CH$_3$ | Cyclopropyl | 2-CF$_3$ |
| CH$_3$ | Cyclopropyl | 3-CF$_3$ |
| CH$_3$ | Cyclopropyl | 4-CF$_3$ |
| CH$_3$ | Cyclopropyl | 3,5-(CF$_3$)$_2$ |
| CH$_3$ | Cyclopropyl | 4-CH$_2$CF$_3$ |
| CH$_3$ | Cyclopropyl | 4-C$_2$F$_5$ |
| CH$_3$ | Cyclopropyl | 4-CF$_2$CHF$_2$ |
| CH$_3$ | Cyclopropyl | 3-OCF$_3$ |
| CH$_3$ | Cyclopropyl | 4-OCF$_3$ |
| CH$_3$ | Cyclopropyl | 4-OCH$_2$CF$_3$ |
| CH$_3$ | Cyclopropyl | 4-OC$_2$F$_5$ |
| CH$_3$ | Cyclopropyl | 4-OCF$_2$CHF$_2$ |
| CH$_3$ | Cyclopropyl | 3-CH$_2$OCH$_3$ |
| CH$_3$ | Cyclopropyl | 4-CH$_2$OCH$_3$ |
| CH$_3$ | Cyclopropyl | 4-CH$_2$—O-t-C$_4$H$_9$ |
| CH$_3$ | Cyclopropyl | 4-CH(OCH$_3$)$_2$ |
| CH$_3$ | Cyclopropyl | 4-CH$_2$CN |
| CH$_3$ | Cyclopropyl | 3-CHO |

TABLE A-continued

| R | A | Q_m |
|---|---|---|
| CH_3 | Cyclopropyl | 4-CHO |
| CH_3 | Cyclopropyl | 3-CO—CH_3 |
| CH_3 | Cyclopropyl | 4-CO—CH_3 |
| CH_3 | Cyclopropyl | 3-COOH |
| CH_3 | Cyclopropyl | 4-COOH |
| CH_3 | Cyclopropyl | 3-COOCH_3 |
| CH_3 | Cyclopropyl | 4-COOCH_3 |
| CH_3 | Cyclopropyl | 3-COOC_2H_5 |
| CH_3 | Cyclopropyl | 4-COOC_2H_5 |
| CH_3 | Cyclopropyl | 3-COO-i-C_3H_7 |
| CH_3 | Cyclopropyl | 4-COO-i-C_3H_7 |
| CH_3 | Cyclopropyl | 3-COO-t-C_4H_9 |
| CH_3 | Cyclopropyl | 4-COO-t-C_4H_9 |
| CH_3 | Cyclopropyl | 3-COO-n-C_6H_13 |
| CH_3 | Cyclopropyl | 4-COO-n-C_6H_13 |
| CH_3 | Cyclopropyl | 3-CONH_2 |
| CH_3 | Cyclopropyl | 4-CONH_2 |
| CH_3 | Cyclopropyl | 3-CONHCH_3 |
| CH_3 | Cyclopropyl | 4-CONHCH_3 |
| CH_3 | Cyclopropyl | 3-CON(CH_3)_2 |
| CH_3 | Cyclopropyl | 4-CON(CH_3)_2 |
| CH_3 | Cyclopropyl | 3-CSNH_2 |
| CH_3 | Cyclopropyl | 4-CSNH_2 |
| CH_3 | Cyclopropyl | 3-NH_2 |
| CH_3 | Cyclopropyl | 4-NH_2 |
| CH_3 | Cyclopropyl | 4-NHCH_3 |
| CH_3 | Cyclopropyl | 4-N(CH_3)_2 |
| CH_3 | Cyclopropyl | 3-NHCO—CH_3 |
| CH_3 | Cyclopropyl | 4-NHCO—CH_3 |
| CH_3 | Cyclopropyl | 4-NCH_3—CO—CH_3 |
| CH_3 | Cyclopropyl | 4-NHCOOCH_3 |
| CH_3 | Cyclopropyl | 4-NCH_3—COOCH_3 |
| CH_3 | Cyclopropyl | 3-OCO—CH_3 |
| CH_3 | Cyclopropyl | 4-OCO—CH_3 |
| CH_3 | Cyclopropyl | 4-OCO-t-C_4H_9 |
| CH_3 | Cyclopropyl | 4-SH |
| CH_3 | Cyclopropyl | 4-SCH_3 |
| CH_3 | Cyclopropyl | 4-S-t-C_4H_9 |
| CH_3 | Cyclopropyl | 4-SO—CH_3 |
| CH_3 | Cyclopropyl | 4-SO_2—CH_3 |
| CH_3 | Cyclopropyl | 4-C(CH_3)=NCH_3 |
| CH_3 | Cyclopropyl | 4-C(SCH_3)=NOCH_3 |
| CH_3 | Cyclopropyl | 4-C(OCH_3)=NOCH_3 |
| CH_3 | Cyclopropyl | 3-CH=NOCH_3 |
| CH_3 | Cyclopropyl | 4-CH=NOCH_3 |
| CH_3 | Cyclopropyl | 3-C(CH_3)=NOCH_3 |
| CH_3 | Cyclopropyl | 4-C(CH_3)=NOCH_3 |
| CH_3 | Cyclopropyl | 4-C(CH_3)=NOC_2H_5 |
| CH_3 | Cyclopropyl | 4-C(CH_3)=NO-n-C_3H_7 |
| CH_3 | Cyclopropyl | 4-C(CH_3)=NO-i-C_3H_7 |
| CH_3 | Cyclopropyl | 4-C(CH_3)=NO-n-C_4H_9 |
| CH_3 | Cyclopropyl | 4-C(CH_3)=NO-t-C_4H_9 |
| CH_3 | Cyclopropyl | 4-C(CH_3)=NO-n-C_5H_11 |
| CH_3 | Cyclopropyl | 4-C(CH_3)=NO-n-C_6H_13 |
| CH_3 | Cyclopropyl | 2-Cl, 4-CH_3 |
| CH_3 | Cyclopropyl | 3-Cl, 5-CH_3 |
| CH_3 | Cyclopropyl | 2-CH_3, 4-Cl |
| CH_3 | Cyclopropyl | 3-CH_3, 4-Cl |
| CH_3 | Cyclopropyl | 3-F, 5-CH_3 |
| CH_3 | Cyclopropyl | 3-Br, 5-CH_3 |
| CH_3 | Cyclopropyl | 3-Cl, 5-NO_2 |
| CH_3 | Cyclopropyl | 3-NO_2, 4-Cl |
| CH_3 | Cyclopropyl | 3-Cl, 4-OCH_3 |
| CH_3 | Cyclopropyl | 3-OCH_3, 4-Cl |
| CH_3 | Cyclopropyl | 3-Cl, 5-CF_3 |
| CH_3 | Cyclopropyl | 3-Cl, 5-OCF_3 |
| CH_3 | Cyclopropyl | 3-F, 5-CF_3 |
| CH_3 | Cyclopropyl | 2-CH_3, 4-CN |
| CH_3 | Cyclopropyl | 2-CH_3, 4-OCH_3 |
| CH_3 | Cyclopropyl | 2-CH_3, 4-CF_3 |
| CH_3 | Cyclopropyl | 2-CH_3, 4-C(CH_3)=NOCH_3 |
| CH_3 | Cyclopropyl | 3-CH_3, 4-C(CH_3)=NOCH_3 |
| CH_3 | Cyclopropyl | 2-OH, 5-CH_3 |
| CH_3 | Cyclopropyl | 3-CH_3, 4-O-t-C_4H_9 |
| CH_3 | Cyclopropyl | 2-C(COOCH_3)=NOCH_3 |
| CH_3 | Cyclopropyl | |
| H | C_2H_5 | H |
| H | C_2H_5 | 2-F |
| H | C_2H_5 | 3-F |
| H | C_2H_5 | 4-F |
| H | C_2H_5 | 2,3-F_2 |
| H | C_2H_5 | 2,4-F_2 |
| H | C_2H_5 | 2,5-F_2 |
| H | C_2H_5 | 2,6-F_2 |
| H | C_2H_5 | 3,4-F_2 |
| H | C_2H_5 | 3,5-F_2 |
| H | C_2H_5 | 2-Cl |
| H | C_2H_5 | 3-Cl |
| H | C_2H_5 | 4-Cl |
| H | C_2H_5 | 2,4-Cl_2 |
| H | C_2H_5 | 2,5-Cl_2 |
| H | C_2H_5 | 3,4-Cl_2 |
| H | C_2H_5 | 3,5-Cl_2 |
| H | C_2H_5 | 2-Br |
| H | C_2H_5 | 3-Br |
| H | C_2H_5 | 4-Br |
| H | C_2H_5 | 2,4-Br_2 |
| H | C_2H_5 | 3,4-Br_2 |
| H | C_2H_5 | 3,5-Br_2 |
| H | C_2H_5 | 2-I |
| H | C_2H_5 | 3-I |
| H | C_2H_5 | 4-I |
| H | C_2H_5 | 2-F, 4-Cl |
| H | C_2H_5 | 2-F, 5-Cl |
| H | C_2H_5 | 2-F, 4-Br |
| H | C_2H_5 | 2-F, 5-Br |
| H | C_2H_5 | 2-Cl, 4-Br |
| H | C_2H_5 | 2-Cl, 5-Br |
| H | C_2H_5 | 3-F, 4-Cl |
| H | C_2H_5 | 3-F, 5-Cl |
| H | C_2H_5 | 3-F, 4-Br |
| H | C_2H_5 | 3-F, 5-Br |
| H | C_2H_5 | 3-Cl, 4-Br |
| H | C_2H_5 | 3-Cl, 5-Br |
| H | C_2H_5 | 3-Cl, 4-F |
| H | C_2H_5 | 3-Br, 4-F |
| H | C_2H_5 | 3-Br, 4-Cl |
| H | C_2H_5 | 2-NO_2 |
| H | C_2H_5 | 3-NO_2 |
| H | C_2H_5 | 4-NO_2 |
| H | C_2H_5 | 2-CN |
| H | C_2H_5 | 3-CN |
| H | C_2H_5 | 4-CN |
| H | C_2H_5 | 2-CH_3 |
| H | C_2H_5 | 3-CH_3 |
| H | C_2H_5 | 4-CH_3 |
| H | C_2H_5 | 2,3-(CH_3)_2 |
| H | C_2H_5 | 2,4-(CH_3)_2 |
| H | C_2H_5 | 2,5-(CH_3)_2 |
| H | C_2H_5 | 2,6-(CH_3)_2 |
| H | C_2H_5 | 3,4-(CH_3)_2 |
| H | C_2H_5 | 3,5-(CH_3)_2 |
| H | C_2H_5 | 2,4,5-(CH_3)_3 |
| H | C_2H_5 | 2,4,6-(CH_3)_3 |
| H | C_2H_5 | 3,4,5-(CH_3)_3 |
| H | C_2H_5 | 2-C_2H_5 |
| H | C_2H_5 | 3-C_2H_5 |
| H | C_2H_5 | 4-C_2H_5 |
| H | C_2H_5 | 3,4-(C_2H_5)_2 |
| H | C_2H_5 | 3,5-(C_2H_5)_2 |
| H | C_2H_5 | 3-n-C_3H_7 |
| H | C_2H_5 | 4-n-C_3H_7 |
| H | C_2H_5 | 3,4-(n-C_3H_7)_2 |
| H | C_2H_5 | 3,5-(n-C_3H_7)_2 |
| H | C_2H_5 | 3-i-C_3H_7 |
| H | C_2H_5 | 4-i-C_3H_7 |
| H | C_2H_5 | 3,4-(i-C_3H_7)_2 |
| H | C_2H_5 | 3,5-(i-C_3H_7)_2 |
| H | C_2H_5 | 3-Cyclopropyl |
| H | C_2H_5 | 4-Cyclopropyl |
| H | C_2H_5 | 3-n-C_4H_9 |
| H | C_2H_5 | 4-n-C_4H_9 |
| H | C_2H_5 | 3,4-(n-C_4H_9)_2 |

TABLE A-continued

| R | A | $Q_m$ |
|---|---|---|
| H | $C_2H_5$ | 3,5-$(n-C_4H_9)_2$ |
| H | $C_2H_5$ | 3-s-$C_4H_9$ |
| H | $C_2H_5$ | 4-s-$C_4H_9$ |
| H | $C_2H_5$ | 3-i-$C_4H_9$ |
| H | $C_2H_5$ | 4-i-$C_4H_9$ |
| H | $C_2H_5$ | 3-t-$C_4H_9$ |
| H | $C_2H_5$ | 4-t-$C_4H_9$ |
| H | $C_2H_5$ | 3,4-$(t-C_4H_9)_2$ |
| H | $C_2H_5$ | 3,5-$(t-C_4H_9)_2$ |
| H | $C_2H_5$ | 3-n-$C_5H_{11}$ |
| H | $C_2H_5$ | 4-n-$C_5H_{11}$ |
| H | $C_2H_5$ | 3-n-$C_6H_{13}$ |
| H | $C_2H_5$ | 4-n-$C_6H_{13}$ |
| H | $C_2H_5$ | 3-Cyclohexyl |
| H | $C_2H_5$ | 4-Cyclohexyl |
| H | $C_2H_5$ | 3-Phenyl |
| H | $C_2H_5$ | 4-Phenyl |
| H | $C_2H_5$ | 3-Vinyl |
| H | $C_2H_5$ | 4-Vinyl |
| H | $C_2H_5$ | 3-Allyl |
| H | $C_2H_5$ | 4-Allyl |
| H | $C_2H_5$ | 3-Propargyl |
| H | $C_2H_5$ | 4-Propargyl |
| H | $C_2H_5$ | 3-(Propen-2-yl) |
| H | $C_2H_5$ | 4-(Propen-2-yl) |
| H | $C_2H_5$ | 2-$CH_3$, 4-$C_2H_5$ |
| H | $C_2H_5$ | 2-$CH_3$, 5-$C_2H_5$ |
| H | $C_2H_5$ | 2-$CH_3$, 4-n-$C_3H_7$ |
| H | $C_2H_5$ | 2-$CH_3$, 5-n-$C_3H_7$ |
| H | $C_2H_5$ | 2-$CH_3$, 4-i-$C_3H_7$ |
| H | $C_2H_5$ | 2-$CH_3$, 5-i-$C_3H_7$ |
| H | $C_2H_5$ | 2-$CH_3$, 4-n-$C_4H_9$ |
| H | $C_2H_5$ | 2-$CH_3$, 4-s-$C_4H_9$ |
| H | $C_2H_5$ | 2-$CH_3$, 4-i-$C_4H_9$ |
| H | $C_2H_5$ | 2-$CH_3$, 4-t-$C_4H_9$ |
| H | $C_2H_5$ | 2-$CH_3$, 4-phenyl |
| H | $C_2H_5$ | 2-$CH_3$, 5-phenyl |
| H | $C_2H_5$ | 2-$CH_3$, 4-vinyl |
| H | $C_2H_5$ | 2-$CH_3$, 4-allyl |
| H | $C_2H_5$ | 2-$CH_3$, 4-propargyl |
| H | $C_2H_5$ | 2-$CH_3$, 4-(propen-2-yl) |
| H | $C_2H_5$ | 3-$CH_3$, 4-$C_2H_5$ |
| H | $C_2H_5$ | 3-$CH_3$, 5-$C_2H_5$ |
| H | $C_2H_5$ | 3-$CH_3$, 4-n-$C_3H_7$ |
| H | $C_2H_5$ | 3-$CH_3$, 5-n-$C_3H_7$ |
| H | $C_2H_5$ | 3-$CH_3$, 4-i-$C_3H_7$ |
| H | $C_2H_5$ | 3-$CH_3$, 5-i-$C_3H_7$ |
| H | $C_2H_5$ | 3-$CH_3$, 4-cyclopropyl |
| H | $C_2H_5$ | 3-$CH_3$, 4-t-$C_4H_9$ |
| H | $C_2H_5$ | 3-$CH_3$, 5-t-$C_4H_9$ |
| H | $C_2H_5$ | 3-$CH_3$, 4-phenyl |
| H | $C_2H_5$ | 3-$CH_3$, 5-phenyl |
| H | $C_2H_5$ | 3-$CH_3$, 4-vinyl |
| H | $C_2H_5$ | 3-$CH_3$, 4-allyl |
| H | $C_2H_5$ | 3-$CH_3$, 4-propargyl |
| H | $C_2H_5$ | 3-$CH_3$, 4-propen-2-yl |
| H | $C_2H_5$ | 3-$C_2H_5$, 4-$CH_3$ |
| H | $C_2H_5$ | 3-i-$C_3H_7$, 4-$CH_3$ |
| H | $C_2H_5$ | 3-t-$C_4H_9$, 4-$CH_3$ |
| H | $C_2H_5$ | 3-Phenyl, 4-$CH_3$ |
| H | $C_2H_5$ | 2-OH |
| H | $C_2H_5$ | 3-OH |
| H | $C_2H_5$ | 4-OH |
| H | $C_2H_5$ | 2-$OCH_3$ |
| H | $C_2H_5$ | 3-$OCH_3$ |
| H | $C_2H_5$ | 4-$OCH_3$ |
| H | $C_2H_5$ | 2,3-$(OCH_3)_2$ |
| H | $C_2H_5$ | 2,4-$(OCH_3)_2$ |
| H | $C_2H_5$ | 2,5-$(OCH_3)_2$ |
| H | $C_2H_5$ | 3,4-$(OCH_3)_2$ |
| H | $C_2H_5$ | 3,5-$(OCH_3)_2$ |
| H | $C_2H_5$ | 3,4,5-$(OCH_3)_3$ |
| H | $C_2H_5$ | 3-$OC_2H_5$ |
| H | $C_2H_5$ | 4-$OC_2H_5$ |
| H | $C_2H_5$ | 3,4-$(OC_2H_5)_2$ |
| H | $C_2H_5$ | 3,5-$(OC_2H_5)_2$ |
| H | $C_2H_5$ | 3-O-n-$C_3H_7$ |
| H | $C_2H_5$ | 4-O-n-$C_3H_7$ |
| H | $C_2H_5$ | 3-O-i-$C_3H_7$ |
| H | $C_2H_5$ | 4-O-i-$C_3H_7$ |
| H | $C_2H_5$ | 3-O-Cyclopropyl |
| H | $C_2H_5$ | 4-O-Cyclopropyl |
| H | $C_2H_5$ | 3-O-n-$C_4H_9$ |
| H | $C_2H_5$ | 4-O-n-$C_4H_9$ |
| H | $C_2H_5$ | 3-O-s-$C_4H_9$ |
| H | $C_2H_5$ | 4-O-s-$C_4H_9$ |
| H | $C_2H_5$ | 3-O-i-$C_4H_9$ |
| H | $C_2H_5$ | 4-O-i-$C_4H_9$ |
| H | $C_2H_5$ | 3-O-t-$C_4H_9$ |
| H | $C_2H_5$ | 4-O-t-$C_4H_9$ |
| H | $C_2H_5$ | 3-O-n-$C_5H_{11}$ |
| H | $C_2H_5$ | 4-O-n-$C_5H_{11}$ |
| H | $C_2H_5$ | 3-O-n-$C_6H_{13}$ |
| H | $C_2H_5$ | 4-O-n-$C_6H_{13}$ |
| H | $C_2H_5$ | 3-O-Cyclohexyl |
| H | $C_2H_5$ | 4-O-Cyclohexyl |
| H | $C_2H_5$ | 3-O-Phenyl |
| H | $C_2H_5$ | 4-O-Phenyl |
| H | $C_2H_5$ | 3-O-Allyl |
| H | $C_2H_5$ | 4-O-Allyl |
| H | $C_2H_5$ | 2-$CF_3$ |
| H | $C_2H_5$ | 3-$CF_3$ |
| H | $C_2H_5$ | 4-$CF_3$ |
| H | $C_2H_5$ | 2,4-$(CF_3)_2$ |
| H | $C_2H_5$ | 3,5-$(CF_3)_2$ |
| H | $C_2H_5$ | 3-$CF_2Cl$ |
| H | $C_2H_5$ | 4-$CF_2Cl$ |
| H | $C_2H_5$ | 3-$CFCl_2$ |
| H | $C_2H_5$ | 4-$CFCl_2$ |
| H | $C_2H_5$ | 3-$CCl_3$ |
| H | $C_2H_5$ | 4-$CCl_3$ |
| H | $C_2H_5$ | 3-$CH_2CH_2F$ |
| H | $C_2H_5$ | 4-$CH_2CH_2F$ |
| H | $C_2H_5$ | 3-$CH_2CF_3$ |
| H | $C_2H_5$ | 4-$CH_2CF_3$ |
| H | $C_2H_5$ | 3-$C_2F_5$ |
| H | $C_2H_5$ | 4-$C_2F_5$ |
| H | $C_2H_5$ | 3-$CHCl_2$ |
| H | $C_2H_5$ | 4-$CHCl_2$ |
| H | $C_2H_5$ | 3-$CH_2Cl$ |
| H | $C_2H_5$ | 4-$CH_2Cl$ |
| H | $C_2H_5$ | 3-$CF_2CHF_2$ |
| H | $C_2H_5$ | 4-$CF_2CHF_2$ |
| H | $C_2H_5$ | 3-$CH_2CH_2Cl$ |
| H | $C_2H_5$ | 4-$CH_2CH_2Cl$ |
| H | $C_2H_5$ | 2-$OCF_3$ |
| H | $C_2H_5$ | 3-$OCF_3$ |
| H | $C_2H_5$ | 4-$OCF_3$ |
| H | $C_2H_5$ | 3-$OCHF_2$ |
| H | $C_2H_5$ | 4-$OCHF_2$ |
| H | $C_2H_5$ | 3-$OC_2F_5$ |
| H | $C_2H_5$ | 4-$OC_2F_5$ |
| H | $C_2H_5$ | 3-$OCF_2CHF_2$ |
| H | $C_2H_5$ | 4-$OCF_2CHF_2$ |
| H | $C_2H_5$ | 3-$CH_2OCH_3$ |
| H | $C_2H_5$ | 4-$CH_2OCH_3$ |
| H | $C_2H_5$ | 3-$CH_2$O-t-$C_4H_9$ |
| H | $C_2H_5$ | 4-$CH_2$O-t-$C_4H_9$ |
| H | $C_2H_5$ | 3-$C(CH_3)(OCH_3)_2$ |
| H | $C_2H_5$ | 4-$C(CH_3)(OCH_3)_2$ |
| H | $C_2H_5$ | 3-$CH(OCH_3)_2$ |
| H | $C_2H_5$ | 4-$CH(OCH_3)_2$ |
| H | $C_2H_5$ | 3-$CH_2CN$ |
| H | $C_2H_5$ | 4-$CH_2CN$ |
| H | $C_2H_5$ | 3-CHO |
| H | $C_2H_5$ | 4-CHO |
| H | $C_2H_5$ | 3-CO—$CH_3$ |
| H | $C_2H_5$ | 4-CO—$CH_3$ |
| H | $C_2H_5$ | 3-CO—$C_2H_5$ |
| H | $C_2H_5$ | 4-CO—$C_2H_5$ |
| H | $C_2H_5$ | 2-COOH |
| H | $C_2H_5$ | 3-COOH |
| H | $C_2H_5$ | 4-COOH |
| H | $C_2H_5$ | 3-$COOCH_3$ |

TABLE A-continued

| R | A | $Q_m$ |
|---|---|---|
| H | $C_2H_5$ | 4-COOCH$_3$ |
| H | $C_2H_5$ | 3-COOC$_2$H$_5$ |
| H | $C_2H_5$ | 4-COOC$_2$H$_5$ |
| H | $C_2H_5$ | 3-COO-n-C$_3$H$_7$ |
| H | $C_2H_5$ | 4-COO-n-C$_3$H$_7$ |
| H | $C_2H_5$ | 3-COO-i-C$_3$H$_7$ |
| H | $C_2H_5$ | 4-COO-i-C$_3$H$_7$ |
| H | $C_2H_5$ | 3-COO-n-C$_4$H$_9$ |
| H | $C_2H_5$ | 4-COO-n-C$_4$H$_9$ |
| H | $C_2H_5$ | 3-COO-s-C$_4$H$_9$ |
| H | $C_2H_5$ | 4-COO-s-C$_4$H$_9$ |
| H | $C_2H_5$ | 3-COO-i-C$_4$H$_9$ |
| H | $C_2H_5$ | 4-COO-i-C$_4$H$_9$ |
| H | $C_2H_5$ | 3-COO-t-C$_4$H$_9$ |
| H | $C_2H_5$ | 4-COO-t-C$_4$H$_9$ |
| H | $C_2H_5$ | 3-COO-n-C$_5$H$_{11}$ |
| H | $C_2H_5$ | 4-COO-n-C$_5$H$_{11}$ |
| H | $C_2H_5$ | 3-COO-n-C$_6$H$_{13}$ |
| H | $C_2H_5$ | 4-COO-n-C$_6$H$_{13}$ |
| H | $C_2H_5$ | 2-CONH$_2$ |
| H | $C_2H_5$ | 3-CONH$_2$ |
| H | $C_2H_5$ | 4-CONH$_2$ |
| H | $C_2H_5$ | 3-CONHCH$_3$ |
| H | $C_2H_5$ | 4-CONHCH$_3$ |
| H | $C_2H_5$ | 3-CON(CH$_3$)$_2$ |
| H | $C_2H_5$ | 4-CON(CH$_3$)$_2$ |
| H | $C_2H_5$ | 3-CON(C$_2$H$_5$)$_2$ |
| H | $C_2H_5$ | 4-CON(C$_2$H$_5$)$_2$ |
| H | $C_2H_5$ | 2-CSNH$_2$ |
| H | $C_2H_5$ | 3-CSNH$_2$ |
| H | $C_2H_5$ | 4-CSNH$_2$ |
| H | $C_2H_5$ | 2-NH$_2$ |
| H | $C_2H_5$ | 3-NH$_2$ |
| H | $C_2H_5$ | 4-NH$_2$ |
| H | $C_2H_5$ | 3-NHCH$_3$ |
| H | $C_2H_5$ | 4-NHCH$_3$ |
| H | $C_2H_5$ | 3-N(CH$_3$)$_2$ |
| H | $C_2H_5$ | 4-N(CH$_3$)$_2$ |
| H | $C_2H_5$ | 3-NHCO—CH$_3$ |
| H | $C_2H_5$ | 4-NHCO—CH$_3$ |
| H | $C_2H_5$ | 3-NCH$_3$—CO—CH$_3$ |
| H | $C_2H_5$ | 4-NCH$_3$—CO—CH$_3$ |
| H | $C_2H_5$ | 3-NHCOOCH$_3$ |
| H | $C_2H_5$ | 4-NHCOOCH$_3$ |
| H | $C_2H_5$ | 3-NCH$_3$—COOCH$_3$ |
| H | $C_2H_5$ | 4-NCH$_3$—COOCH$_3$ |
| H | $C_2H_5$ | 3-OCO—CH$_3$ |
| H | $C_2H_5$ | 4-OCO—CH$_3$ |
| H | $C_2H_5$ | 3-OCO-t-C$_4$H$_9$ |
| H | $C_2H_5$ | 4-OCO-t-C$_4$H$_9$ |
| H | $C_2H_5$ | 3-SH |
| H | $C_2H_5$ | 4-SH |
| H | $C_2H_5$ | 3-SCH$_3$ |
| H | $C_2H_5$ | 4-SCH$_3$ |
| H | $C_2H_5$ | 3-S-t-C$_4$H$_9$ |
| H | $C_2H_5$ | 4-S-t-C$_4$H$_9$ |
| H | $C_2H_5$ | 3-SO—CH$_3$ |
| H | $C_2H_5$ | 4-SO—CH$_3$ |
| H | $C_2H_5$ | 3-SO$_2$CH$_3$ |
| H | $C_2H_5$ | 4-SO$_2$CH$_3$ |
| H | $C_2H_5$ | 3-CH=NCH$_3$ |
| H | $C_2H_5$ | 4-CH=NCH$_3$ |
| H | $C_2H_5$ | 3-C(CH$_3$)=NCH$_3$ |
| H | $C_2H_5$ | 4-C(CH$_3$)=NCH$_3$ |
| H | $C_2H_5$ | 3-C(SCH$_3$)=NOCH$_3$ |
| H | $C_2H_5$ | 4-C(SCH$_3$)=NOCH$_3$ |
| H | $C_2H_5$ | 3-C(OCH$_3$)=NOCH$_3$ |
| H | $C_2H_5$ | 4-C(OCH$_3$)=NOCH$_3$ |
| H | $C_2H_5$ | 3-C(NH$_2$)=NOCH$_3$ |
| H | $C_2H_5$ | 4-C(NH$_2$)=NOCH$_3$ |
| H | $C_2H_5$ | 3-C(NHCH$_3$)=NOCH$_3$ |
| H | $C_2H_5$ | 4-C(NHCH$_3$)=NOCH$_3$ |
| H | $C_2H_5$ | 3-CH=NOCH$_3$ |
| H | $C_2H_5$ | 4-CH=NOCH$_3$ |
| H | $C_2H_5$ | 3-C(CH$_3$)=NOCH$_3$ |
| H | $C_2H_5$ | 4-C(CH$_3$)=NOCH$_3$ |
| H | $C_2H_5$ | 3-C(CH$_3$)=NOC$_2$H$_5$ |
| H | $C_2H_5$ | 4-C(CH$_3$)=NOC$_2$H$_5$ |
| H | $C_2H_5$ | 3-C(CH$_3$)=NO-n-C$_3$H$_7$ |
| H | $C_2H_5$ | 4-C(CH$_3$)=NO-n-C$_3$H$_7$ |
| H | $C_2H_5$ | 3-C(CH$_3$)=NO-i-C$_3$H$_7$ |
| H | $C_2H_5$ | 4-C(CH$_3$)=NO-i-C$_3$H$_7$ |
| H | $C_2H_5$ | 3-C(CH$_3$)=NO-n-C$_4$H$_9$ |
| H | $C_2H_5$ | 4-C(CH$_3$)=NO-n-C$_4$H$_9$ |
| H | $C_2H_5$ | 3-C(CH$_3$)=NO-s-C$_4$H$_9$ |
| H | $C_2H_5$ | 4-C(CH$_3$)=NO-s-C$_4$H$_9$ |
| H | $C_2H_5$ | 3-C(CH$_3$)=NO-i-C$_4$H$_9$ |
| H | $C_2H_5$ | 4-C(CH$_3$)=NO-i-C$_4$H$_9$ |
| H | $C_2H_5$ | 3-C(CH$_3$)=NO-t-C$_4$H$_9$ |
| H | $C_2H_5$ | 4-C(CH$_3$)=NO-t-C$_4$H$_9$ |
| H | $C_2H_5$ | 3-C(CH$_3$)=NO-n-C$_5$H$_{11}$ |
| H | $C_2H_5$ | 4-C(CH$_3$)=NO-n-C$_5$H$_{11}$ |
| H | $C_2H_5$ | 3-C(CH$_3$)=NO-n-C$_6$H$_{13}$ |
| H | $C_2H_5$ | 4-C(CH$_3$)=NO-n-C$_6$H$_{13}$ |
| H | $C_2H_5$ | 2-Cl, 4-CH$_3$ |
| H | $C_2H_5$ | 2-Cl, 5-CH$_3$ |
| H | $C_2H_5$ | 3-Cl, 4-CH$_3$ |
| H | $C_2H_5$ | 3-Cl, 5-CH$_3$ |
| H | $C_2H_5$ | 2-CH$_3$, 4-Cl |
| H | $C_2H_5$ | 2-CH$_3$, 5-Cl |
| H | $C_2H_5$ | 3-CH$_3$, 4-Cl |
| H | $C_2H_5$ | 3-Cl, 5-t-C$_4$H$_9$ |
| H | $C_2H_5$ | 2-Cl, 4-t-C$_4$H$_9$ |
| H | $C_2H_5$ | 2-F, 4-CH$_3$ |
| H | $C_2H_5$ | 3-F, 4-CH$_3$ |
| H | $C_2H_5$ | 3-F, 5-CH$_3$ |
| H | $C_2H_5$ | 2-CH$_3$, 4-F |
| H | $C_2H_5$ | 3-CH$_3$, 4-F |
| H | $C_2H_5$ | 2-F, 4-t-C$_4$H$_9$ |
| H | $C_2H_5$ | 3-F, 4-t-C$_4$H$_9$ |
| H | $C_2H_5$ | 2-F, 4-OCH$_3$ |
| H | $C_2H_5$ | 2-Br, 4-CH$_3$ |
| H | $C_2H_5$ | 3-Br, 4-CH$_3$ |
| H | $C_2H_5$ | 3-Br, 5-CH$_3$ |
| H | $C_2H_5$ | 2-CH$_3$, 4-Br |
| H | $C_2H_5$ | 3-CH$_3$, 4-Br |
| H | $C_2H_5$ | 2-Br, 4-t-C$_4$H$_9$ |
| H | $C_2H_5$ | 2-Cl, 4-NO$_2$ |
| H | $C_2H_5$ | 3-Cl, 4-NO$_2$ |
| H | $C_2H_5$ | 3-Cl, 5-NO$_2$ |
| H | $C_2H_5$ | 3-NO$_2$, 4-Cl |
| H | $C_2H_5$ | 3-Cl, 4-OCH |
| H | $C_2H_5$ | 3-OCH$_3$, 4-Cl |
| H | $C_2H_5$ | 2-Cl, 5-CF$_3$ |
| H | $C_2H_5$ | 3-Cl, 4-CF$_3$ |
| H | $C_2H_5$ | 3-Cl, 5-CF$_3$ |
| H | $C_2H_5$ | 3-CF$_3$, 4-Cl |
| H | $C_2H_5$ | 3-Cl, 5-OCF$_3$ |
| H | $C_2H_5$ | 3-F, 5-CF$_3$ |
| H | $C_2H_5$ | 2-CH$_3$, 4-CN |
| H | $C_2H_5$ | 3-NO$_2$, 4-CH$_3$ |
| H | $C_2H_5$ | 2-CH$_3$, 4-OCH$_3$ |
| H | $C_2H_5$ | 3-CH$_3$, 4-OCH$_3$ |
| H | $C_2H_5$ | 3-CH$_3$, 5-OCH$_3$ |
| H | $C_2H_5$ | 3-OCH$_3$, 4-CH$_3$ |
| H | $C_2H_5$ | 2-CH$_3$, 4-O-i-C$_3$H$_7$ |
| H | $C_2H_5$ | 3-CH$_3$, 4-O-i-C$_3$H$_7$ |
| H | $C_2H_5$ | 3-O-i-C$_3$H$_7$, 4-CH$_3$ |
| H | $C_2H_5$ | 2-CH$_3$, 4-CF$_3$ |
| H | $C_2H_5$ | 2-CH$_3$, 5-CF$_3$ |
| H | $C_2H_5$ | 3-CH$_3$, 4-CF$_3$ |
| H | $C_2H_5$ | 3-CH$_3$, 5-CF$_3$ |
| H | $C_2H_5$ | 3-CF$_3$, 4-CH$_3$ |
| H | $C_2H_5$ | 3-CF$_3$, 4-OCH$_3$ |
| H | $C_2H_5$ | 3-OCH$_3$, 4-CF$_3$ |
| H | $C_2H_5$ | 2-CH$_3$, 4-C(CH$_3$)=NOCH$_3$ |
| H | $C_2H_5$ | 3-CH$_3$, 4-C(CH$_3$)=NOCH$_3$ |
| H | $C_2H_5$ | 2-OH, 5-CH$_3$ |
| H | $C_2H_5$ | 3-CH$_3$, 4-OC$_2$H$_5$ |
| H | $C_2H_5$ | 3-CH$_3$, 4-O-t-C$_4$H$_9$ |
| H | $C_2H_5$ | 3-OC$_2$H$_5$, 4-CH$_3$ |
| H | $C_2H_5$ | 3-O-t-C$_4$H$_9$, 4-CH$_3$ |
| H | $C_2H_5$ | 2-C(COOCH$_3$)=NOCH$_3$ |
| H | $C_2H_5$ | |

TABLE A-continued

| R | A | Q$_m$ |
|---|---|---|
| H | C$_2$H$_5$ | H |
| CH$_3$ | C$_2$H$_5$ | 2-F |
| CH$_3$ | C$_2$H$_5$ | 3-F |
| CH$_3$ | C$_2$H$_5$ | 4-F |
| CH$_3$ | C$_2$H$_5$ | 2,4-F$_2$ |
| CH$_3$ | C$_2$H$_5$ | 3,4-F$_2$ |
| CH$_3$ | C$_2$H$_5$ | 3,5-F$_2$ |
| CH$_3$ | C$_2$H$_5$ | 2-Cl |
| CH$_3$ | C$_2$H$_5$ | 3-Cl |
| CH$_3$ | C$_2$H$_5$ | 4-Cl |
| CH$_3$ | C$_2$H$_5$ | 2,4-Cl$_2$ |
| CH$_3$ | C$_2$H$_5$ | 3,4-Cl$_2$ |
| CH$_3$ | C$_2$H$_5$ | 3,5-Cl$_2$ |
| CH$_3$ | C$_2$H$_5$ | 2-Br |
| CH$_3$ | C$_2$H$_5$ | 3-Br |
| CH$_3$ | C$_2$H$_5$ | 4-Br |
| CH$_3$ | C$_2$H$_5$ | 3,5-Br$_2$ |
| CH$_3$ | C$_2$H$_5$ | 3-I |
| CH$_3$ | C$_2$H$_5$ | 4-I |
| CH$_3$ | C$_2$H$_5$ | 3-F, 5-Cl |
| CH$_3$ | C$_2$H$_5$ | 3-F, 5-Br |
| CH$_3$ | C$_2$H$_5$ | 3-Cl, 5-Br |
| CH$_3$ | C$_2$H$_5$ | 3-Br, 4-F |
| CH$_3$ | C$_2$H$_5$ | 2-NO$_2$ |
| CH$_3$ | C$_2$H$_5$ | 3-NO$_2$ |
| CH$_3$ | C$_2$H$_5$ | 4-NO$_2$ |
| CH$_3$ | C$_2$H$_5$ | 2-CN |
| CH$_3$ | C$_2$H$_5$ | 3-CN |
| CH$_3$ | C$_2$H$_5$ | 4-CN |
| CH$_3$ | C$_2$H$_5$ | 2-CH$_3$ |
| CH$_3$ | C$_2$H$_5$ | 3-CH$_3$ |
| CH$_3$ | C$_2$H$_5$ | 4-CH$_3$ |
| CH$_3$ | C$_2$H$_5$ | 2,4-(CH$_3$)$_2$ |
| CH$_3$ | C$_2$H$_5$ | 2,5-(CH$_3$)$_2$ |
| CH$_3$ | C$_2$H$_5$ | 3,4-(CH$_3$)$_2$ |
| CH$_3$ | C$_2$H$_5$ | 3,5-(CH$_3$)$_2$ |
| CH$_3$ | C$_2$H$_5$ | 2,4,5-(CH$_3$)$_3$ |
| CH$_3$ | C$_2$H$_5$ | 2,4,6-(CH$_3$)$_3$ |
| CH$_3$ | C$_2$H$_5$ | 3-C$_2$H$_5$ |
| CH$_3$ | C$_2$H$_5$ | 4-C$_2$H$_5$ |
| CH$_3$ | C$_2$H$_5$ | 3,4-(C$_2$H$_5$)$_2$ |
| CH$_3$ | C$_2$H$_5$ | 3,5-(C$_2$H$_5$)$_2$ |
| CH$_3$ | C$_2$H$_5$ | 3-n-C$_3$H$_7$ |
| CH$_3$ | C$_2$H$_5$ | 4-n-C$_3$H$_7$ |
| CH$_3$ | C$_2$H$_5$ | 3-i-C$_3$H$_7$ |
| CH$_3$ | C$_2$H$_5$ | 4-i-C$_3$H$_7$ |
| CH$_3$ | C$_2$H$_5$ | 3-Cyclopropyl |
| CH$_3$ | C$_2$H$_5$ | 4-Cyclopropyl |
| CH$_3$ | C$_2$H$_5$ | 3-n-C$_4$H$_9$ |
| CH$_3$ | C$_2$H$_5$ | 4-n-C$_4$H$_9$ |
| CH$_3$ | C$_2$H$_5$ | 3-t-C$_4$H$_9$ |
| CH$_3$ | C$_2$H$_5$ | 4-t-C$_4$H$_9$ |
| CH$_3$ | C$_2$H$_5$ | 3-n-C$_6$H$_{13}$ |
| CH$_3$ | C$_2$H$_5$ | 4-n-C$_6$H$_{13}$ |
| CH$_3$ | C$_2$H$_5$ | 3-Cyclohexyl |
| CH$_3$ | C$_2$H$_5$ | 4-Cyclohexyl |
| CH$_3$ | C$_2$H$_5$ | 3-Phenyl |
| CH$_3$ | C$_2$H$_5$ | 4-Phenyl |
| CH$_3$ | C$_2$H$_5$ | 4-Allyl |
| CH$_3$ | C$_2$H$_5$ | 4-Propargyl |
| CH$_3$ | C$_2$H$_5$ | 2-CH$_3$, 4-C$_2$H$_5$ |
| CH$_3$ | C$_2$H$_5$ | 2-CH$_3$, 4-i-C$_3$H$_7$ |
| CH$_3$ | C$_2$H$_5$ | 2-CH$_3$, 4-t-C$_4$H$_9$ |
| CH$_3$ | C$_2$H$_5$ | 2-CH$_3$, 4-phenyl |
| CH$_3$ | C$_2$H$_5$ | 3-CH$_3$, 4-phenyl |
| CH$_3$ | C$_2$H$_5$ | 3-OH |
| CH$_3$ | C$_2$H$_5$ | 4-OH |
| CH$_3$ | C$_2$H$_5$ | 3-OCH$_3$ |
| CH$_3$ | C$_2$H$_5$ | 4-OCH$_3$ |
| CH$_3$ | C$_2$H$_5$ | 3,4-(OCH$_3$)$_2$ |
| CH$_3$ | C$_2$H$_5$ | 3,5-(OCH$_3$)$_2$ |
| CH$_3$ | C$_2$H$_5$ | 3,4,5-(OCH$_3$)$_3$ |
| CH$_3$ | C$_2$H$_5$ | 4-OC$_2$H$_5$ |
| CH$_3$ | C$_2$H$_5$ | 4-O-i-C$_3$H$_7$ |
| CH$_3$ | C$_2$H$_5$ | 3-O-t-C$_4$H$_9$ |
| CH$_3$ | C$_2$H$_5$ | 4-O-t-C$_4$H$_9$ |
| CH$_3$ | C$_2$H$_5$ | 4-O-n-C$_6$H$_{13}$ |
| CH$_3$ | C$_2$H$_5$ | 3-O-Phenyl |
| CH$_3$ | C$_2$H$_5$ | 4-O-Phenyl |
| CH$_3$ | C$_2$H$_5$ | 4-O-Allyl |
| CH$_3$ | C$_2$H$_5$ | 2-CF$_3$ |
| CH$_3$ | C$_2$H$_5$ | 3-CF$_3$ |
| CH$_3$ | C$_2$H$_5$ | 4-CF$_3$ |
| CH$_3$ | C$_2$H$_5$ | 3,5-(CF$_3$)$_2$ |
| CH$_3$ | C$_2$H$_5$ | 4-CH$_2$CF$_3$ |
| CH$_3$ | C$_2$H$_5$ | 4-C$_2$F$_5$ |
| CH$_3$ | C$_2$H$_5$ | 4-CF$_2$CHF$_2$ |
| CH$_3$ | C$_2$H$_5$ | 3-OCF$_3$ |
| CH$_3$ | C$_2$H$_5$ | 4-OCF$_3$ |
| CH$_3$ | C$_2$H$_5$ | 4-OCH$_2$CF$_3$ |
| CH$_3$ | C$_2$H$_5$ | 4-OC$_2$F$_5$ |
| CH$_3$ | C$_2$H$_5$ | 4-OCF$_2$CHF$_2$ |
| CH$_3$ | C$_2$H$_5$ | 3-CH$_2$OCH$_3$ |
| CH$_3$ | C$_2$H$_5$ | 4-CH$_2$OCH$_3$ |
| CH$_3$ | C$_2$H$_5$ | 4-CH$_2$—O-t-C$_4$H$_9$ |
| CH$_3$ | C$_2$H$_5$ | 4-CH(OCH$_3$)$_2$ |
| CH$_3$ | C$_2$H$_5$ | 4-CH$_2$CN |
| CH$_3$ | C$_2$H$_5$ | 3-CHO |
| CH$_3$ | C$_2$H$_5$ | 4-CHO |
| CH$_3$ | C$_2$H$_5$ | 3-CO—CH$_3$ |
| CH$_3$ | C$_2$H$_5$ | 4-CO—CH$_3$ |
| CH$_3$ | C$_2$H$_5$ | 3-COOH |
| CH$_3$ | C$_2$H$_5$ | 4-COOH |
| CH$_3$ | C$_2$H$_5$ | 3-COOCH$_3$ |
| CH$_3$ | C$_2$H$_5$ | 4-COOCH$_3$ |
| CH$_3$ | C$_2$H$_5$ | 3-COOC$_2$H$_5$ |
| CH$_3$ | C$_2$H$_5$ | 4-COOC$_2$H$_5$ |
| CH$_3$ | C$_2$H$_5$ | 3-COO-i-C$_3$H$_7$ |
| CH$_3$ | C$_2$H$_5$ | 4-COO-i-C$_3$H$_7$ |
| CH$_3$ | C$_2$H$_5$ | 3-COO-t-C$_4$H$_9$ |
| CH$_3$ | C$_2$H$_5$ | 4-COO-t-C$_4$H$_9$ |
| CH$_3$ | C$_2$H$_5$ | 3-COO-n-C$_6$H$_{13}$ |
| CH$_3$ | C$_2$H$_5$ | 4-COO-n-C$_6$H$_{13}$ |
| CH$_3$ | C$_2$H$_5$ | 3-CONH$_2$ |
| CH$_3$ | C$_2$H$_5$ | 4-CONH$_2$ |
| CH$_3$ | C$_2$H$_5$ | 3-CONHCH$_3$ |
| CH$_3$ | C$_2$H$_5$ | 4-CONHCH$_3$ |
| CH$_3$ | C$_2$H$_5$ | 3-CON(CH$_3$)$_2$ |
| CH$_3$ | C$_2$H$_5$ | 4-CON(CH$_3$)$_2$ |
| CH$_3$ | C$_2$H$_5$ | 3-CSNH$_2$ |
| CH$_3$ | C$_2$H$_5$ | 4-CSNH$_2$ |
| CH$_3$ | C$_2$H$_5$ | 3-NH$_2$ |
| CH$_3$ | C$_2$H$_5$ | 4-NH$_2$ |
| CH$_3$ | C$_2$H$_5$ | 4-NHCH$_3$ |
| CH$_3$ | C$_2$H$_5$ | 4-N(CH$_3$)$_2$ |
| CH$_3$ | C$_2$H$_5$ | 3-NHCO—CH$_3$ |
| CH$_3$ | C$_2$H$_5$ | 4-NHCO—CH$_3$ |
| CH$_3$ | C$_2$H$_5$ | 4-NCH$_3$—CO—CH$_3$ |
| CH$_3$ | C$_2$H$_5$ | 4-NHCOOCH$_3$ |
| CH$_3$ | C$_2$H$_5$ | 4-NCH$_3$—COOCH$_3$ |
| CH$_3$ | C$_2$H$_5$ | 3-OCO—CH$_3$ |
| CH$_3$ | C$_2$H$_5$ | 4-OCO—CH$_3$ |
| CH$_3$ | C$_2$H$_5$ | 4-OCO-t-C$_4$H$_9$ |
| CH$_3$ | C$_2$H$_5$ | 4-SH |
| CH$_3$ | C$_2$H$_5$ | 4-SCH$_3$ |
| CH$_3$ | C$_2$H$_5$ | 4-S-t-C$_4$H$_9$ |
| CH$_3$ | C$_2$H$_5$ | 4-SO—CH$_3$ |
| CH$_3$ | C$_2$H$_5$ | 4-SO$_2$—CH$_3$ |
| CH$_3$ | C$_2$H$_5$ | 4-C(CH$_3$)=NCH$_3$ |
| CH$_3$ | C$_2$H$_5$ | 4-C(SCH$_3$)=NOCH$_3$ |
| CH$_3$ | C$_2$H$_5$ | 4-C(OCH$_3$)=NOCH$_3$ |
| CH$_3$ | C$_2$H$_5$ | 3-CH=NOCH$_3$ |
| CH$_3$ | C$_2$H$_5$ | 4-CH=NOCH$_3$ |
| CH$_3$ | C$_2$H$_5$ | 3-C(CH$_3$)=NOCH$_3$ |
| CH$_3$ | C$_2$H$_5$ | 4-C(CH$_3$)=NOCH$_3$ |
| CH$_3$ | C$_2$H$_5$ | 4-C(CH$_3$)=NOC$_2$H$_5$ |
| CH$_3$ | C$_2$H$_5$ | 4-C(CH$_3$)=NO-n-C$_3$H$_7$ |
| CH$_3$ | C$_2$H$_5$ | 4-C(CH$_3$)=NO-i-C$_3$H$_7$ |
| CH$_3$ | C$_2$H$_5$ | 4-C(CH$_3$)=NO-n-C$_4$H$_9$ |
| CH$_3$ | C$_2$H$_5$ | 4-C(CH$_3$)=NO-t-C$_4$H$_9$ |
| CH$_3$ | C$_2$H$_5$ | 4-C(CH$_3$)=NO-n-C$_5$H$_{11}$ |
| CH$_3$ | C$_2$H$_5$ | 4-C(CH$_3$)=NO-n-C$_6$H$_{13}$ |
| CH$_3$ | C$_2$H$_5$ | 2-Cl, 4-CH$_3$ |

TABLE A-continued

| R | A | Q_m |
|---|---|---|
| CH$_3$ | C$_2$H$_5$ | 3-Cl, 5-CH$_3$ |
| CH$_3$ | C$_2$H$_5$ | 2-CH$_3$, 4-Cl |
| CH$_3$ | C$_2$H$_5$ | 3-CH$_3$, 4-Cl |
| CH$_3$ | C$_2$H$_5$ | 3-F, 5-CH$_3$ |
| CH$_3$ | C$_2$H$_5$ | 3-Br, 5-CH$_3$ |
| CH$_3$ | C$_2$H$_5$ | 3-Cl, 5-NO$_2$ |
| CH$_3$ | C$_2$H$_5$ | 3-NO$_2$, 4-Cl |
| CH$_3$ | C$_2$H$_5$ | 3-Cl, 4-OCH$_3$ |
| CH$_3$ | C$_2$H$_5$ | 3-OCH$_3$, 4-Cl |
| CH$_3$ | C$_2$H$_5$ | 3-Cl, 5-CF$_3$ |
| CH$_3$ | C$_2$H$_5$ | 3-Cl, 5-OCF$_3$ |
| CH$_3$ | C$_2$H$_5$ | 3-F, 5-CF$_3$ |
| CH$_3$ | C$_2$H$_5$ | 2-CH$_3$, 4-CN |
| CH$_3$ | C$_2$H$_5$ | 2-CH$_3$, 4-OCH$_3$ |
| CH$_3$ | C$_2$H$_5$ | 2-CH$_3$, 4-CF$_3$ |
| CH$_3$ | C$_2$H$_5$ | 2-CH$_3$, 4-C(CH$_3$)=NOCH$_3$ |
| CH$_3$ | C$_2$H$_5$ | 3-CH$_3$, 4-C(CH$_3$)=NOCH$_3$ |
| CH$_3$ | C$_2$H$_5$ | 2-OH, 5-CH$_3$ |
| CH$_3$ | C$_2$H$_5$ | 3-CH$_3$, 4-O-t-C$_4$H$_9$ |
| CH$_3$ | C$_2$H$_5$ | 2-C(COOCH$_3$)=NOCH$_3$ |
| CH$_3$ | C$_2$H$_5$ | 2,3-Butadienyl |
| CH$_3$ | C$_2$H$_5$ | 3,4-Butadienyl |
| H | CH(CH$_3$)$_2$ | H |
| H | CH(CH$_3$)$_2$ | 2-F |
| H | CH(CH$_3$)$_2$ | 3-F |
| H | CH(CH$_3$)$_2$ | 4-F |
| H | CH(CH$_3$)$_2$ | 2,3-F$_2$ |
| H | CH(CH$_3$)$_2$ | 2,4-F$_2$ |
| H | CH(CH$_3$)$_2$ | 2,5-F$_2$ |
| H | CH(CH$_3$)$_2$ | 2,6-F$_2$ |
| H | CH(CH$_3$)$_2$ | 3,4-F$_2$ |
| H | CH(CH$_3$)$_2$ | 3,5-F$_2$ |
| H | CH(CH$_3$)$_2$ | 2-Cl |
| H | CH(CH$_3$)$_2$ | 3-Cl |
| H | CH(CH$_3$)$_2$ | 4-Cl |
| H | CH(CH$_3$)$_2$ | 2,4-Cl$_2$ |
| H | CH(CH$_3$)$_2$ | 2,5-Cl$_2$ |
| H | CH(CH$_3$)$_2$ | 3,4-Cl$_2$ |
| H | CH(CH$_3$)$_2$ | 3,5-Cl$_2$ |
| H | CH(CH$_3$)$_2$ | 2-Br |
| H | CH(CH$_3$)$_2$ | 3-Br |
| H | CH(CH$_3$)$_2$ | 4-Br |
| H | CH(CH$_3$)$_2$ | 2,4-Br$_2$ |
| H | CH(CH$_3$)$_2$ | 3,4-Br$_2$ |
| H | CH(CH$_3$)$_2$ | 3,5-Br$_2$ |
| H | CH(CH$_3$)$_2$ | 2-I |
| H | CH(CH$_3$)$_2$ | 3-I |
| H | CH(CH$_3$)$_2$ | 4-I |
| H | CH(CH$_3$)$_2$ | 2-F, 4-Cl |
| H | CH(CH$_3$)$_2$ | 2-F, 5-Cl |
| H | CH(CH$_3$)$_2$ | 2-F, 4-Br |
| H | CH(CH$_3$)$_2$ | 2-F, 5-Br |
| H | CH(CH$_3$)$_2$ | 2-Cl, 4-Br |
| H | CH(CH$_3$)$_2$ | 2-Cl, 5-Br |
| H | CH(CH$_3$)$_2$ | 3-F, 4-Cl |
| H | CH(CH$_3$)$_2$ | 3-F, 5-Cl |
| H | CH(CH$_3$)$_2$ | 3-F, 4-Br |
| H | CH(CH$_3$)$_2$ | 3-F, 5-Br |
| H | CH(CH$_3$)$_2$ | 3-Cl, 4-Br |
| H | CH(CH$_3$)$_2$ | 3-Cl, 5-Br |
| H | CH(CH$_3$)$_2$ | 3-Cl, 4-F |
| H | CH(CH$_3$)$_2$ | 3-Br, 4-F |
| H | CH(CH$_3$)$_2$ | 3-Br, 4-Cl |
| H | CH(CH$_3$)$_2$ | 2-NO$_2$ |
| H | CH(CH$_3$)$_2$ | 3-NO$_2$ |
| H | CH(CH$_3$)$_2$ | 4-NO$_2$ |
| H | CH(CH$_3$)$_2$ | 2-CN |
| H | CH(CH$_3$)$_2$ | 3-CN |
| H | CH(CH$_3$)$_2$ | 4-CN |
| H | CH(CH$_3$)$_2$ | 2-CH$_3$ |
| H | CH(CH$_3$)$_2$ | 3-CH$_3$ |
| H | CH(CH$_3$)$_2$ | 4-CH$_3$ |
| H | CH(CH$_3$)$_2$ | 2,3-(CH$_3$)$_2$ |
| H | CH(CH$_3$)$_2$ | 2,4-(CH$_3$)$_2$ |
| H | CH(CH$_3$)$_2$ | 2,5-(CH$_3$)$_2$ |
| H | CH(CH$_3$)$_2$ | 2,6-(CH$_3$)$_2$ |
| H | CH(CH$_3$)$_2$ | 3,4-(CH$_3$)$_2$ |
| H | CH(CH$_3$)$_2$ | 3,5-(CH$_3$)$_2$ |
| H | CH(CH$_3$)$_2$ | 2,4,5-(CH$_3$)$_3$ |
| H | CH(CH$_3$)$_2$ | 2,4,6-(CH$_3$)$_3$ |
| H | CH(CH$_3$)$_2$ | 3,4,5-(CH$_3$)$_3$ |
| H | CH(CH$_3$)$_2$ | 2-C$_2$H$_5$ |
| H | CH(CH$_3$)$_2$ | 3-C$_2$H$_5$ |
| H | CH(CH$_3$)$_2$ | 4-C$_2$H$_5$ |
| H | CH(CH$_3$)$_2$ | 3,4-(C$_2$H$_5$)$_2$ |
| H | CH(CH$_3$)$_2$ | 3,5-(C$_2$H$_5$)$_2$ |
| H | CH(CH$_3$)$_2$ | 3-n-C$_3$H$_7$ |
| H | CH(CH$_3$)$_2$ | 4-n-C$_3$H$_7$ |
| H | CH(CH$_3$)$_2$ | 3,4-(n-C$_3$H$_7$)$_2$ |
| H | CH(CH$_3$)$_2$ | 3,5-(n-C$_3$H$_7$)$_2$ |
| H | CH(CH$_3$)$_2$ | 3-i-C$_3$H$_7$ |
| H | CH(CH$_3$)$_2$ | 4-i-C$_3$H$_7$ |
| H | CH(CH$_3$)$_2$ | 3,4-(i-C$_3$H$_7$)$_2$ |
| H | CH(CH$_3$)$_2$ | 3,5-(i-C$_3$H$_7$)$_2$ |
| H | CH(CH$_3$)$_2$ | 3-Cyclopropyl |
| H | CH(CH$_3$)$_2$ | 4-Cyclopropyl |
| H | CH(CH$_3$)$_2$ | 3-n-C$_4$H$_9$ |
| H | CH(CH$_3$)$_2$ | 4-n-C$_4$H$_9$ |
| H | CH(CH$_3$)$_2$ | 3,4-(n-C$_4$H$_9$)$_2$ |
| H | CH(CH$_3$)$_2$ | 3,5-(n-C$_4$H$_9$)$_2$ |
| H | CH(CH$_3$)$_2$ | 3-s-C$_4$H$_9$ |
| H | CH(CH$_3$)$_2$ | 4-s-C$_4$H$_9$ |
| H | CH(CH$_3$)$_2$ | 3-i-C$_4$H$_9$ |
| H | CH(CH$_3$)$_2$ | 4-i-C$_4$H$_9$ |
| H | CH(CH$_3$)$_2$ | 3-t-C$_4$H$_9$ |
| H | CH(CH$_3$)$_2$ | 4-t-C$_4$H$_9$ |
| H | CH(CH$_3$)$_2$ | 3,4-(t-C$_4$H$_9$)$_2$ |
| H | CH(CH$_3$)$_2$ | 3,5-(t-C$_4$H$_9$)$_2$ |
| H | CH(CH$_3$)$_2$ | 3-n-C$_5$H$_{11}$ |
| H | CH(CH$_3$)$_2$ | 4-n-C$_5$H$_{11}$ |
| H | CH(CH$_3$)$_2$ | 3-n-C$_6$H$_{13}$ |
| H | CH(CH$_3$)$_2$ | 4-n-C$_6$H$_{13}$ |
| H | CH(CH$_3$)$_2$ | 3-Cyclohexyl |
| H | CH(CH$_3$)$_2$ | 4-Cyclohexyl |
| H | CH(CH$_3$)$_2$ | 3-Phenyl |
| H | CH(CH$_3$)$_2$ | 4-Phenyl |
| H | CH(CH$_3$)$_2$ | 3-Vinyl |
| H | CH(CH$_3$)$_2$ | 4-Vinyl |
| H | CH(CH$_3$)$_2$ | 3-Allyl |
| H | CH(CH$_3$)$_2$ | 4-Allyl |
| H | CH(CH$_3$)$_2$ | 3-Propargyl |
| H | CH(CH$_3$)$_2$ | 4-Propargyl |
| H | CH(CH$_3$)$_2$ | 3-(Propen-2-yl) |
| H | CH(CH$_3$)$_2$ | 4-(Propen-2-yl) |
| H | CH(CH$_3$)$_2$ | 2-CH$_3$, 4-C$_2$H$_5$ |
| H | CH(CH$_3$)$_2$ | 2-CH$_3$, 5-C$_2$H$_5$ |
| H | CH(CH$_3$)$_2$ | 2-CH$_3$—, 4-n-C$_3$H$_7$ |
| H | CH(CH$_3$)$_2$ | 2-CH$_3$, 5-n-C$_3$H$_7$ |
| H | CH(CH$_3$)$_2$ | 2-CH$_3$, 4-i-C$_3$H$_7$ |
| H | CH(CH$_3$)$_2$ | 2-CH$_3$, 5-i-C$_3$H$_7$ |
| H | CH(CH$_3$)$_2$ | 2-CH$_3$, 4-n-C$_4$H$_9$ |
| H | CH(CH$_3$)$_2$ | 2-CH$_3$, 4-s-C$_4$H$_9$ |
| H | CH(CH$_3$)$_2$ | 2-CH$_3$, 4-i-C$_4$H$_9$ |
| H | CH(CH$_3$)$_2$ | 2-CH$_3$, 4-t-C$_4$H$_9$ |
| H | CH(CH$_3$)$_2$ | 2-CH$_3$, 4-phenyl |
| H | CH(CH$_3$)$_2$ | 2-CH$_3$, 5-phenyl |
| H | CH(CH$_3$)$_2$ | 2-CH$_3$, 4-vinyl |
| H | CH(CH$_3$)$_2$ | 2-CH$_3$, 4-allyl |
| H | CH(CH$_3$)$_2$ | 2-CH$_3$, 4-propargyl |
| H | CH(CH$_3$)$_2$ | 2-CH$_3$, 4-(propen-2-yl) |
| H | CH(CH$_3$)$_2$ | 3-CH$_3$, 4-C$_2$H$_5$ |
| H | CH(CH$_3$)$_2$ | 3-CH$_3$, 5-C$_2$H$_5$ |
| H | CH(CH$_3$)$_2$ | 3-CH$_3$, 4-n-C$_3$H$_7$ |
| H | CH(CH$_3$)$_2$ | 3-CH$_3$, 5-n-C$_3$H$_7$ |
| H | CH(CH$_3$)$_2$ | 3-CH$_3$, 4-i-C$_3$H$_7$ |
| H | CH(CH$_3$)$_2$ | 3-CH$_3$, 5-i-C$_3$H$_7$ |
| H | CH(CH$_3$)$_2$ | 3-CH$_3$, 4-cyclopropyl |
| H | CH(CH$_3$)$_2$ | 3-CH$_3$, 4-t-C$_4$H$_9$ |
| H | CH(CH$_3$)$_2$ | 3-CH$_3$, 5-t-C$_4$H$_9$ |
| H | CH(CH$_3$)$_2$ | 3-CH$_3$, 4-phenyl |
| H | CH(CH$_3$)$_2$ | 3-CH$_3$, 5-phenyl |
| H | CH(CH$_3$)$_2$ | 3-CH$_3$, 4-vinyl |
| H | CH(CH$_3$)$_2$ | 3-CH$_3$, 4-allyl |
| H | CH(CH$_3$)$_2$ | 3-CH$_3$, 4-propargyl |

TABLE A-continued

| R | A | $Q_m$ |
|---|---|---|
| H | $CH(CH_3)_2$ | 3-$CH_3$, 4-propen-2-yl |
| H | $CH(CH_3)_2$ | 3-$C_2H_5$, 4-$CH_3$ |
| H | $CH(CH_3)_2$ | 3-i-$C_3H_7$, 4-$CH_3$ |
| H | $CH(CH_3)_2$ | 3-t-$C_4H_9$, 4-$CH_3$ |
| H | $CH(CH_3)_2$ | 3-Phenyl, 4-$CH_3$ |
| H | $CH(CH_3)_2$ | 2-OH |
| H | $CH(CH_3)_2$ | 3-OH |
| H | $CH(CH_3)_2$ | 4-OH |
| H | $CH(CH_3)_2$ | 2-$OCH_3$ |
| H | $CH(CH_3)_2$ | 3-$OCH_3$ |
| H | $CH(CH_3)_2$ | 4-$OCH_3$ |
| H | $CH(CH_3)_2$ | 2,3-$(OCH_3)_2$ |
| H | $CH(CH_3)_2$ | 2,4-$(OCH_3)_2$ |
| H | $CH(CH_3)_2$ | 2,5-$(OCH_3)_2$ |
| H | $CH(CH_3)_2$ | 3,4-$(OCH_3)_2$ |
| H | $CH(CH_3)_2$ | 3,5-$(OCH_3)_2$ |
| H | $CH(CH_3)_2$ | 3,4,5-$(OCH_3)_3$ |
| H | $CH(CH_3)_2$ | 3-$OC_2H_5$ |
| H | $CH(CH_3)_2$ | 4-$OC_2H_5$ |
| H | $CH(CH_3)_2$ | 3,4-$(OC_2H_5)_2$ |
| H | $CH(CH_3)_2$ | 3,5-$(OC_2H_5)_2$ |
| H | $CH(CH_3)_2$ | 3-O-n-$C_3H_7$ |
| H | $CH(CH_3)_2$ | 4-O-n-$C_3H_7$ |
| H | $CH(CH_3)_2$ | 3-O-i-$C_3H_7$ |
| H | $CH(CH_3)_2$ | 4-O-i-$C_3H_7$ |
| H | $CH(CH_3)_2$ | 3-O-Cyclopropyl |
| H | $CH(CH_3)_2$ | 4-O-Cyclopropyl |
| H | $CH(CH_3)_2$ | 3-O-n-$C_4H_9$ |
| H | $CH(CH_3)_2$ | 4-O-n-$C_4H_9$ |
| H | $CH(CH_3)_2$ | 3-O-s-$C_4H_9$ |
| H | $CH(CH_3)_2$ | 4-O-s-$C_4H_9$ |
| H | $CH(CH_3)_2$ | 3-O-i-$C_4H_9$ |
| H | $CH(CH_3)_2$ | 4-O-i-$C_4H_9$ |
| H | $CH(CH_3)_2$ | 3-O-t-$C_4H_9$ |
| H | $CH(CH_3)_2$ | 4-O-t-$C_4H_9$ |
| H | $CH(CH_3)_2$ | 3-O-n-$C_5H_{11}$ |
| H | $CH(CH_3)_2$ | 4-O-n-$C_5H_{11}$ |
| H | $CH(CH_3)_2$ | 3-O-n-$C_6H_{13}$ |
| H | $CH(CH_3)_2$ | 4-O-n-$C_6H_{13}$ |
| H | $CH(CH_3)_2$ | 3-O-Cyclohexyl |
| H | $CH(CH_3)_2$ | 4-O-Cyclohexyl |
| H | $CH(CH_3)_2$ | 3-O-Phenyl |
| H | $CH(CH_3)_2$ | 4-O-Phenyl |
| H | $CH(CH_3)_2$ | 3-O-Allyl |
| H | $CH(CH_3)_2$ | 4-O-Allyl |
| H | $CH(CH_3)_2$ | 2-$CF_3$ |
| H | $CH(CH_3)_2$ | 3-$CF_3$ |
| H | $CH(CH_3)_2$ | 4-$CF_3$ |
| H | $CH(CH_3)_2$ | 2,4-$(CF_3)_2$ |
| H | $CH(CH_3)_2$ | 3,5-$(CF_3)_2$ |
| H | $CH(CH_3)_2$ | 3-$CF_2Cl$ |
| H | $CH(CH_3)_2$ | 4-$CF_2Cl$ |
| H | $CH(CH_3)_2$ | 3-$CFCl_2$ |
| H | $CH(CH_3)_2$ | 4-$CFCl_2$ |
| H | $CH(CH_3)_2$ | 3-$CCl_3$ |
| H | $CH(CH_3)_2$ | 4-$CCl_3$ |
| H | $CH(CH_3)_2$ | 3-$CH_2CH_2F$ |
| H | $CH(CH_3)_2$ | 4-$CH_2CH_2F$ |
| H | $CH(CH_3)_2$ | 3-$CH_2CF_3$ |
| H | $CH(CH_3)_2$ | 4-$CH_2CF_3$ |
| H | $CH(CH_3)_2$ | 3-$C_2F_5$ |
| H | $CH(CH_3)_2$ | 4-$C_2F_5$ |
| H | $CH(CH_3)_2$ | 3-$CHCl_2$ |
| H | $CH(CH_3)_2$ | 4-$CHCl_2$ |
| H | $CH(CH_3)_2$ | 3-$CH_2Cl$ |
| H | $CH(CH_3)_2$ | 4-$CH_2Cl$ |
| H | $CH(CH_3)_2$ | 3-$CF_2CHF_2$ |
| H | $CH(CH_3)_2$ | 4-$CF_2CHF_2$ |
| H | $CH(CH_3)_2$ | 3-$CH_2CH_2Cl$ |
| H | $CH(CH_3)_2$ | 4-$CH_2CH_2Cl$ |
| H | $CH(CH_3)_2$ | 2-$OCF_3$ |
| H | $CH(CH_3)_2$ | 3-$OCF_3$ |
| H | $CH(CH_3)_2$ | 4-$OCF_3$ |
| H | $CH(CH_3)_2$ | 3-$OCHF_2$ |
| H | $CH(CH_3)_2$ | 4-$OCHF_2$ |
| H | $CH(CH_3)_2$ | 3-$OC_2F_5$ |
| H | $CH(CH_3)_2$ | 4-$OC_2F_5$ |
| H | $CH(CH_3)_2$ | 3-$OCF_2CHF_2$ |
| H | $CH(CH_3)_2$ | 4-$OCF_2CHF_2$ |
| H | $CH(CH_3)_2$ | 3-$CH_2OCH_3$ |
| H | $CH(CH_3)_2$ | 4-$CH_2OCH_3$ |
| H | $CH(CH_3)_2$ | 3-$CH_2$-O-t-$C_4H_9$ |
| H | $CH(CH_3)_2$ | 4-$CH_2$-O-t-$C_4H_9$ |
| H | $CH(CH_3)_2$ | 3-$C(CH_3)(OCH_3)_2$ |
| H | $CH(CH_3)_2$ | 4-$C(CH_3)(OCH_3)_2$ |
| H | $CH(CH_3)_2$ | 3-$CH(OCH_3)_2$ |
| H | $CH(CH_3)_2$ | 4-$CH(OCH_3)_2$ |
| H | $CH(CH_3)_2$ | 3-$CH_2CN$ |
| H | $CH(CH_3)_2$ | 4-$CH_2CN$ |
| H | $CH(CH_3)_2$ | 3-CHO |
| H | $CH(CH_3)_2$ | 4-CHO |
| H | $CH(CH_3)_2$ | 3-CO—$CH_3$ |
| H | $CH(CH_3)_2$ | 4-CO—$CH_3$ |
| H | $CH(CH_3)_2$ | 3-CO—$C_2H_5$ |
| H | $CH(CH_3)_2$ | 4-CO—$C_2H_5$ |
| H | $CH(CH_3)_2$ | 2-COOH |
| H | $CH(CH_3)_2$ | 3-COOH |
| H | $CH(CH_3)_2$ | 4-COOH |
| H | $CH(CH_3)_2$ | 3-$COOCH_3$ |
| H | $CH(CH_3)_2$ | 4-$COOCH_3$ |
| H | $CH(CH_3)_2$ | 3-$COOC_2H_5$ |
| H | $CH(CH_3)_2$ | 4-$COOC_2H_5$ |
| H | $CH(CH_3)_2$ | 3-COO-n-$C_3H_7$ |
| H | $CH(CH_3)_2$ | 4-COO-n-$C_3H_7$ |
| H | $CH(CH_3)_2$ | 3-COO-i-$C_3H_7$ |
| H | $CH(CH_3)_2$ | 4-COO-i-$C_3H_7$ |
| H | $CH(CH_3)_2$ | 3-COO-n-$C_4H_9$ |
| H | $CH(CH_3)_2$ | 4-COO-n-$C_4H_9$ |
| H | $CH(CH_3)_2$ | 3-COO-s-$C_4H_9$ |
| H | $CH(CH_3)_2$ | 4-COO-s-$C_4H_9$ |
| H | $CH(CH_3)_2$ | 3-COO-i-$C_4H_9$ |
| H | $CH(CH_3)_2$ | 4-COO-i-$C_4H_9$ |
| H | $CH(CH_3)_2$ | 3-COO-t-$C_4H_9$ |
| H | $CH(CH_3)_2$ | 4-COO-t-$C_4H_9$ |
| H | $CH(CH_3)_2$ | 3-COO-n-$C_5H_{11}$ |
| H | $CH(CH_3)_2$ | 4-COO-n-$C_5H_{11}$ |
| H | $CH(CH_3)_2$ | 3-COO-n-$C_6H_{13}$ |
| H | $CH(CH_3)_2$ | 4-COO-n-$C_6H_{13}$ |
| H | $CH(CH_3)_2$ | 2-$CONH_2$ |
| H | $CH(CH_3)_2$ | 3-$CONH_2$ |
| H | $CH(CH_3)_2$ | 4-$CONH_2$ |
| H | $CH(CH_3)_2$ | 3-$CONHCH_3$ |
| H | $CH(CH_3)_2$ | 4-$CONHCH_3$ |
| H | $CH(CH_3)_2$ | 3-$CON(CH_3)_2$ |
| H | $CH(CH_3)_2$ | 4-$CON(CH_3)_2$ |
| H | $CH(CH_3)_2$ | 3-$CON(C_2H_5)_2$ |
| H | $CH(CH_3)_2$ | 4-$CON(C_2H_5)_2$ |
| H | $CH(CH_3)_2$ | 2-$CSNH_2$ |
| H | $CH(CH_3)_2$ | 3-$CSNH_2$ |
| H | $CH(CH_3)_2$ | 4-$CSNH_2$ |
| H | $CH(CH_3)_2$ | 2-$NH_2$ |
| H | $CH(CH_3)_2$ | 3-$NH_2$ |
| H | $CH(CH_3)_2$ | 4-$NH_2$ |
| H | $CH(CH_3)_2$ | 3-$NHCH_3$ |
| H | $CH(CH_3)_2$ | 4-$NHCH_3$ |
| H | $CH(CH_3)_2$ | 3-$N(CH_3)_2$ |
| H | $CH(CH_3)_2$ | 4-$N(CH_3)_2$ |
| H | $CH(CH_3)_2$ | 3-NHCO—$CH_3$ |
| H | $CH(CH_3)_2$ | 4-NHCO—$CH_3$ |
| H | $CH(CH_3)_2$ | 3-$NCH_3$—CO—$CH_3$ |
| H | $CH(CH_3)_2$ | 4-$NCH_3$—CO—$CH_3$ |
| H | $CH(CH_3)_2$ | 3-$NHCOOCH_3$ |
| H | $CH(CH_3)_2$ | 4-$NHCOOCH_3$ |
| H | $CH(CH_3)_2$ | 3-$NCH_3$—$COOCH_3$ |
| H | $CH(CH_3)_2$ | 4-$NCH_3$—$COOCH_3$ |
| H | $CH(CH_3)_2$ | 3-OCO—$CH_3$ |
| H | $CH(CH_3)_2$ | 4-OCO—$CH_3$ |
| H | $CH(CH_3)_2$ | 3-OCO-t-$C_4H_9$ |
| H | $CH(CH_3)_2$ | 4-OCO-t-$C_4H_9$ |
| H | $CH(CH_3)_2$ | 3-SH |
| H | $CH(CH_3)_2$ | 4-SH |
| H | $CH(CH_3)_2$ | 3-$SCH_3$ |
| H | $CH(CH_3)_2$ | 4-$SCH_3$ |
| H | $CH(CH_3)_2$ | 3-S-t-$C_4H_9$ |

TABLE A-continued

| R | A | Q_m |
|---|---|---|
| H | CH(CH$_3$)$_2$ | 4-S-t-C$_4$H$_9$ |
| H | CH(CH$_3$)$_2$ | 3-SO—CH$_3$ |
| H | CH(CH$_3$)$_2$ | 4-SO—CH$_3$ |
| H | CH(CH$_3$)$_2$ | 3-SO$_2$CH$_3$ |
| H | CH(CH$_3$)$_2$ | 4-SO$_2$CH$_3$ |
| H | CH(CH$_3$)$_2$ | 3-CH=NCH$_3$ |
| H | CH(CH$_3$)$_2$ | 4-CH=NCH$_3$ |
| H | CH(CH$_3$)$_2$ | 3-C(CH$_3$)=NCH$_3$ |
| H | CH(CH$_3$)$_2$ | 4-C(CH$_3$)=NCH$_3$ |
| H | CH(CH$_3$)$_2$ | 3-C(SCH$_3$)=NOCH$_3$ |
| H | CH(CH$_3$)$_2$ | 4-C(SCH$_3$)=NOCH$_3$ |
| H | CH(CH$_3$)$_2$ | 3-C(OCH$_3$)=NOCH$_3$ |
| H | CH(CH$_3$)$_2$ | 4-C(OCH$_3$)=NOCH$_3$ |
| H | CH(CH$_3$)$_2$ | 3-C(NH$_2$)=NOCH$_3$ |
| H | CH(CH$_3$)$_2$ | 4-C(NH$_2$)=NOCH$_3$ |
| H | CH(CH$_3$)$_2$ | 3-C(NHCH$_3$)=NOCH$_3$ |
| H | CH(CH$_3$)$_2$ | 4-C(NHCH$_3$)=NOCH$_3$ |
| H | CH(CH$_3$)$_2$ | 3-CH=NOCH$_3$ |
| H | CH(CH$_3$)$_2$ | 4-CH=NOCH$_3$ |
| H | CH(CH$_3$)$_2$ | 3-C(CH$_3$)=NOCH$_3$ |
| H | CH(CH$_3$)$_2$ | 4-C(CH$_3$)=NOCH$_3$ |
| H | CH(CH$_3$)$_2$ | 3-C(CH$_3$)=NOC$_2$H$_5$ |
| H | CH(CH$_3$)$_2$ | 4-C(CH$_3$)=NOC$_2$H$_5$ |
| H | CH(CH$_3$)$_2$ | 3-C(CH$_3$)=NO-n-C$_3$H$_7$ |
| H | CH(CH$_3$)$_2$ | 4-C(CH$_3$)=NO-n-C$_3$H$_7$ |
| H | CH(CH$_3$)$_2$ | 3-C(CH$_3$)=NO-i-C$_3$H$_7$ |
| H | CH(CH$_3$)$_2$ | 4-C(CH$_3$)=NO-i-C$_3$H$_7$ |
| H | CH(CH$_3$)$_2$ | 3-C(CH$_3$)=NO-n-C$_4$H$_9$ |
| H | CH(CH$_3$)$_2$ | 4-C(CH$_3$)=NO-n-C$_4$H$_9$ |
| H | CH(CH$_3$)$_2$ | 3-C(CH$_3$)=NO-s-C$_4$H$_9$ |
| H | CH(CH$_3$)$_2$ | 4-C(CH$_3$)=NO-s-C$_4$H$_9$ |
| H | CH(CH$_3$)$_2$ | 3-C(CH$_3$)=NO-i-C$_4$H$_9$ |
| H | CH(CH$_3$)$_2$ | 4-C(CH$_3$)=NO-i-C$_4$H$_9$ |
| H | CH(CH$_3$)$_2$ | 3-C(CH$_3$)=NO-t-C$_4$H$_9$ |
| H | CH(CH$_3$)$_2$ | 4-C(CH$_3$)=NO-t-C$_4$H$_9$ |
| H | CH(CH$_3$)$_2$ | 3-C(CH$_3$)=NO-n-C$_5$H$_{11}$ |
| H | CH(CH$_3$)$_2$ | 4-C(CH$_3$)=NO-n-C$_5$H$_{11}$ |
| H | CH(CH$_3$)$_2$ | 3-C(CH$_3$)=NO-n-C$_6$H$_{13}$ |
| H | CH(CH$_3$)$_2$ | 4-C(CH$_3$)=NO-n-C$_6$H$_{13}$ |
| H | CH(CH$_3$)$_2$ | 2-Cl, 4-CH$_3$ |
| H | CH(CH$_3$)$_2$ | 2-Cl, 5-CH$_3$ |
| H | CH(CH$_3$)$_2$ | 3-Cl, 4-CH$_3$ |
| H | CH(CH$_3$)$_2$ | 3-Cl, 5-CH$_3$ |
| H | CH(CH$_3$)$_2$ | 2-CH$_3$, 4-Cl |
| H | CH(CH$_3$)$_2$ | 2-CH$_3$, 5-Cl |
| H | CH(CH$_3$)$_2$ | 3-CH$_3$, 4-Cl |
| H | CH(CH$_3$)$_2$ | 3-Cl, 5-t-C$_4$H$_9$ |
| H | CH(CH$_3$)$_2$ | 2-Cl, 4-t-C$_4$H$_9$ |
| H | CH(CH$_3$)$_2$ | 2-F, 4-CH$_3$ |
| H | CH(CH$_3$)$_2$ | 3-F, 4-CH$_3$ |
| H | CH(CH$_3$)$_2$ | 3-F, 5-CH$_3$ |
| H | CH(CH$_3$)$_2$ | 2-CH$_3$, 4-F |
| H | CH(CH$_3$)$_2$ | 3-CH$_3$, 4-F |
| H | CH(CH$_3$)$_2$ | 2-F, 4-t-C$_4$H$_9$ |
| H | CH(CH$_3$)$_2$ | 3-F, 4-t-C$_4$H$_9$ |
| H | CH(CH$_3$)$_2$ | 2-F, 4-OCH$_3$ |
| H | CH(CH$_3$)$_2$ | 2-Br, 4-CH$_3$ |
| H | CH(CH$_3$)$_2$ | 3-Br, 4-CH$_3$ |
| H | CH(CH$_3$)$_2$ | 3-Br, 5-CH$_3$ |
| H | CH(CH$_3$)$_2$ | 2-CH$_3$, 4-Br |
| H | CH(CH$_3$)$_2$ | 3-CH$_3$, 4-Br |
| H | CH(CH$_3$)$_2$ | 2-Br, 4-t-C$_4$H$_9$ |
| H | CH(CH$_3$)$_2$ | 2-Cl, 4-NO$_2$ |
| H | CH(CH$_3$)$_2$ | 3-Cl, 4-NO$_2$ |
| H | CH(CH$_3$)$_2$ | 3-Cl, 5-NO$_2$ |
| H | CH(CH$_3$)$_2$ | 3-NO$_2$, 4-Cl |
| H | CH(CH$_3$)$_2$ | 3-Cl, 4-OCH |
| H | CH(CH$_3$)$_2$ | 3-OCH$_3$, 4-Cl |
| H | CH(CH$_3$)$_2$ | 2-Cl, 5-CF$_3$ |
| H | CH(CH$_3$)$_2$ | 3-Cl, 4-CF$_3$ |
| H | CH(CH$_3$)$_2$ | 3-Cl, 5-CF$_3$ |
| H | CH(CH$_3$)$_2$ | 3-CF$_3$, 4-Cl |
| H | CH(CH$_3$)$_2$ | 3-Cl, 5-OCF$_3$ |
| H | CH(CH$_3$)$_2$ | 3-F, 5-CF$_3$ |
| H | CH(CH$_3$)$_2$ | 2-CH$_3$, 4-CN |
| H | CH(CH$_3$)$_2$ | 3-NO$_2$, 4-CH$_3$ |
| H | CH(CH$_3$)$_2$ | 2-CH$_3$, 4-OCH$_3$ |
| H | CH(CH$_3$)$_2$ | 3-CH$_3$, 4-OCH$_3$ |
| H | CH(CH$_3$)$_2$ | 3-CH$_3$, 5-OCH$_3$ |
| H | CH(CH$_3$)$_2$ | 3-OCH$_3$, 4-CH$_3$ |
| H | CH(CH$_3$)$_2$ | 2-CH$_3$, 4-O-i-C$_3$H$_7$ |
| H | CH(CH$_3$)$_2$ | 3-CH$_3$, 4-O-i-C$_3$H$_7$ |
| H | CH(CH$_3$)$_2$ | 3-O-i-C$_3$H$_7$, 4-CH$_3$ |
| H | CH(CH$_3$)$_2$ | 2-CH$_3$, 4-CF$_3$ |
| H | CH(CH$_3$)$_2$ | 2-CH$_3$, 5-CF$_3$ |
| H | CH(CH$_3$)$_2$ | 3-CH$_3$, 4-CF$_3$ |
| H | CH(CH$_3$)$_2$ | 3-CH$_3$, 5-CF$_3$ |
| H | CH(CH$_3$)$_2$ | 3-CF$_3$, 4-CH$_3$ |
| H | CH(CH$_3$)$_2$ | 3-CF$_3$, 4-OCH$_3$ |
| H | CH(CH$_3$)$_2$ | 3-OCH$_3$, 4-CF$_3$ |
| H | CH(CH$_3$)$_2$ | 2-CH$_3$, 4-C(CH$_3$)=NOCH$_3$ |
| H | CH(CH$_3$)$_2$ | 3-CH$_3$, 4-C(CH$_3$)=NOCH$_3$ |
| H | CH(CH$_3$)$_2$ | 2-OH, 5-CH$_3$ |
| H | CH(CH$_3$)$_2$ | 3-CH$_3$, 4-OC$_2$H$_5$ |
| H | CH(CH$_3$)$_2$ | 3-CH$_3$, 4-O-t-C$_4$H$_9$ |
| H | CH(CH$_3$)$_2$ | 3-OC$_2$H$_5$, 4-CH$_3$ |
| H | CH(CH$_3$)$_2$ | 3-O-t-C$_4$H$_9$, 4-CH$_3$ |
| H | CH(CH$_3$)$_2$ | 2-C(COOCH$_3$)=NOCH$_3$ |
| H | CH(CH$_3$)$_2$ | 2,3-Butadienyl |
| H | CH(CH$_3$)$_2$ | 3,4-Butadienyl |
| CH$_3$ | CH(CH$_3$)$_2$ | H |
| CH$_3$ | CH(CH$_3$)$_2$ | 2-F |
| CH$_3$ | CH(CH$_3$)$_2$ | 3-F |
| CH$_3$ | CH(CH$_3$)$_2$ | 4-F |
| CH$_3$ | CH(CH$_3$)$_2$ | 2,4-F$_2$ |
| CH$_3$ | CH(CH$_3$)$_2$ | 3,4-F$_2$ |
| CH$_3$ | CH(CH$_3$)$_2$ | 3,5-F$_2$ |
| CH$_3$ | CH(CH$_3$)$_2$ | 2-Cl |
| CH$_3$ | CH(CH$_3$)$_2$ | 3-Cl |
| CH$_3$ | CH(CH$_3$)$_2$ | 4-Cl |
| CH$_3$ | CH(CH$_3$)$_2$ | 2,4-Cl$_2$ |
| CH$_3$ | CH(CH$_3$)$_2$ | 3,4-Cl$_2$ |
| CH$_3$ | CH(CH$_3$)$_2$ | 3,5-Cl$_2$ |
| CH$_3$ | CH(CH$_3$)$_2$ | 2-Br |
| CH$_3$ | CH(CH$_3$)$_2$ | 3-Br |
| CH$_3$ | CH(CH$_3$)$_2$ | 4-Br |
| CH$_3$ | CH(CH$_3$)$_2$ | 3,5-Br$_2$ |
| CH$_3$ | CH(CH$_3$)$_2$ | 3-I |
| CH$_3$ | CH(CH$_3$)$_2$ | 4-I |
| CH$_3$ | CH(CH$_3$)$_2$ | 3-F, 5-Cl |
| CH$_3$ | CH(CH$_3$)$_2$ | 3-F, 5-Br |
| CH$_3$ | CH(CH$_3$)$_2$ | 3-Cl, 5-Br |
| CH$_3$ | CH(CH$_3$)$_2$ | 3-Br, 4-F |
| CH$_3$ | CH(CH$_3$)$_2$ | 2-NO$_2$ |
| CH$_3$ | CH(CH$_3$)$_2$ | 3-NO$_2$ |
| CH$_3$ | CH(CH$_3$)$_2$ | 4-NO$_2$ |
| CH$_3$ | CH(CH$_3$)$_2$ | 2-CN |
| CH$_3$ | CH(CH$_3$)$_2$ | 3-CN |
| CH$_3$ | CH(CH$_3$)$_2$ | 4-CN |
| CH$_3$ | CH(CH$_3$)$_2$ | 2-CH$_3$ |
| CH$_3$ | CH(CH$_3$)$_2$ | 3-CH$_3$ |
| CH$_3$ | CH(CH$_3$)$_2$ | 4-CH$_3$ |
| CH$_3$ | CH(CH$_3$)$_2$ | 2,4-(CH$_3$)$_2$ |
| CH$_3$ | CH(CH$_3$)$_2$ | 2,5-(CH$_3$)$_2$ |
| CH$_3$ | CH(CH$_3$)$_2$ | 3,4-(CH$_3$)$_2$ |
| CH$_3$ | CH(CH$_3$)$_2$ | 3,5-(CH$_3$)$_2$ |
| CH$_3$ | CH(CH$_3$)$_2$ | 2,4,5-(CH$_3$)$_3$ |
| CH$_3$ | CH(CH$_3$)$_2$ | 2,4,6-(CH$_3$)$_3$ |
| CH$_3$ | CH(CH$_3$)$_2$ | 3-C$_2$H$_5$ |
| CH$_3$ | CH(CH$_3$)$_2$ | 4-C$_2$H$_5$ |
| CH$_3$ | CH(CH$_3$)$_2$ | 3,4-(C$_2$H$_5$)$_2$ |
| CH$_3$ | CH(CH$_3$)$_2$ | 3,5-(C$_2$H$_5$)$_2$ |
| CH$_3$ | CH(CH$_3$)$_2$ | 3-n-C$_3$H$_7$ |
| CH$_3$ | CH(CH$_3$)$_2$ | 4-n-C$_3$H$_7$ |
| CH$_3$ | CH(CH$_3$)$_2$ | 3-i-C$_3$H$_7$ |
| CH$_3$ | CH(CH$_3$)$_2$ | 4-i-C$_3$H$_7$ |
| CH$_3$ | CH(CH$_3$)$_2$ | 3-Cyclopropyl |
| CH$_3$ | CH(CH$_3$)$_2$ | 4-Cyclopropyl |
| CH$_3$ | CH(CH$_3$)$_2$ | 3-n-C$_4$H$_9$ |
| CH$_3$ | CH(CH$_3$)$_2$ | 4-n-C$_4$H$_9$ |
| CH$_3$ | CH(CH$_3$)$_2$ | 3-t-C$_4$H$_9$ |
| CH$_3$ | CH(CH$_3$)$_2$ | 4-t-C$_4$H$_9$ |
| CH$_3$ | CH(CH$_3$)$_2$ | 3-n-C$_6$H$_{13}$ |
| CH$_3$ | CH(CH$_3$)$_2$ | 4-n-C$_6$H$_{13}$ |

TABLE A-continued

| R | A | $Q_m$ |
|---|---|---|
| $CH_3$ | $CH(CH_3)_2$ | 3-Cyclohexyl |
| $CH_3$ | $CH(CH_3)_2$ | 4-Cyclohexyl |
| $CH_3$ | $CH(CH_3)_2$ | 3-Phenyl |
| $CH_3$ | $CH(CH_3)_2$ | 4-Phenyl |
| $CH_3$ | $CH(CH_3)_2$ | 4-Allyl |
| $CH_3$ | $CH(CH_3)_2$ | 4-Propargyl |
| $CH_3$ | $CH(CH_3)_2$ | 2-$CH_3$, 4-$C_2H_5$ |
| $CH_3$ | $CH(CH_3)_2$ | 2-$CH_3$, 4-i-$C_3H_7$ |
| $CH_3$ | $CH(CH_3)_2$ | 2-$CH_3$, 4-t-$C_4H_9$ |
| $CH_3$ | $CH(CH_3)_2$ | 2-$CH_3$, 4-phenyl |
| $CH_3$ | $CH(CH_3)_2$ | 3-$CH_3$, 4-phenyl |
| $CH_3$ | $CH(CH_3)_2$ | 3-OH |
| $CH_3$ | $CH(CH_3)_2$ | 4-OH |
| $CH_3$ | $CH(CH_3)_2$ | 3-$OCH_3$ |
| $CH_3$ | $CH(CH_3)_2$ | 4-$OCH_3$ |
| $CH_3$ | $CH(CH_3)_2$ | 3,4-$(OCH_3)_2$ |
| $CH_3$ | $CH(CH_3)_2$ | 3,5-$(OCH_3)_2$ |
| $CH_3$ | $CH(CH_3)_2$ | 3,4,5-$(OCH_3)_3$ |
| $CH_3$ | $CH(CH_3)_2$ | 4-$OC_2H_5$ |
| $CH_3$ | $CH(CH_3)_2$ | 4-O-i-$C_3H_7$ |
| $CH_3$ | $CH(CH_3)_2$ | 3-O-t-$C_4H_9$ |
| $CH_3$ | $CH(CH_3)_2$ | 4-O-t-$C_4H_9$ |
| $CH_3$ | $CH(CH_3)_2$ | 4-O-n-$C_6H_{13}$ |
| $CH_3$ | $CH(CH_3)_2$ | 3-O-Phenyl |
| $CH_3$ | $CH(CH_3)_2$ | 4-O-Phenyl |
| $CH_3$ | $CH(CH_3)_2$ | 4-O-Allyl |
| $CH_3$ | $CH(CH_3)_2$ | 2-$CF_3$ |
| $CH_3$ | $CH(CH_3)_2$ | 3-$CF_3$ |
| $CH_3$ | $CH(CH_3)_2$ | 4-$CF_3$ |
| $CH_3$ | $CH(CH_3)_2$ | 3,5-$(CF_3)_2$ |
| $CH_3$ | $CH(CH_3)_2$ | 4-$CH_2CF_3$ |
| $CH_3$ | $CH(CH_3)_2$ | 4-$C_2F_5$ |
| $CH_3$ | $CH(CH_3)_2$ | 4-$CF_2CHF_2$ |
| $CH_3$ | $CH(CH_3)_2$ | 3-$OCF_3$ |
| $CH_3$ | $CH(CH_3)_2$ | 4-$OCF_3$ |
| $CH_3$ | $CH(CH_3)_2$ | 4-$OCH_2CF_3$ |
| $CH_3$ | $CH(CH_3)_2$ | 4-$OC_2F_5$ |
| $CH_3$ | $CH(CH_3)_2$ | 4-$OCF_2CHF_2$ |
| $CH_3$ | $CH(CH_3)_2$ | 3-$CH_2OCH_3$ |
| $CH_3$ | $CH(CH_3)_2$ | 4-$CH_2OCH_3$ |
| $CH_3$ | $CH(CH_3)_2$ | 4-$CH_2$—O-t-$C_4H_9$ |
| $CH_3$ | $CH(CH_3)_2$ | 4-$CH(OCH_3)_2$ |
| $CH_3$ | $CH(CH_3)_2$ | 4-$CH_2CN$ |
| $CH_3$ | $CH(CH_3)_2$ | 3-CHO |
| $CH_3$ | $CH(CH_3)_2$ | 4-CHO |
| $CH_3$ | $CH(CH_3)_2$ | 3-CO—$CH_3$ |
| $CH_3$ | $CH(CH_3)_2$ | 4-CO—$CH_3$ |
| $CH_3$ | $CH(CH_3)_2$ | 3-COOH |
| $CH_3$ | $CH(CH_3)_2$ | 4-COOH |
| $CH_3$ | $CH(CH_3)_2$ | 3-$COOCH_3$ |
| $CH_3$ | $CH(CH_3)_2$ | 4-$COOCH_3$ |
| $CH_3$ | $CH(CH_3)_2$ | 3-$COOC_2H_5$ |
| $CH_3$ | $CH(CH_3)_2$ | 4-$COOC_2H_5$ |
| $CH_3$ | $CH(CH_3)_2$ | 3-COO-i-$C_3H_7$ |
| $CH_3$ | $CH(CH_3)_2$ | 4-COO-i-$C_3H_7$ |
| $CH_3$ | $CH(CH_3)_2$ | 3-COO-t-$C_4H_9$ |
| $CH_3$ | $CH(CH_3)_2$ | 4-COO-t-$C_4H_9$ |
| $CH_3$ | $CH(CH_3)_2$ | 3-COO-n-$C_6H_{13}$ |
| $CH_3$ | $CH(CH_3)_2$ | 4-COO-n-$C_6H_{13}$ |
| $CH_3$ | $CH(CH_3)_2$ | 3-$CONH_2$ |
| $CH_3$ | $CH(CH_3)_2$ | 4-$CONH_2$ |
| $CH_3$ | $CH(CH_3)_2$ | 3-$CONHCH_3$ |
| $CH_3$ | $CH(CH_3)_2$ | 4-$CONHCH_3$ |
| $CH_3$ | $CH(CH_3)_2$ | 3-$CON(CH_3)_2$ |
| $CH_3$ | $CH(CH_3)_2$ | 4-$CON(CH_3)_2$ |
| $CH_3$ | $CH(CH_3)_2$ | 3-$CSNH_2$ |
| $CH_3$ | $CH(CH_3)_2$ | 4-$CSNH_2$ |
| $CH_3$ | $CH(CH_3)_2$ | 3-$NH_2$ |
| $CH_3$ | $CH(CH_3)_2$ | 4-$NH_2$ |
| $CH_3$ | $CH(CH_3)_2$ | 4-$NHCH_3$ |
| $CH_3$ | $CH(CH_3)_2$ | 4-$N(CH_3)_2$ |
| $CH_3$ | $CH(CH_3)_2$ | 3-NHCO—$CH_3$ |
| $CH_3$ | $CH(CH_3)_2$ | 4-NHCO—$CH_3$ |
| $CH_3$ | $CH(CH_3)_2$ | 4-$NCH_3$—CO—$CH_3$ |
| $CH_3$ | $CH(CH_3)_2$ | 4-$NHCOOCH_3$ |
| $CH_3$ | $CH(CH_3)_2$ | 4-$NCH_3$—$COOCH_3$ |
| $CH_3$ | $CH(CH_3)_2$ | 3-OCO—$CH_3$ |
| $CH_3$ | $CH(CH_3)_2$ | 4-OCO—$CH_3$ |
| $CH_3$ | $CH(CH_3)_2$ | 4-OCO-t-$C_4H_9$ |
| $CH_3$ | $CH(CH_3)_2$ | 4-SH |
| $CH_3$ | $CH(CH_3)_2$ | 4-$SCH_3$ |
| $CH_3$ | $CH(CH_3)_2$ | 4-S-t-$C_4H_9$ |
| $CH_3$ | $CH(CH_3)_2$ | 4-SO—$CH_3$ |
| $CH_3$ | $CH(CH_3)_2$ | 4-$SO_2$—$CH_3$ |
| $CH_3$ | $CH(CH_3)_2$ | 4-$C(CH_3)$=$NCH_3$ |
| $CH_3$ | $CH(CH_3)_2$ | 4-$C(SCH_3)$=$NOCH_3$ |
| $CH_3$ | $CH(CH_3)_2$ | 4-$C(OCH_3)$=$NOCH_3$ |
| $CH_3$ | $CH(CH_3)_2$ | 3-CH=$NOCH_3$ |
| $CH_3$ | $CH(CH_3)_2$ | 4-CH=$NOCH_3$ |
| $CH_3$ | $CH(CH_3)_2$ | 3-$C(CH_3)$=$NOCH_3$ |
| $CH_3$ | $CH(CH_3)_2$ | 4-$C(CH_3)$=$NOCH_3$ |
| $CH_3$ | $CH(CH_3)_2$ | 4-$C(CH_3)$=$NOC_2H_5$ |
| $CH_3$ | $CH(CH_3)_2$ | 4-$C(CH_3)$=NO-n-$C_3H_7$ |
| $CH_3$ | $CH(CH_3)_2$ | 4-$C(CH_3)$=NO-i-$C_3H_7$ |
| $CH_3$ | $CH(CH_3)_2$ | 4-$C(CH_3)$=NO-n-$C_4H_9$ |
| $CH_3$ | $CH(CH_3)_2$ | 4-$C(CH_3)$=NO-t-$C_4H_9$ |
| $CH_3$ | $CH(CH_3)_2$ | 4-$C(CH_3)$=NO-n-$C_5H_{11}$ |
| $CH_3$ | $CH(CH_3)_2$ | 4-$C(CH_3)$=NO-n-$C_6H_{13}$ |
| $CH_3$ | $CH(CH_3)_2$ | 2-Cl, 4-$CH_3$ |
| $CH_3$ | $CH(CH_3)_2$ | 3-Cl, 5-$CH_3$ |
| $CH_3$ | $CH(CH_3)_2$ | 2-$CH_3$, 4-Cl |
| $CH_3$ | $CH(CH_3)_2$ | 3-$CH_3$, 4-Cl |
| $CH_3$ | $CH(CH_3)_2$ | 3-F, 5-$CH_3$ |
| $CH_3$ | $CH(CH_3)_2$ | 3-Br, 5-$CH_3$ |
| $CH_3$ | $CH(CH_3)_2$ | 3-Cl, 5-$NO_2$ |
| $CH_3$ | $CH(CH_3)_2$ | 3-$NO_2$, 4-Cl |
| $CH_3$ | $CH(CH_3)_2$ | 3-Cl, 4-$OCH_3$ |
| $CH_3$ | $CH(CH_3)_2$ | 3-$OCH_3$, 4-Cl |
| $CH_3$ | $CH(CH_3)_2$ | 3-Cl, 5-$CF_3$ |
| $CH_3$ | $CH(CH_3)_2$ | 3-Cl, 5-$OCF_3$ |
| $CH_3$ | $CH(CH_3)_2$ | 3-F, 5-$CF_3$ |
| $CH_3$ | $CH(CH_3)_2$ | 2-$CH_3$, 4-CN |
| $CH_3$ | $CH(CH_3)_2$ | 2-$CH_3$, 4-$OCH_3$ |
| $CH_3$ | $CH(CH_3)_2$ | 2-$CH_3$, 4-$CF_3$ |
| $CH_3$ | $CH(CH_3)_2$ | 2-$CH_3$, 4-$C(CH_3)$=$NOCH_3$ |
| $CH_3$ | $CH(CH_3)_2$ | 3-$CH_3$, 4-$C(CH_3)$=$NOCH_3$ |
| $CH_3$ | $CH(CH_3)_2$ | 2-OH, 5-$CH_3$ |
| $CH_3$ | $CH(CH_3)_2$ | 3-$CH_3$, 4-O-t-$C_4H_9$ |
| $CH_3$ | $CH(CH_3)_2$ | 2-$C(COOCH_3)$=$NOCH_3$ |
| $CH_3$ | $CH(CH_3)_2$ | 2,3-Butadienyl |
| $CH_3$ | $CH(CH_3)_2$ | 3,4-Butadienyl |
| H | $CF_3$ | H |
| H | $CF_3$ | 2-F |
| H | $CF_3$ | 3-F |
| H | $CF_3$ | 4-F |
| H | $CF_3$ | 2,3-$F_2$ |
| H | $CF_3$ | 2,4-$F_2$ |
| H | $CF_3$ | 2,5-$F_2$ |
| H | $CF_3$ | 2,6-$F_2$ |
| H | $CF_3$ | 3,4-$F_2$ |
| H | $CF_3$ | 3,5-$F_2$ |
| H | $CF_3$ | 2-Cl |
| H | $CF_3$ | 3-Cl |
| H | $CF_3$ | 4-Cl |
| H | $CF_3$ | 2,4-$Cl_2$ |
| H | $CF_3$ | 2,5-$Cl_2$ |
| H | $CF_3$ | 3,4-$Cl_2$ |
| H | $CF_3$ | 3,5-$Cl_2$ |
| H | $CF_3$ | 2-Br |
| H | $CF_3$ | 3-Br |
| H | $CF_3$ | 4-Br |
| H | $CF_3$ | 2,4-$Br_2$ |
| H | $CF_3$ | 3,4-$Br_2$ |
| H | $CF_3$ | 3,5-$Br_2$ |
| H | $CF_3$ | 2-I |
| H | $CF_3$ | 3-I |
| H | $CF_3$ | 4-I |
| H | $CF_3$ | 2-F, 4-Cl |
| H | $CF_3$ | 2-F, 5-Cl |
| H | $CF_3$ | 2-F, 4-Br |
| H | $CF_3$ | 2-F, 5-Br |
| H | $CF_3$ | 2-Cl, 4-Br |
| H | $CF_3$ | 2-Cl, 5-Br |
| H | $CF_3$ | 3-F, 4-Cl |

TABLE A-continued

| R | A | Q_m |
|---|---|---|
| H | $CF_3$ | 3-F, 5-Cl |
| H | $CF_3$ | 3-F, 4-Br |
| H | $CF_3$ | 3-F, 5-Br |
| H | $CF_3$ | 3-Cl, 4-Br |
| H | $CF_3$ | 3-Cl, 5-Br |
| H | $CF_3$ | 3-Cl, 4-F |
| H | $CF_3$ | 3-Br, 4-F |
| H | $CF_3$ | 3-Br, 4-Cl |
| H | $CF_3$ | 2-$NO_2$ |
| H | $CF_3$ | 3-$NO_2$ |
| H | $CF_3$ | 4-$NO_2$ |
| H | $CF_3$ | 2-CN |
| H | $CF_3$ | 3-CN |
| H | $CF_3$ | 4-CN |
| H | $CF_3$ | 2-$CH_3$ |
| H | $CF_3$ | 3-$CH_3$ |
| H | $CF_3$ | 4-$CH_3$ |
| H | $CF_3$ | 2,3-$(CH_3)_2$ |
| H | $CF_3$ | 2,4-$(CH_3)_2$ |
| H | $CF_3$ | 2,5-$(CH_3)_2$ |
| H | $CF_3$ | 2,6-$(CH_3)_2$ |
| H | $CF_3$ | 3,4-$(CH_3)_2$ |
| H | $CF_3$ | 3,5-$(CH_3)_2$ |
| H | $CF_3$ | 2,4,5-$(CH_3)_3$ |
| H | $CF_3$ | 2,4,6-$(CH_3)_3$ |
| H | $CF_3$ | 3,4,5-$(CH_3)_3$ |
| H | $CF_3$ | 2-$C_2H_5$ |
| H | $CF_3$ | 3-$C_2H_5$ |
| H | $CF_3$ | 4-$C_2H_5$ |
| H | $CF_3$ | 3,4-$(C_2H_5)_2$ |
| H | $CF_3$ | 3,5-$(C_2H_5)_2$ |
| H | $CF_3$ | 3-n-$C_3H_7$ |
| H | $CF_3$ | 4-n-$C_3H_7$ |
| H | $CF_3$ | 3,4-(n-$C_3H_7)_2$ |
| H | $CF_3$ | 3,5-(n-$C_3H_7)_2$ |
| H | $CF_3$ | 3-i-$C_3H_7$ |
| H | $CF_3$ | 4-i-$C_3H_7$ |
| H | $CF_3$ | 3,4-(i-$C_3H_7)_2$ |
| H | $CF_3$ | 3,5-(i-$C_3H_7)_2$ |
| H | $CF_3$ | 3-Cyclopropyl |
| H | $CF_3$ | 4-Cyclopropyl |
| H | $CF_3$ | 3-n-$C_4H_9$ |
| H | $CF_3$ | 4-n-$C_4H_9$ |
| H | $CF_3$ | 3,4-(n-$C_4H_9)_2$ |
| H | $CF_3$ | 3,5-(n-$C_4H_9)_2$ |
| H | $CF_3$ | 3-s-$C_4H_9$ |
| H | $CF_3$ | 4-s-$C_4H_9$ |
| H | $CF_3$ | 3-i-$C_4H_9$ |
| H | $CF_3$ | 4-i-$C_4H_9$ |
| H | $CF_3$ | 3-t-$C_4H_9$ |
| H | $CF_3$ | 4-t-$C_4H_9$ |
| H | $CF_3$ | 3,4-(t-$C_4H_9)_2$ |
| H | $CF_3$ | 3,5-(t-$C_4H_9)_2$ |
| H | $CF_3$ | 3-n-$C_5H_{11}$ |
| H | $CF_3$ | 4-n-$C_5H_{11}$ |
| H | $CF_3$ | 3-n-$C_6H_{13}$ |
| H | $CF_3$ | 4-n-$C_6H_{13}$ |
| H | $CF_3$ | 3-Cyclohexyl |
| H | $CF_3$ | 4-Cyclohexyl |
| H | $CF_3$ | 3-Phenyl |
| H | $CF_3$ | 4-Phenyl |
| H | $CF_3$ | 3-Vinyl |
| H | $CF_3$ | 4-Vinyl |
| H | $CF_3$ | 3-Allyl |
| H | $CF_3$ | 4-Allyl |
| H | $CF_3$ | 3-Propargyl |
| H | $CF_3$ | 4-Propargyl |
| H | $CF_3$ | 3-(Propen-2-yl) |
| H | $CF_3$ | 4-(Propen-2-yl) |
| H | $CF_3$ | 2-$CH_3$, 4-$C_2H_5$ |
| H | $CF_3$ | 2-$CH_3$, 5-$C_2H_5$ |
| H | $CF_3$ | 2-$CH_3$, 4-n-$C_3H_7$ |
| H | $CF_3$ | 2-$CH_3$, 5-n-$C_3H_7$ |
| H | $CF_3$ | 2-$CH_3$, 4-i-$C_3H_7$ |
| H | $CF_3$ | 2-$CH_3$, 5-i-$C_3H_7$ |
| H | $CF_3$ | 2-$CH_3$, 4-n-$C_4H_9$ |
| H | $CF_3$ | 2-$CH_3$, 4-s-$C_4H_9$ |
| H | $CF_3$ | 2-$CH_3$, 4-i-$C_4H_9$ |
| H | $CF_3$ | 2-$CH_3$, 4-t-$C_4H_9$ |
| H | $CF_3$ | 2-$CH_3$, 4-phenyl |
| H | $CF_3$ | 2-$CH_3$, 5-phenyl |
| H | $CF_3$ | 2-$CH_3$, 4-vinyl |
| H | $CF_3$ | 2-$CH_3$, 4-allyl |
| H | $CF_3$ | 2-$CH_3$, 4-propargyl |
| H | $CF_3$ | 2-$CH_3$, 4-(propen-2-yl) |
| H | $CF_3$ | 3-$CH_3$, 4-$C_2H_5$ |
| H | $CF_3$ | 3-$CH_3$, 5-$C_2H_5$ |
| H | $CF_3$ | 3-$CH_3$, 4-n-$C_3H_7$ |
| H | $CF_3$ | 3-$CH_3$, 5-n-$C_3H_7$ |
| H | $CF_3$ | 3-$CH_3$, 4-i-$C_3H_7$ |
| H | $CF_3$ | 3-$CH_3$, 5-i-$C_3H_7$ |
| H | $CF_3$ | 3-$CH_3$, 4-cyclopropyl |
| H | $CF_3$ | 3-$CH_3$, 4-t-$C_4H_9$ |
| H | $CF_3$ | 3-$CH_3$, 5-t-$C_4H_9$ |
| H | $CF_3$ | 3-$CH_3$, 4-phenyl |
| H | $CF_3$ | 3-$CH_3$, 5-phenyl |
| H | $CF_3$ | 3-$CH_3$, 4-vinyl |
| H | $CF_3$ | 3-$CH_3$, 4-allyl |
| H | $CF_3$ | 3-$CH_3$, 4-propargyl |
| H | $CF_3$ | 3-$CH_3$, 4-propen-2-yl |
| H | $CF_3$ | 3-$C_2H_5$, 4-$CH_3$ |
| H | $CF_3$ | 3-i-$C_3H_7$, 4-$CH_3$ |
| H | $CF_3$ | 3-t-$C_4H_9$, 4-$CH_3$ |
| H | $CF_3$ | 3-Phenyl, 4-$CH_3$ |
| H | $CF_3$ | 2-OH |
| H | $CF_3$ | 3-OH |
| H | $CF_3$ | 4-OH |
| H | $CF_3$ | 2-$OCH_3$ |
| H | $CF_3$ | 3-$OCH_3$ |
| H | $CF_3$ | 4-$OCH_3$ |
| H | $CF_3$ | 2,3-$(OCH_3)_2$ |
| H | $CF_3$ | 2,4-$(OCH_3)_2$ |
| H | $CF_3$ | 2,5-$(OCH_3)_2$ |
| H | $CF_3$ | 3,4-$(OCH_3)_2$ |
| H | $CF_3$ | 3,5-$(OCH_3)_2$ |
| H | $CF_3$ | 3,4,5-$(OCH_3)_3$ |
| H | $CF_3$ | 3-$OC_2H_5$ |
| H | $CF_3$ | 4-$OC_2H_5$ |
| H | $CF_3$ | 3,4-$(OC_2H_5)_2$ |
| H | $CF_3$ | 3,5-$(OC_2H_5)_2$ |
| H | $CF_3$ | 3-O-n-$C_3H_7$ |
| H | $CF_3$ | 4-O-n-$C_3H_7$ |
| H | $CF_3$ | 3-O-i-$C_3H_7$ |
| H | $CF_3$ | 4-O-i-$C_3H_7$ |
| H | $CF_3$ | 3-O-Cyclopropyl |
| H | $CF_3$ | 4-O-Cyclopropyl |
| H | $CF_3$ | 3-O-n-$C_4H_9$ |
| H | $CF_3$ | 4-O-n-$C_4H_9$ |
| H | $CF_3$ | 3-O-s-$C_4H_9$ |
| H | $CF_3$ | 4-O-s-$C_4H_9$ |
| H | $CF_3$ | 3-O-i-$C_4H_9$ |
| H | $CF_3$ | 4-O-i-$C_4H_9$ |
| H | $CF_3$ | 3-O-t-$C_4H_9$ |
| H | $CF_3$ | 4-O-t-$C_4H_9$ |
| H | $CF_3$ | 3-O-n-$C_5H_{11}$ |
| H | $CF_3$ | 4-O-n-$C_5H_{11}$ |
| H | $CF_3$ | 3-O-n-$C_6H_{13}$ |
| H | $CF_3$ | 4-O-n-$C_6H_{13}$ |
| H | $CF_3$ | 3-O-Cyclohexyl |
| H | $CF_3$ | 4-O-Cyclohexyl |
| H | $CF_3$ | 3-O-Phenyl |
| H | $CF_3$ | 4-O-Phenyl |
| H | $CF_3$ | 3-O-Allyl |
| H | $CF_3$ | 4-O-Allyl |
| H | $CF_3$ | 2-$CF_3$ |
| H | $CF_3$ | 3-$CF_3$ |
| H | $CF_3$ | 4-$CF_3$ |
| H | $CF_3$ | 2,4-$(CF_3)_2$ |
| H | $CF_3$ | 3,5-$(CF_3)_2$ |
| H | $CF_3$ | 3-$CF_2Cl$ |
| H | $CF_3$ | 4-$CF_2Cl$ |
| H | $CF_3$ | 3-$CFCl_2$ |
| H | $CF_3$ | 4-$CFCl_2$ |
| H | $CF_3$ | 3-$CCl_3$ |

TABLE A-continued

| R | A | $Q_m$ |
|---|---|---|
| H | $CF_3$ | 4-$CCl_3$ |
| H | $CF_3$ | 3-$CH_2CH_2F$ |
| H | $CF_3$ | 4-$CH_2CH_2F$ |
| H | $CF_3$ | 3-$CH_2CF_3$ |
| H | $CF_3$ | 4-$CH_2CF_3$ |
| H | $CF_3$ | 3-$C_2F_5$ |
| H | $CF_3$ | 5-$C_2F_5$ |
| H | $CF_3$ | 3-$CHCl_2$ |
| H | $CF_3$ | 4-$CHCl_2$ |
| H | $CF_3$ | 3-$CH_2Cl$ |
| H | $CF_3$ | 4-$CH_2Cl$ |
| H | $CF_3$ | 3-$CF_2CHF_2$ |
| H | $CF_3$ | 4-$CF_2CHF_2$ |
| H | $CF_3$ | 3-$CH_2CH_2Cl$ |
| H | $CF_3$ | 4-$CH_2CH_2Cl$ |
| H | $CF_3$ | 2-$OCF_3$ |
| H | $CF_3$ | 3-$OCF_3$ |
| H | $CF_3$ | 4-$OCF_3$ |
| H | $CF_3$ | 3-$OCHF_2$ |
| H | $CF_3$ | 4-$OCHF_2$ |
| H | $CF_3$ | 3-$OC_2F_5$ |
| H | $CF_3$ | 4-$OC_2F_5$ |
| H | $CF_3$ | 3-$OCF_2CHF_2$ |
| H | $CF_3$ | 4-$OCF_2CHF_2$ |
| H | $CF_3$ | 3-$CH_2OCH_3$ |
| H | $CF_3$ | 4-$CH_2OCH_3$ |
| H | $CF_3$ | 3-$CH_2O$-t-$C_4H_9$ |
| H | $CF_3$ | 4-$CH_2O$-t-$C_4H_9$ |
| H | $CF_3$ | 3-$C(CH_3)(OCH_3)_2$ |
| H | $CF_3$ | 4-$C(CH_3)(OCH_3)_2$ |
| H | $CF_3$ | 3-$CH(OCH_3)_2$ |
| H | $CF_3$ | 4-$CH(OCH_3)_2$ |
| H | $CF_3$ | 3-$CH_2CN$ |
| H | $CF_3$ | 4-$CH_2CN$ |
| H | $CF_3$ | 3-CHO |
| H | $CF_3$ | 4-CHO |
| H | $CF_3$ | 3-CO—$CH_3$ |
| H | $CF_3$ | 4-CO—$CH_3$ |
| H | $CF_3$ | 3-CO—$C_2H_5$ |
| H | $CF_3$ | 4-CO—$C_2H_5$ |
| H | $CF_3$ | 2-COOH |
| H | $CF_3$ | 3-COOH |
| H | $CF_3$ | 4-COOH |
| H | $CF_3$ | 3-$COOCH_3$ |
| H | $CF_3$ | 4-$COOCH_3$ |
| H | $CF_3$ | 3-$COOC_2H_5$ |
| H | $CF_3$ | 4-$COOC_2H_5$ |
| H | $CF_3$ | 3-COO-n-$C_3H_7$ |
| H | $CF_3$ | 4-COO-n-$C_3H_7$ |
| H | $CF_3$ | 3-COO-i-$C_3H_7$ |
| H | $CF_3$ | 4-COO-i-$C_3H_7$ |
| H | $CF_3$ | 3-COO-n-$C_4H_9$ |
| H | $CF_3$ | 4-COO-n-$C_4H_9$ |
| H | $CF_3$ | 3-COO-s-$C_4H_9$ |
| H | $CF_3$ | 4-COO-s-$C_4H_9$ |
| H | $CF_3$ | 3-COO-i-$C_4H_9$ |
| H | $CF_3$ | 4-COO-i-$C_4H_9$ |
| H | $CF_3$ | 3-COO-t-$C_4H_9$ |
| H | $CF_3$ | 4-COO-t-$C_4H_9$ |
| H | $CF_3$ | 3-COO-n-$C_5H_{11}$ |
| H | $CF_3$ | 4-COO-n-$C_5H_{11}$ |
| H | $CF_3$ | 3-COO-n-$C_6H_{13}$ |
| H | $CF_3$ | 4-COO-n-$C_6H_{13}$ |
| H | $CF_3$ | 2-$CONH_2$ |
| H | $CF_3$ | 3-$CONH_2$ |
| H | $CF_3$ | 4-$CONH_2$ |
| H | $CF_3$ | 3-$CONHCH_3$ |
| H | $CF_3$ | 4-$CONHCH_3$ |
| H | $CF_3$ | 3-$CON(CH_3)_2$ |
| H | $CF_3$ | 4-$CON(CH_3)_2$ |
| H | $CF_3$ | 3-$CON(C_2H_5)_2$ |
| H | $CF_3$ | 4-$CON(C_2H_5)_2$ |
| H | $CF_3$ | 2-$CSNH_2$ |
| H | $CF_3$ | 3-$CSNH_2$ |
| H | $CF_3$ | 4-$CSNH_2$ |
| H | $CF_3$ | 2-$NH_2$ |
| H | $CF_3$ | 3-$NH_2$ |
| H | $CF_3$ | 4-$NH_2$ |
| H | $CF_3$ | 3-$NHCH_3$ |
| H | $CF_3$ | 4-$NHCH_3$ |
| H | $CF_3$ | 3-$N(CH_3)_2$ |
| H | $CF_3$ | 4-$N(CH_3)_2$ |
| H | $CF_3$ | 3-NHCO—$CH_3$ |
| H | $CF_3$ | 4-NHCO—$CH_3$ |
| H | $CF_3$ | 3-$NCH_3$—CO—$CH_3$ |
| H | $CF_3$ | 4-$NCH_3$—CO—$CH_3$ |
| H | $CF_3$ | 3-$NHCOOCH_3$ |
| H | $CF_3$ | 4-$NHCOOCH_3$ |
| H | $CF_3$ | 3-$NCH_3$—$COOCH_3$ |
| H | $CF_3$ | 4-$NCH_3$—$COOCH_3$ |
| H | $CF_3$ | 3-OCO—$CH_3$ |
| H | $CF_3$ | 4-OCO—$CH_3$ |
| H | $CF_3$ | 3-OCO-t-$C_4H_9$ |
| H | $CF_3$ | 4-OCO-t-$C_4H_9$ |
| H | $CF_3$ | 3-SH |
| H | $CF_3$ | 4-SH |
| H | $CF_3$ | 3-$SCH_3$ |
| H | $CF_3$ | 4-$SCH_3$ |
| H | $CF_3$ | 3-S-t-$C_4H_9$ |
| H | $CF_3$ | 4-S-t-$C_4H_9$ |
| H | $CF_3$ | 3-SO—$CH_3$ |
| H | $CF_3$ | 4-SO—$CH_3$ |
| H | $CF_3$ | 3-$SO_2CH_3$ |
| H | $CF_3$ | 4-$SO_2CH_3$ |
| H | $CF_3$ | 3-CH=$NCH_3$ |
| H | $CF_3$ | 4-CH=$NCH_3$ |
| H | $CF_3$ | 3-$C(CH_3)$=$NCH_3$ |
| H | $CF_3$ | 4-$C(CH_3)$=$NCH_3$ |
| H | $CF_3$ | 3-$C(SCH_3)$=$NOCH_3$ |
| H | $CF_3$ | 4-$C(SCH_3)$=$NOCH_3$ |
| H | $CF_3$ | 3-$C(OCH_3)$=$NOCH_3$ |
| H | $CF_3$ | 4-$C(OCH_3)$=$NOCH_3$ |
| H | $CF_3$ | 3-$C(NH_2)$=$NOCH_3$ |
| H | $CF_3$ | 4-$C(NH_2)$=$NOCH_3$ |
| H | $CF_3$ | 3-$C(NHCH_3)$=$NOCH_3$ |
| H | $CF_3$ | 4-$C(NHCH_3)$=$NOCH_3$ |
| H | $CF_3$ | 3-CH=$NOCH_3$ |
| H | $CF_3$ | 4-CH=$NOCH_3$ |
| H | $CF_3$ | 3-$C(CH_3)$=$NOCH_3$ |
| H | $CF_3$ | 4-$C(CH_3)$=$NOCH_3$ |
| H | $CF_3$ | 3-$C(CH_3)$=$NOC_2H_5$ |
| H | $CF_3$ | 4-$C(CH_3)$=$NOC_2H_5$ |
| H | $CF_3$ | 3-$C(CH_3)$=NO-n-$C_3H_7$ |
| H | $CF_3$ | 4-$C(CH_3)$=NO-n-$C_3H_7$ |
| H | $CF_3$ | 3-$C(CH_3)$=NO-i-$C_3H_7$ |
| H | $CF_3$ | 4-$C(CH_3)$=NO-i-$C_3H_7$ |
| H | $CF_3$ | 3-$C(CH_3)$=NO-n-$C_4H_9$ |
| H | $CF_3$ | 4-$C(CH_3)$=NO-n-$C_4H_9$ |
| H | $CF_3$ | 3-$C(CH_3)$=NO-s-$C_4H_9$ |
| H | $CF_3$ | 4-$C(CH_3)$=NO-s-$C_4H_9$ |
| H | $CF_3$ | 3-$C(CH_3)$=NO-i-$C_4H_9$ |
| H | $CF_3$ | 4-$C(CH_3)$=NO-i-$C_4H_9$ |
| H | $CF_3$ | 3-$C(CH_3)$=NO-t-$C_4H_9$ |
| H | $CF_3$ | 4-$C(CH_3)$=NO-t-$C_4H_9$ |
| H | $CF_3$ | 3-$C(CH_3)$=NO-n-$C_5H_{11}$ |
| H | $CF_3$ | 4-$C(CH_3)$=NO-n-$C_5H_{11}$ |
| H | $CF_3$ | 3-$C(CH_3)$=NO-n-$C_6H_{13}$ |
| H | $CF_3$ | 4-$C(CH_3)$=NO-n-$C_6H_{13}$ |
| H | $CF_3$ | 2-Cl, 4-$CH_3$ |
| H | $CF_3$ | 2-Cl, 5-$CH_3$ |
| H | $CF_3$ | 3-Cl, 4-$CH_3$ |
| H | $CF_3$ | 3-Cl, 5-$CH_3$ |
| H | $CF_3$ | 2-$CH_3$, 4-Cl |
| H | $CF_3$ | 2-$CH_3$, 5-Cl |
| H | $CF_3$ | 3-$CH_3$, 4-Cl |
| H | $CF_3$ | 3-Cl, 5-t-$C_4H_9$ |
| H | $CF_3$ | 2-Cl, 4-t-$C_4H_9$ |
| H | $CF_3$ | 2-F, 4-$CH_3$ |
| H | $CF_3$ | 3-F, 4-$CH_3$ |
| H | $CF_3$ | 3-F, 5-$CH_3$ |
| H | $CF_3$ | 2-$CH_3$, 4-F |
| H | $CF_3$ | 3-$CH_3$, 4-F |
| H | $CF_3$ | 2-F, 4-t-$C_4H_9$ |
| H | $CF_3$ | 3-F, 4-t-$C_4H_9$ |

TABLE A-continued

| R | A | Q_m |
|---|---|---|
| H | $CF_3$ | 2-F, 4-$OCH_3$ |
| H | $CF_3$ | 2-Br, 4-$CH_3$ |
| H | $CF_3$ | 3-Br, 4-$CH_3$ |
| H | $CF_3$ | 3-Br, 5-$CH_3$ |
| H | $CF_3$ | 2-$CH_3$, 4-Br |
| H | $CF_3$ | 3-$CH_3$, 4-Br |
| H | $CF_3$ | 2-Br, 4-t-$C_4H_9$ |
| H | $CF_3$ | 2-Cl, 4-$NO_2$ |
| H | $CF_3$ | 3-Cl, 4-$NO_2$ |
| H | $CF_3$ | 3-Cl, 5-$NO_2$ |
| H | $CF_3$ | 3-$NO_2$, 4-Cl |
| H | $CF_3$ | 3-Cl, 4-OCH |
| H | $CF_3$ | 3-$OCH_3$, 4-Cl |
| H | $CF_3$ | 2-Cl, 5-$CF_3$ |
| H | $CF_3$ | 3-Cl, 4-$CF_3$ |
| H | $CF_3$ | 3-Cl, 5-$CF_3$ |
| H | $CF_3$ | 3-$CF_3$, 4-Cl |
| H | $CF_3$ | 3-Cl, 5-$OCF_3$ |
| H | $CF_3$ | 3-F, 5-$CF_3$ |
| H | $CF_3$ | 2-$CH_3$, 4-CN |
| H | $CF_3$ | 3-$NO_2$, 4-$CH_3$ |
| H | $CF_3$ | 2-$CH_3$, 4-$OCH_3$ |
| H | $CF_3$ | 3-$CH_3$, 4-$OCH_3$ |
| H | $CF_3$ | 3-$CH_3$, 5-$OCH_3$ |
| H | $CF_3$ | 3-$OCH_3$, 4-$CH_3$ |
| H | $CF_3$ | 2-$CH_3$, 4-O-i-$C_3H_7$ |
| H | $CF_3$ | 3-$CH_3$, 4-O-i-$C_3H_7$ |
| H | $CF_3$ | 3-O-i-$C_3H_7$, 4-$CH_3$ |
| H | $CF_3$ | 2-$CH_3$, 4-$CF_3$ |
| H | $CF_3$ | 2-$CH_3$, 5-$CF_3$ |
| H | $CF_3$ | 3-$CH_3$, 4-$CF_3$ |
| H | $CF_3$ | 3-$CH_3$, 5-$CF_3$ |
| H | $CF_3$ | 3-$CF_3$, 4-$CH_3$ |
| H | $CF_3$ | 3-$CF_3$, 4-$OCH_3$ |
| H | $CF_3$ | 3-$OCH_3$, 4-$CF_3$ |
| H | $CF_3$ | 2-$CH_3$, 4-C($CH_3$)=$NOCH_3$ |
| H | $CF_3$ | 3-$CH_3$, 4-C($CH_3$)=$NOCH_3$ |
| H | $CF_3$ | 2-OH, 5-$CH_3$ |
| H | $CF_3$ | 3-$CH_3$, 4-$OC_2H_5$ |
| H | $CF_3$ | 3-$CH_3$, 4-O-t-$C_4H_9$ |
| H | $CF_3$ | 3-$OC_2H_5$, 4-$CH_3$ |
| H | $CF_3$ | 3-O-t-$C_4H_9$, 4-$CH_3$ |
| H | $CF_3$ | 2-C($COOCH_3$)=$NOCH_3$ |
| H | $CF_3$ | 2,3-Butadienyl |
| H | $CF_3$ | 3,4-Butadienyl |
| $CH_3$ | $CF_3$ | H |
| $CH_3$ | $CF_3$ | 2-F |
| $CH_3$ | $CF_3$ | 3-F |
| $CH_3$ | $CF_3$ | 4-F |
| $CH_3$ | $CF_3$ | 2,4-$F_2$ |
| $CH_3$ | $CF_3$ | 3,4-$F_2$ |
| $CH_3$ | $CF_3$ | 3,5-$F_2$ |
| $CH_3$ | $CF_3$ | 2-Cl |
| $CH_3$ | $CF_3$ | 3-Cl |
| $CH_3$ | $CF_3$ | 4-Cl |
| $CH_3$ | $CF_3$ | 2,4-$Cl_2$ |
| $CH_3$ | $CF_3$ | 3,4-$Cl_2$ |
| $CH_3$ | $CF_3$ | 3,5-$Cl_2$ |
| $CH_3$ | $CF_3$ | 2-Br |
| $CH_3$ | $CF_3$ | 3-Br |
| $CH_3$ | $CF_3$ | 4-Br |
| $CH_3$ | $CF_3$ | 3,5-$Br_2$ |
| $CH_3$ | $CF_3$ | 3-I |
| $CH_3$ | $CF_3$ | 4-I |
| $CH_3$ | $CF_3$ | 3-F, 5-Cl |
| $CH_3$ | $CF_3$ | 3-F, 5-Br |
| $CH_3$ | $CF_3$ | 3-Cl, 5-Br |
| $CH_3$ | $CF_3$ | 3-Br, 4-F |
| $CH_3$ | $CF_3$ | 2-$NO_2$ |
| $CH_3$ | $CF_3$ | 3-$NO_2$ |
| $CH_3$ | $CF_3$ | 4-$NO_2$ |
| $CH_3$ | $CF_3$ | 2-CN |
| $CH_3$ | $CF_3$ | 3-CN |
| $CH_3$ | $CF_3$ | 4-CN |
| $CH_3$ | $CF_3$ | 2-$CH_3$ |
| $CH_3$ | $CF_3$ | 3-$CH_3$ |
| $CH_3$ | $CF_3$ | 4-$CH_3$ |
| $CH_3$ | $CF_3$ | 2,4-$(CH_3)_2$ |
| $CH_3$ | $CF_3$ | 2,5-$(CH_3)_2$ |
| $CH_3$ | $CF_3$ | 3,4-$(CH_3)_2$ |
| $CH_3$ | $CF_3$ | 3,5-$(CH_3)_2$ |
| $CH_3$ | $CF_3$ | 2,4,5-$(CH_3)_3$ |
| $CH_3$ | $CF_3$ | 2,4,6-$(CH_3)_3$ |
| $CH_3$ | $CF_3$ | 3-$C_2H_5$ |
| $CH_3$ | $CF_3$ | 4-$C_2H_5$ |
| $CH_3$ | $CF_3$ | 3,4-$(C_2H_5)_2$ |
| $CH_3$ | $CF_3$ | 3,5-$(C_2H_5)_2$ |
| $CH_3$ | $CF_3$ | 3-n-$C_3H_7$ |
| $CH_3$ | $CF_3$ | 4-n-$C_3H_7$ |
| $CH_3$ | $CF_3$ | 3-i-$C_3H_7$ |
| $CH_3$ | $CF_3$ | 4-i-$C_3H_7$ |
| $CH_3$ | $CF_3$ | 3-Cyclopropyl |
| $CH_3$ | $CF_3$ | 4-Cyclopropyl |
| $CH_3$ | $CF_3$ | 3-n-$C_4H_9$ |
| $CH_3$ | $CF_3$ | 4-n-$C_4H_9$ |
| $CH_3$ | $CF_3$ | 3-t-$C_4H_9$ |
| $CH_3$ | $CF_3$ | 4-t-$C_4H_9$ |
| $CH_3$ | $CF_3$ | 3-n-$C_6H_{13}$ |
| $CH_3$ | $CF_3$ | 4-n-$C_6H_{13}$ |
| $CH_3$ | $CF_3$ | 3-Cyclohexyl |
| $CH_3$ | $CF_3$ | 4-Cyclohexyl |
| $CH_3$ | $CF_3$ | 3-Phenyl |
| $CH_3$ | $CF_3$ | 4-Phenyl |
| $CH_3$ | $CF_3$ | 4-Allyl |
| $CH_3$ | $CF_3$ | 4-Propargyl |
| $CH_3$ | $CF_3$ | 2-$CH_3$, 4-$C_2H_5$ |
| $CH_3$ | $CF_3$ | 2-$CH_3$, 4-i-$C_3H_7$ |
| $CH_3$ | $CF_3$ | 2-$CH_3$, 4-t-$C_4H_9$ |
| $CH_3$ | $CF_3$ | 2-$CH_3$, 4-phenyl |
| $CH_3$ | $CF_3$ | 3-$CH_3$, 4-phenyl |
| $CH_3$ | $CF_3$ | 3-OH |
| $CH_3$ | $CF_3$ | 4-OH |
| $CH_3$ | $CF_3$ | 3-$OCH_3$ |
| $CH_3$ | $CF_3$ | 4-$OCH_3$ |
| $CH_3$ | $CF_3$ | 3,4-$(OCH_3)_2$ |
| $CH_3$ | $CF_3$ | 3,5-$(OCH_3)_2$ |
| $CH_3$ | $CF_3$ | 3,4,5-$(OCH_3)_3$ |
| $CH_3$ | $CF_3$ | 4-$OC_2H_5$ |
| $CH_3$ | $CF_3$ | 4-O-i-$C_3H_7$ |
| $CH_3$ | $CF_3$ | 3-O-t-$C_4H_9$ |
| $CH_3$ | $CF_3$ | 4-O-t-$C_4H_9$ |
| $CH_3$ | $CF_3$ | 4-O-n-$C_6H_{13}$ |
| $CH_3$ | $CF_3$ | 3-O-Phenyl |
| $CH_3$ | $CF_3$ | 4-O-Phenyl |
| $CH_3$ | $CF_3$ | 4-O-Allyl |
| $CH_3$ | $CF_3$ | 2-$CF_3$ |
| $CH_3$ | $CF_3$ | 3-$CF_3$ |
| $CH_3$ | $CF_3$ | 4-$CF_3$ |
| $CH_3$ | $CF_3$ | 3,5-$(CF_3)_2$ |
| $CH_3$ | $CF_3$ | 4-$CH_2CF_3$ |
| $CH_3$ | $CF_3$ | 4-$C_2F_5$ |
| $CH_3$ | $CF_3$ | 4-$CF_2CHF_2$ |
| $CH_3$ | $CF_3$ | 3-$OCF_3$ |
| $CH_3$ | $CF_3$ | 4-$OCF_3$ |
| $CH_3$ | $CF_3$ | 4-$OCH_2CF_3$ |
| $CH_3$ | $CF_3$ | 4-$OC_2F_5$ |
| $CH_3$ | $CF_3$ | 4-$OCF_2CHF_2$ |
| $CH_3$ | $CF_3$ | 3-$CH_2OCH_3$ |
| $CH_3$ | $CF_3$ | 4-$CH_2OCH_3$ |
| $CH_3$ | $CF_3$ | 4-$CH_2$—O-t-$C_4H_9$ |
| $CH_3$ | $CF_3$ | 4-CH($OCH_3)_2$ |
| $CH_3$ | $CF_3$ | 4-$CH_2CN$ |
| $CH_3$ | $CF_3$ | 3-CHO |
| $CH_3$ | $CF_3$ | 4-CHO |
| $CH_3$ | $CF_3$ | 3-CO—$CH_3$ |
| $CH_3$ | $CF_3$ | 4-CO—$CH_3$ |
| $CH_3$ | $CF_3$ | 3-COOH |
| $CH_3$ | $CF_3$ | 4-COOH |
| $CH_3$ | $CF_3$ | 3-$COOCH_3$ |
| $CH_3$ | $CF_3$ | 4-$COOCH_3$ |
| $CH_3$ | $CF_3$ | 3-$COOC_2H_5$ |
| $CH_3$ | $CF_3$ | 4-$COOC_2H_5$ |
| $CH_3$ | $CF_3$ | 3-COO-i-$C_3H_7$ |
| $CH_3$ | $CF_3$ | 4-COO-i-$C_3H_7$ |

TABLE A-continued

| R | A | Q_m |
|---|---|---|
| CH₃ | CF₃ | 3-COO-t-C₄H₉ |
| CH₃ | CF₃ | 4-COO-t-C₄H₉ |
| CH₃ | CF₃ | 3-COO-n-C₆H₁₃ |
| CH₃ | CF₃ | 4-COO-n-C₆H₁₃ |
| CH₃ | CF₃ | 3-CONH₂ |
| CH₃ | CF₃ | 4-CONH₂ |
| CH₃ | CF₃ | 3-CONHCH₃ |
| CH₃ | CF₃ | 4-CONHCH₃ |
| CH₃ | CF₃ | 3-CON(CH₃)₂ |
| CH₃ | CF₃ | 4-CON(CH₃)₂ |
| CH₃ | CF₃ | 3-CSNH₂ |
| CH₃ | CF₃ | 4-CSNH₂ |
| CH₃ | CF₃ | 3-NH₂ |
| CH₃ | CF₃ | 4-NH₂ |
| CH₃ | CF₃ | 4-NHCH₃ |
| CH₃ | CF₃ | 4-N(CH₃)₂ |
| CH₃ | CF₃ | 3-NHCO—CH₃ |
| CH₃ | CF₃ | 4-NHCO—CH₃ |
| CH₃ | CF₃ | 4-NCH₃—CO—CH₃ |
| CH₃ | CF₃ | 4-NHCOOCH₃ |
| CH₃ | CF₃ | 4-NCH₃—COOCH₃ |
| CH₃ | CF₃ | 3-OCO—CH₃ |
| CH₃ | CF₃ | 4-OCO—CH₃ |
| CH₃ | CF₃ | 4-OCO-t-C₄H₉ |
| CH₃ | CF₃ | 4-SH |
| CH₃ | CF₃ | 4-SCH₃ |
| CH₃ | CF₃ | 4-S-t-C₄H₉ |
| CH₃ | CF₃ | 4-SO—CH₃ |
| CH₃ | CF₃ | 4-SO₂—CH₃ |
| CH₃ | CF₃ | 4-C(CH₃)=NCH₃ |
| CH₃ | CF₃ | 4-C(SCH₃)=NOCH₃ |
| CH₃ | CF₃ | 4-C(OCH₃)=NOCH₃ |
| CH₃ | CF₃ | 3-CH=NOCH₃ |
| CH₃ | CF₃ | 4-CH=NOCH₃ |
| CH₃ | CF₃ | 3-C(CH₃)=NOCH₃ |
| CH₃ | CF₃ | 4-C(CH₃)=NOCH₃ |
| CH₃ | CF₃ | 4-C(CH₃)=NOC₂H₅ |
| CH₃ | CF₃ | 4-C(CH₃)=NO-n-C₃H₇ |
| CH₃ | CF₃ | 4-C(CH₃)=NO-i-C₃H₇ |
| CH₃ | CF₃ | 4-C(CH₃)=NO-n-C₄H₉ |
| CH₃ | CF₃ | 4-C(CH₃)=NO-t-C₄H₉ |
| CH₃ | CF₃ | 4-C(CH₃)=NO-n-C₅H₁₁ |
| CH₃ | CF₃ | 4-C(CH₃)=NO-n-C₆H₁₃ |
| CH₃ | CF₃ | 2-Cl, 4-CH₃ |
| CH₃ | CF₃ | 3-Cl, 5-CH₃ |
| CH₃ | CF₃ | 2-CH₃, 4-Cl |
| CH₃ | CF₃ | 3-CH₃, 4-Cl |
| CH₃ | CF₃ | 3-F, 5-CH₃ |
| CH₃ | CF₃ | 3-Br, 5-CH₃ |
| CH₃ | CF₃ | 3-Cl, 5-NO₂ |
| CH₃ | CF₃ | 3-NO₂, 4-Cl |
| CH₃ | CF₃ | 3-Cl, 4-OCH₃ |
| CH₃ | CF₃ | 3-OCH₃, 4-Cl |
| CH₃ | CF₃ | 3-Cl, 5-CF₃ |
| CH₃ | CF₃ | 3-Cl, 5-OCF₃ |
| CH₃ | CF₃ | 3-F, 5-CF₃ |
| CH₃ | CF₃ | 2-CH₃, 4-CN |
| CH₃ | CF₃ | 2-CH₃, 4-OCH₃ |
| CH₃ | CF₃ | 2-CH₃, 4-CF₃ |
| CH₃ | CF₃ | 2-CH₃, 4-C(CH₃)=NOCH₃ |
| CH₃ | CF₃ | 3-CH₃, 4-C(CH₃)=NOCH₃ |
| CH₃ | CF₃ | 2-OH, 5-CH₃ |
| CH₃ | CF₃ | 3-CH₃, 4-O-t-C₄H₉ |
| CH₃ | CF₃ | 2-C(COOCH₃)=NOCH₃ |
| CH₃ | CF₃ | 2,3-Butadienyl |
| CH₃ | CF₃ | 3,4-Butadienyl |

TABLE B

| A | R | B |
|---|---|---|
| CH₃ | H | 2-Pyridyl |
| CH₃ | H | 4-Cl-2-Pyridyl |
| CH₃ | H | 4-CH₃-2-Pyridyl |
| CH₃ | H | 4-CF₃-2-Pyridyl |

TABLE B-continued

| A | R | B |
|---|---|---|
| CH₃ | H | 4-OCH₃-2-Pyridyl |
| CH₃ | H | 5-Cl-2-Pyridyl |
| CH₃ | H | 5-CH₃-2-Pyridyl |
| CH₃ | H | 5-CF₃-2-Pyridyl |
| CH₃ | H | 5-OCH₃-2-Pyridyl |
| CH₃ | H | 6-Cl-2-Pyridyl |
| CH₃ | H | 6-CH₃-2-Pyridyl |
| CH₃ | H | 6-CF₃-2-Pyridyl |
| CH₃ | H | 6-OCH₃-2-Pyridyl |
| CH₃ | H | 4,6-Cl₂-2-Pyridyl |
| CH₃ | H | 4-CH₃, 6-Cl-2-Pyridyl |
| CH₃ | H | 4-Cl, 6-CH₃-2-Pyridyl |
| CH₃ | H | 5,6-Cl₂-2-Pyridyl |
| CH₃ | H | 5,6-(CH₃)₂-2-Pyridyl |
| CH₃ | H | 3-Pyridyl |
| CH₃ | H | 2-Cl-3-Pyridyl |
| CH₃ | H | 4-CH₃-3-Pyridyl |
| CH₃ | H | 5-Cl-3-Pyridyl |
| CH₃ | H | 5-Br-3-Pyridyl |
| CH₃ | H | 5-CH₃-3-Pyridyl |
| CH₃ | H | 5-CF₃-3-Pyridyl |
| CH₃ | H | 5-OCH₃-3-Pyridyl |
| CH₃ | H | 6-F-3-Pyridyl |
| CH₃ | H | 6-Cl-3-Pyridyl |
| CH₃ | H | 6-Br-3-Pyridyl |
| CH₃ | H | 6-CH₃-3-Pyridyl |
| CH₃ | H | 6-t-C₄H₉-3-Pyridyl |
| CH₃ | H | 6-CF₃-3-Pyridyl |
| CH₃ | H | 6-OCH₃-3-Pyridyl |
| CH₃ | H | 4,6-(CH₃)₂-3-Pyridyl |
| CH₃ | H | 5,6-Cl₂-3-Pyridyl |
| CH₃ | H | 5-Cl, 6-CH₃-3-Pyridyl |
| CH₃ | H | 4-Pyridyl |
| CH₃ | H | 2-Cl-4-Pyridyl |
| CH₃ | H | 2-CH₃-4-Pyridyl |
| CH₃ | H | 2-CF₃-4-Pyridyl |
| CH₃ | H | 2-OCH₃-4-Pyridyl |
| CH₃ | H | 2,6-Cl₂-4-Pyridyl |
| CH₃ | H | 2,6-(CH₃)₂-4-Pyridyl |
| CH₃ | H | 2,6-(t-C₄H₉)₂-4-Pyridyl |
| CH₃ | H | 2-Cl, 6-CH₃-4-Pyridyl |
| CH₃ | H | 3-Pyridazinyl |
| CH₃ | H | 5-CH₃-3-Pyridazinyl |
| CH₃ | H | 6-Cl-3-Pyridazinyl |
| CH₃ | H | 4-Pyridazinyl |
| CH₃ | H | 6-CF₃-4-Pyridazinyl |
| CH₃ | H | 2-Pyrimidinyl |
| CH₃ | H | 4-Cl-2-Pyrimidinyl |
| CH₃ | H | 4-CH₃-2-Pyrimidinyl |
| CH₃ | H | 4-CF₃-2-Pyrimidinyl |
| CH₃ | H | 4-OCH₃-2-Pyrimidinyl |
| CH₃ | H | 4,6-(CH₃)₂-2-Pyrimidinyl |
| CH₃ | H | 4-CF₃, 6-OCH₃-2-Pyrimidinyl |
| CH₃ | H | 5-Cl-2-Pyrimidinyl |
| CH₃ | H | 5-CH₃-2-Pyrimidinyl |
| CH₃ | H | 4-CH₃, 5-Cl-2-Pyrimidinyl |
| CH₃ | H | 4-Pyrimidinyl |
| CH₃ | H | 2-CH₃-4-Pyrimidinyl |
| CH₃ | H | 2-OCH₃-4-Pyrimidinyl |
| CH₃ | H | 6-Cl-4-Pyrimidinyl |
| CH₃ | H | 6-CH₃-4-Pyrimidinyl |
| CH₃ | H | 6-CF₃-4-Pyrimidinyl |
| CH₃ | H | 6-OCH₃-4-Pyrimidinyl |
| CH₃ | H | 2-CH₃, 6-CF₃-4-Pyrimidinyl |
| CH₃ | H | 2-n-C₃H₇, 6-CF₃-4-Pyrimidinyl |
| CH₃ | H | 2-OCH₃, 6-CH₃-4-Pyrimidinyl |
| CH₃ | H | 5-Pyrimidinyl |
| CH₃ | H | 4-CH₃-5-Pyrimidinyl |
| CH₃ | H | 2-CH₃-5-Pyrimidinyl |
| CH₃ | H | 2-OCH₃-5-Pyrimidinyl |
| CH₃ | H | 2-CH₃, 4-CF₃-5-Pyrimidinyl |
| CH₃ | H | 2-Pyrazinyl |
| CH₃ | H | 5-Cl-2-Pyrazinyl |
| CH₃ | H | 5-CH₃-2-Pyrazinyl |
| CH₃ | H | 6-CF₃-2-Pyrazinyl |
| CH₃ | H | 6-OCH₃-2-Pyrazinyl |
| CH₃ | H | 5,6-(CH₃)₂-2-Pyrazinyl |
| CH₃ | H | 2-Quinolinyl |
| CH₃ | H | 5-CH₃-2-Quinolinyl |

TABLE B-continued

| | | |
|---|---|---|
| CH₃ | H | 6-Cl-2-Quinolinyl |
| CH₃ | H | 6-CH₃-2-Quinolinyl |
| CH₃ | H | 7-CH₃-2-Quinolinyl |
| CH₃ | H | 5,7-Cl₂-2-Quinolinyl |
| CH₃ | H | 3-Quinolinyl |
| CH₃ | H | 6-CH₃-3-Quinolinyl |
| CH₃ | H | 7-Cl-3-Quinolinyl |
| CH₃ | H | 8-Cl-3-Quinolinyl |
| CH₃ | H | 8-OCH₃-Quinolinyl |
| CH₃ | H | 4-Quinolinyl |
| CH₃ | H | 3-Isoquinolinyl |
| CH₃ | H | 6-CH₃-3-Isoquinolinyl |
| CH₃ | H | 7-Cl-3-Isoquinolinyl |
| CH₃ | H | 8-OCH₃-3-Isoquinolinyl |
| CH₃ | H | 3-Cinnolinyl |
| CH₃ | H | 8-CH₃-3-Cinnolinyl |
| CH₃ | H | 2-Quinazolinyl |
| CH₃ | H | 6-CH₃-2-Quinazolinyl |
| CH₃ | H | 2-Quinazolinyl |
| CH₃ | H | 7-Cl-2-Quinoxalinyl |
| CH₃ | H | 6,8-(CH₃)₂-2-Quinoxalinyl |
| CH₃ | H | 1,5-Naphthyridin-2-yl |
| CH₃ | H | 2-Pivaloylamino-4-hydroxypteridin-6-yl |
| CH₃ | H | 2-Furyl |
| CH₃ | H | 4-Cl-2-Furyl |
| CH₃ | H | 4-CH₃-2-Furyl |
| CH₃ | H | 5-Cl-2-Furyl |
| CH₃ | H | 5-CH₃-2-Furyl |
| CH₃ | H | 4,5-Cl₂-2-Furyl |
| CH₃ | H | 3-Furyl |
| CH₃ | H | 4-CH₃-3-Furyl |
| CH₃ | H | 5-Cl-3-Furyl |
| CH₃ | H | 5-CH₃-3-Furyl |
| CH₃ | H | 2-Thienyl |
| CH₃ | H | 4-Cl-2-Thienyl |
| CH₃ | H | 4-CH₃-2-Thienyl |
| CH₃ | H | 5-Cl-2-Thienyl |
| CH₃ | H | 5-Br-2-Thienyl |
| CH₃ | H | 5-CH₃-2-Thienyl |
| CH₃ | H | 5-CF₃-2-Thienyl |
| CH₃ | H | 5-OCH₃-2-Thienyl |
| CH₃ | H | 5-NO₂-2-Thienyl |
| CH₃ | H | 4,5(CH₃)₂-2-Thienyl |
| CH₃ | H | 3-Thienyl |
| CH₃ | H | 5-Cl-3-Thienyl |
| CH₃ | H | 5-CH₃-3-Thienyl |
| CH₃ | H | 5-CF₃-3-Thienyl |
| CH₃ | H | 1-CH₃-2-Pyrryl |
| CH₃ | H | 1-CH₃-4-OCH₃-2-Pyrryl |
| CH₃ | H | 1,5-(CH₃)₂-2-Pyrryl |
| CH₃ | H | 1-CH₃-3-Pyrryl |
| CH₃ | H | 1-CH₃-5-Cl-3-Pyrryl |
| CH₃ | H | 1-C₆H₅-3-Pyrryl |
| CH₃ | H | 1-(4-Cl-C₆H₄)-3-Pyrryl |
| CH₃ | H | 2-Oxazolyl |
| CH₃ | H | 4-CF₃-2-Oxazolyl |
| CH₃ | H | 5-Cl-2-Oxazolyl |
| CH₃ | H | 5-CH₃-2-oxazolyl |
| CH₃ | H | 4-Oxazolyl |
| CH₃ | H | 2-Cl-4-Oxazolyl |
| CH₃ | H | 2-CH₃-4-Oxazolyl |
| CH₃ | H | 5-Oxazolyl |
| CH₃ | H | 2-Cl-5-Oxazolyl |
| CH₃ | H | 2-CH₃-5-Oxazolyl |
| CH₃ | H | 2-Thiazolyl |
| CH₃ | H | 4-CH₃-2-Thiazolyl |
| CH₃ | H | 5-Cl-2-Thiazolyl |
| CH₃ | H | 5-OCH₃-2-Thiazolyl |
| CH₃ | H | 4-Thiazolyl |
| CH₃ | H | 2-CH₃-4-Thiazolyl |
| CH₃ | H | 2-Cl-4-Thiazolyl |
| CH₃ | H | 5-Thiazolyl |
| CH₃ | H | 2-Cl-5-Thiazolyl |
| CH₃ | H | 2-CH₂-5-Thiazolyl |
| CH₃ | H | 2,4-(CH₃)₂-5-Thiazolyl |
| CH₃ | H | 1-CH₃-2-Imidazolyl |
| CH₃ | H | 1,4-(CH₃)₂-2-Imidazolyl |
| CH₃ | H | 1-CH₃-4-Imidazolyl |
| CH₃ | H | 1,2-(CH₃)₂-4-Imidazolyl |
| CH₃ | H | 1-CH₃, 2-OCH₃-4-Imidazolyl |
| CH₃ | H | 1-CH₃-5-Imidazolyl |
| CH₃ | H | 1-CH₃, 2-Cl-5-Imidazolyl |
| CH₃ | H | 1-C₆H₅-4-Imidazolyl |
| CH₃ | H | 1-(4-F-C₆H₄)-4-Imidazolyl |
| CH₃ | H | 3-Isoxazolyl |
| CH₃ | H | 5-Cl-3-Isoxazolyl |
| CH₃ | H | 5-CH₃-3-Isoxazolyl |
| CH₃ | H | 5-Isoxazolyl |
| CH₃ | H | 3-CH₃-5-Isoxazolyl |
| CH₃ | H | 3-CF₃-5-Isoxazolyl |
| CH₃ | H | 3-Isothiazolyl |
| CH₃ | H | 5-CH₃-3-Isothiazolyl |
| CH₃ | H | 5-Isothiazolyl |
| CH₃ | H | 3-Cl-5-Isothiazolyl |
| CH₃ | H | 1-CH₃-3-Pyrazolyl |
| CH₃ | H | 1-CH₃, 5-Cl-Pyrazolyl |
| CH₃ | H | 1-CH₃-4-Pyrazolyl |
| CH₃ | H | 1-CH₃-5-Pyrazolyl |
| CH₃ | H | 1,3-(CH₃)₂-5-Pyrazolyl |
| CH₃ | H | 1-C₆H₅-3-Pyrazolyl |
| CH₃ | H | 1-(4-CH₃C₆H₄)-3-pyrazolyl |
| CH₃ | H | 1-C₆H₅-4-Pyrazolyl |
| CH₃ | H | 1-(4-ClC₆H₄)-4-Pyrazolyl |
| CH₃ | H | 1,2,4-oxadiazol-3-yl |
| CH₃ | H | 5-CH₃-1,2,4-Oxadiazol-3-yl |
| CH₃ | H | 1,2,4-Oxadiazol-5-yl |
| CH₃ | H | 3-CH₃-1,2,4-Oxadiazol-5-yl- |
| CH₃ | H | 1,3,4-Oxadiazolyl |
| CH₃ | H | 5-CH₃-1,3,4-Oxadiazol-2-yl |
| CH₃ | H | 1,2,4-Thiadiazol-3-yl |
| CH₃ | H | 1,2,4-Thiadiazol-5-yl |
| CH₃ | H | 1,3,4-Thiadiazolyl |
| CH₃ | H | 5-i-C₃H₇-1,3,4-Thiadiazol-2-yl |
| CH₃ | H | 1-CH₃-1,2,4-Triazol-3-yl |
| CH₃ | H | 1-CH₃-5-CF₃-1,2,4-Triazol-3-yl |
| CH₃ | H | 1-CH₃-1,2,4-Triazol-5-yl |
| CH₃ | H | 1-C₆H₅-1,2,4-Triazol-3-yl |
| CH₃ | H | 1-CH₃-Tetrazol-5-yl |
| CH₃ | H | 1-C₆H₅-Tetrazol-5-yl |
| CH₃ | H | 1,2,4-Triazin-3-yl |
| CH₃ | H | 1,3,5-Triazin-2-yl |
| CH₃ | H | 4,6-(CH₃)₂-1,3,5-Triazin-2-yl |
| CH₃ | H | 4,6-(CF₃)₂-1,3,5-Triazin-2-yl |
| CH₃ | H | 4,6-(OCH₃)₂-1,3,5-Triazin-2-yl |
| CH₃ | H | 1,2,4,5-Tetrazin-3-yl |
| CH₃ | H | 6-CH₃-1,2,4,5-Tetrazin-3-yl |
| CH₃ | H | 2-Benzofuryl |
| CH₃ | H | 6-Cl-2-Benzofuryl |
| CH₃ | H | 6-CH₃-2-Benzofuryl |
| CH₃ | H | 7-CH₃-2-Benzyofuryl |
| CH₃ | H | 2-Thionaphthenyl |
| CH₃ | H | 6-Cl-2-Thionaphthenyl |
| CH₃ | H | 6-CH₃-2-Thionaphthenyl |
| CH₃ | H | 7-Br-2-Thionaphthenyl |
| CH₃ | H | 1-CH₃-2-Indolyl |
| CH₃ | H | 1,7-(CH₃)₂-2-Indolyl |
| CH₃ | H | 1-CH₃-3-Indolyl |
| CH₃ | H | 2-Benzoxazolyl |
| CH₃ | H | 6-CH₃-2-Benzoxazolyl |
| CH₃ | H | 6-Br-2-Benzoxazolyl |
| CH₃ | H | 7-Cl-2-Benzoxazolyl |
| CH₃ | H | 2-Benzothiazolyl |
| CH₃ | H | 6-CF₃-2-Benzothiazolyl |
| CH₃ | H | 6-CH₃-2-Benzothiazolyl |
| CH₃ | H | 7-Br-2-Benzothiazolyl |
| CH₃ | H | 1-CH₃-2-Benzimidazolyl |
| CH₃ | H | 1-CH₃-6-Cl-2-Benzimidazolyl |
| CH₃ | H | 1-CH₃-7-CH₃-2-Benzimidazolyl |
| CH₃ | H | 3-[1,2]-Benzisoxazolyl |
| CH₃ | H | 3-[1,2]-Benzisothiazolyl |
| CH₃ | H | 1-CH₃-3-Benzpyrazolyl |
| CH₃ | H | 2-Purinyl |
| CH₃ | H | 6-CH₃-2-Purinyl |
| CH₃ | H | 6-Purinyl |
| CH₃ | H | 2-CH₃-6-Purinyl |
| CH₃ | H | 2,4-(CH₃)₂-6-Purinyl |
| CH₃ | CH₃ | 2-Pyridyl |

TABLE B-continued

| | | |
|---|---|---|
| CH₃ | CH₃ | 4-CH₃-2-Pyridyl |
| CH₃ | CH₃ | 5-CF₃-2-Pyridyl |
| CH₃ | CH₃ | 6-Cl-2-Pyridyl |
| CH₃ | CH₃ | 6-OCH₃-2-Pyridyl |
| CH₃ | CH₃ | 5,6-Cl-2-Pyridyl |
| CH₃ | CH₃ | 3-Pyridyl |
| CH₃ | CH₃ | 5-Br-3-Pyridyl |
| CH₃ | CH₃ | 6-F-3-Pyridyl |
| CH₃ | CH₃ | 6-t-C₄H₉-3-Pyridyl |
| CH₃ | CH₃ | 6-OCH₃-3-Pyridyl |
| CH₃ | CH₃ | 6-CF₃-3-Pyridyl |
| CH₃ | CH₃ | 4-Pyridyl |
| CH₃ | CH₃ | 2-CH₃-4-Pyridyl |
| CH₃ | CH₃ | 2-Cl, 6-CH₃-4-Pyridyl |
| CH₃ | CH₃ | 3-Pyridazinyl |
| CH₃ | CH₃ | 6-Cl-3-Pyridazinyl |
| CH₃ | CH₃ | 4-Pyridazinyl |
| CH₃ | CH₃ | 2-Pyrimidinyl |
| CH₃ | CH₃ | 4-CH₃-2-Pyrimidinyl |
| CH₃ | CH₃ | 4-CF₃, 6-OCH₃-2-Pyrimidinyl |
| CH₃ | CH₃ | 5-Cl-2-Pyrimidinyl |
| CH₃ | CH₃ | 4-Pyrimidinyl |
| CH₃ | CH₃ | 2-OCH₃-4-Pyrimidinyl |
| CH₃ | CH₃ | 6-Cl-4-Pyrimidinyl |
| CH₃ | CH₃ | 2-n-C₃H₇-6-CF₃-4-Pyrimidinyl |
| CH₃ | CH₃ | 5-Pyrimidinyl |
| CH₃ | CH₃ | 2-CH₃-5-Pyrimidinyl |
| CH₃ | CH₃ | 2-Pyrazinyl |
| CH₃ | CH₃ | 5-CH₃-2-Pyrazinyl |
| CH₃ | CH₃ | 6-OCH₃-2-Pyrazinyl |
| CH₃ | CH₃ | 2-Quinolinyl |
| CH₃ | CH₃ | 6-CH₃-2-Quinolinyl |
| CH₃ | CH₃ | 5,7-Cl₂-2-Quinolinyl |
| CH₃ | CH₃ | 3-Quinolinyl |
| CH₃ | CH₃ | 8-OCH₃-3-Quinolinyl |
| CH₃ | CH₃ | 4-Quinolinyl |
| CH₃ | CH₃ | 3-Isoquinolinyl |
| CH₃ | CH₃ | 7-Cl-3-Isoquinolinyl |
| CH₃ | CH₃ | 3-Cinnolinyl |
| CH₃ | CH₃ | 8-CH₃-3-Cinnolinyl |
| CH₃ | CH₃ | 2-Quinazolinyl |
| CH₃ | CH₃ | 2-Quinoxalinyl |
| CH₃ | CH₃ | 1,5-Napthyridin-2-yl |
| CH₃ | CH₃ | 2-Furyl |
| CH₃ | CH₃ | 4-CH₃-3-Furyl |
| CH₃ | CH₃ | 5-Cl-2-Furyl |
| CH₃ | CH₃ | 3-Furyl |
| CH₃ | CH₃ | 5-CH₃-3-Furyl |
| CH₃ | CH₃ | 2-Thienyl |
| CH₃ | CH₃ | 4-CH₃-2-Thienyl |
| CH₃ | CH₃ | 5-Br-2-Thienyl |
| CH₃ | CH₃ | 5-CF₃-2-Thienyl |
| CH₃ | CH₃ | 5-NO₂-2-Thienyl |
| CH₃ | CH₃ | 4,5-(CH₃)₂-2-Thienyl |
| CH₃ | CH₃ | 3-Thienyl |
| CH₃ | CH₃ | 5-CH₃-3-Thienyl |
| CH₃ | CH₃ | 1-CH₃-2-Pyrryl |
| CH₃ | CH₃ | 1-CH₃-3-Pyrryl |
| CH₃ | CH₃ | 1-(4-Cl-C₆H₄)-3-Pyrryl |
| CH₃ | CH₃ | 2-Oxazolyl |
| CH₃ | CH₃ | 5-CH₃-2-oxazolyl |
| CH₃ | CH₃ | 4-Oxazolyl |
| CH₃ | CH₃ | 2-Cl-4-Oxazolyl |
| CH₃ | CH₃ | 5-Oxazolyl |
| CH₃ | CH₃ | 2-CH₃-5-Oxazolyl |
| CH₃ | CH₃ | 2-Thiazolyl |
| CH₃ | CH₃ | 4-CH₃-2-Thiazolyl |
| CH₃ | CH₃ | 5-OCH₃-2-Thiazolyl |
| CH₃ | CH₃ | 4-Thiazolyl |
| CH₃ | CH₃ | 2-Cl-4-Thiazolyl |
| CH₃ | CH₃ | 5-Thiazolyl |
| CH₃ | CH₃ | 2,4-(CH₃)₂-5-Thiazolyl |
| CH₃ | CH₃ | 1-CH₃-2-Imidazolyl |
| CH₃ | CH₃ | 1-CH₃-4-Imidazolyl |
| CH₃ | CH₃ | 1-CH₃-5-Imidazolyl |
| CH₃ | CH₃ | 1-C₆H₅-5-Imidazolyl |
| CH₃ | CH₃ | 3-Isoxazolyl |
| CH₃ | CH₃ | 5-CH₃-3-Isoxazolyl |
| CH₃ | CH₃ | 5-Isoxazolyl |
| CH₃ | CH₃ | 3-Isothiazolyl |
| CH₃ | CH₃ | 5-Isothiazolyl |
| CH₃ | CH₃ | 1-CH₃-3-Pyrazolyl |
| CH₃ | CH₃ | 1-CH₃-4-Pyrazolyl |
| CH₃ | CH₃ | 1-CH₃-5-Pyrazolyl |
| CH₃ | CH₃ | 1,3-(CH₃)₂-5-Pyrazolyl |
| CH₃ | CH₃ | 1-(4-CH₃-C₆H₄)-4-Pyrazolyl |
| CH₃ | CH₃ | 1,2,4-Oxadiazol-3-yl |
| CH₃ | CH₃ | 1,2,4-Oxadiazol-5-yl |
| CH₃ | CH₃ | 1,3,4-Oxadiazolyl |
| CH₃ | CH₃ | 5-CH₃-1,3,4-Oxadiazol-2-yl |
| CH₃ | CH₃ | 1,2,4-Thiadiazol-3-yl |
| CH₃ | CH₃ | 1,2,4-Thiadiazol-5-yl |
| CH₃ | CH₃ | 1,3,4-Thiadiazolyl |
| CH₃ | CH₃ | 5-O—C₃H₇-1,3,4-Thiadiazolyl |
| CH₃ | CH₃ | 1-CH₃-1,2,4-Triazol-3-yl |
| CH₃ | CH₃ | 1-CH₃-5-CF₃-1,2,4-Triazol-3-yl |
| CH₃ | CH₃ | 1-C₆H₅-1,2,4-Triazol-S-yl |
| CH₃ | CH₃ | 1-CH₃-Tetrazol-5-yl |
| CH₃ | CH₃ | 1,2,4-Triazin-3-yl |
| CH₃ | CH₃ | 1,3,5-Triazin-2-yl |
| CH₃ | CH₃ | 4,6-(OCH₃)-1,3,5-Triazin-2-yl |
| CH₃ | CH₃ | 1,2,4,5-Tetrazin-3-yl |
| CH₃ | CH₃ | 2-Benzofuryl |
| CH₃ | CH₃ | 6-CH₃-2-Benzofuryl |
| CH₃ | CH₃ | 2-Thionaphthenyl |
| CH₃ | CH₃ | 7-Br-2-Thionaphthenyl |
| CH₃ | CH₃ | 1-CH₃-2-Indolyl |
| CH₃ | CH₃ | 2-Benzoxazolyl |
| CH₃ | CH₃ | 6-Br-2-Benzoxazolyl |
| CH₃ | CH₃ | 2-Benzothiazolyl |
| CH₃ | CH₃ | 6-CF₃-2-Benzothiazolyl |
| CH₃ | CH₃ | 1-CH₃-2-Benzimidazolyl |
| CH₃ | CH₃ | 3-[1,2]-Benzisoxazolyl |
| CH₃ | CH₃ | 2-Purinyl |
| CH₃ | CH₃ | 6-Purinyl |
| H | H | 2-Pyridyl |
| H | H | 5-CF₃-2-Pyridyl |
| H | H | 3-Pyridyl |
| H | H | 6-t-C₄H₉-3-Pyridyl |
| H | H | 4-Pyridyl |
| H | H | 2-CH₃-4-Pyridyl |
| H | H | 3-Pyridazinyl |
| H | H | 2-Pyrimidinyl |
| H | H | 4-CF₃, 6-OCH₃-2-Pyrimidinyl |
| H | H | 4-Pyrimidinyl |
| H | H | 6-Cl-4-Pyrimidinyl |
| H | H | 2-n-C₃H₇-6-CF₃-4-Primidinyl |
| H | H | 5-Pyrimidinyl |
| H | H | 2-Pyrazinyl |
| H | H | 2-Quinolinyl |
| H | H | 3-Quinolinyl |
| H | H | 3-Isoquinolinyl |
| H | H | 2-Quinoxalinyl |
| H | H | 2-Furyl |
| H | H | 5-Cl-2-Furyl |
| H | H | 3-Furyl |
| H | H | 2-Thienyl |
| H | H | 5-NO₂-2-Thienyl |
| H | H | 3-Thienyl |
| H | H | 1-(4-Cl—C₆H₄)-3-Pyrryl |
| H | H | 2-Oxazolyl |
| H | H | 4-Oxazolyl |
| H | H | 5-Oxazolyl |
| H | H | 2-Thiazolyl |
| H | H | 4-Thiazolyl |
| H | H | 5-Thiazolyl |
| H | H | 2,4-(CH₃)₂-5-Thiazolyl |
| H | H | 1-CH₃-4-Imidazolyl |
| H | H | 3-Isoxazolyl |
| H | H | 5-CH₃-3-Isoxazolyl |
| H | H | 5-Isoxazolyl |
| H | H | 3-Isothiazolyl |
| H | H | 1-CH₃-3-pyrazolyl |
| H | H | 1-(4-CH₃—C₆H₄)-4-Pyrazolyl |
| H | H | 1,2,4-oxadiazol-3-yl |
| H | H | 1,3,4-Thiadiazolyl |
| H | H | 1-C₆H₅-1,2,4-Triazol-5-yl |
| H | H | 1,3,5-Triazin-2-yl |

TABLE B-continued

| | | |
|---|---|---|
| H | H | 4,6-(OCH₃)₂-1,3,5-Triazin-2-yl |
| H | H | 2-Benzofuryl |
| H | H | 2-Thionaphthenyl |
| H | H | 7-Br-2-Thionaphthenyl |
| H | H | 1-CH₃-2-Indolyl |
| H | H | 2-Benzoxazolyl |
| H | H | 6-Br-2-Benzoxazolyl |
| H | H | 2-Benzothiazolyl |
| H | H | 6-CF₃-2-Benzothiazolyl |
| H | H | 1-CH₃-2-Benzimidazolyl |
| H | H | 6-Purinyl |
| H | CH₃ | 2-Pyridyl |
| H | CH₃ | 5-CF₃-2-Pyridyl |
| H | CH₃ | 3-Pyridyl |
| H | CH₃ | 6-t-C₄H₉-3-Pyridyl |
| H | CH₃ | 4-Pyridyl |
| H | CH₃ | 2-CH₃-4-Pyridyl |
| H | CH₃ | 3-Pyridazinyl |
| H | CH₃ | 2-Pyrimidinyl |
| H | CH₃ | 4-CF₃, 6-OCH₃-2-Pyrimidinyl |
| H | CH₃ | 4-Pyrimidinyl |
| H | CH₃ | 6-Cl-4-Pyrimidinyl |
| H | CH₃ | 2-n-C₃H₇-6-CF₃-4-Pyrimidinyl |
| H | CH₃ | 5-Pyrimidinyl |
| H | CH₃ | 2-Pyrazinyl |
| H | CH₃ | 2-Quinolinyl |
| H | CH₃ | 3-Quinolinyl |
| H | CH₃ | 3-Isoquinolinyl |
| H | CH₃ | 2-Quinoxalinyl |
| H | CH₃ | 2-Furyl |
| H | CH₃ | 5-Cl-2-Furyl |
| H | CH₃ | 3-Furyl |
| H | CH₃ | 2-Thienyl |
| H | CH₃ | 5-NO₂-2-Thienyl |
| H | CH₃ | 3-Thienyl |
| H | CH₃ | 1-(4-Cl—C₆H₄)-3-Pyrryl |
| H | CH₃ | 2-Oxazolyl |
| H | CH₃ | 4-Oxagolyl |
| H | CH₃ | 5-Oxazolyl |
| H | CH₃ | 2-Thiazolyl |
| H | CH₃ | 4-Thiazolyl |
| H | CH₃ | 5-Thiazolyl |
| H | CH₃ | 2,4-(CH₃)₂-5-Thiazolyl |
| H | CH₃ | 1-CH₃-4-Imidazolyl |
| H | CH₃ | 3-Isoxazolyl |
| H | CH₃ | 5-CH₃-3-Isoxazolyl |
| H | CH₃ | 5-Isoxazolyl |
| H | CH₃ | 3-Isothiazolyl |
| H | CH₃ | 1-CH₃-3-Pyrazolyl |
| H | CH₃ | 1-(4-CH₃—C₆H₄)-4-Pyrazolyl |
| H | CH₃ | 1,2,4-oxadiazol-3-yl |
| H | CH₃ | 1,3,4-Thiadiazolyl |
| H | CH₃ | 1-C₆H₅-1,2,4-Triazol-5-yl |
| H | CH₃ | 1,3,5-Triazin-2-yl |
| H | CH₃ | 4,6-(OCH₃)₂-1,3,5-Triazin-2-yl |
| H | CH₃ | 2-Benzofuryl |
| H | CH₃ | 2-Thionaphthenyl |
| H | CH₃ | 7-Br-2-Thionaphthenyl |
| H | CH₃ | 1-CH₃-2-Indolyl |
| H | CH₃ | 2-Benzoxazolyl |
| H | CH₃ | 6-Br-2-Benzoxazolyl |
| H | CH₃ | 2-Benzothiazolyl |
| H | CH₃ | 6-CF₃-2-Benzothiazolyl |
| H | CH₃ | 1-CH₃-2-Benzimidazolyl |
| H | CH₃ | 6-Purinyl |
| Cyclopropyl | H | 2-Pyridyl |
| Cyclopropyl | H | 5-CF₃-2-Pyridyl |
| Cyclopropyl | H | 3-Pyridyl |
| Cyclopropyl | H | 6-t-C₄H₉-3-Pyridyl |
| Cyclopropyl | H | 4-Pyridyl |
| Cyclopropyl | H | 2-CH₃-4-Pyridyl |
| Cyclopropyl | H | 3-pyridazinyl |
| Cyclopropyl | H | 2-Pyrimidinyl |
| Cyclopropyl | H | 4-CF₃—, 6-OCH₃-2-Pyrimidinyl |
| Cyclopropyl | H | 4-Pyrimidinyl |
| Cyclopropyl | H | 6-Cl-4-Pyrimidinyl |
| Cyclopropyl | H | 2-n-C₃H₇-6-CF₃-4-Pyrimidinyl |
| Cyclopropyl | H | 5-Pyrimidinyl |
| Cyclopropyl | H | 2-Pyrazinyl |
| Cyclopropyl | H | 2-Quinolinyl |
| Cyclopropyl | H | 3-Quinolinyl |
| Cyclopropyl | H | 3-Isoquinolinyl |
| Cyclopropyl | H | 2-Quinoxalinyl |
| Cyclopropyl | H | 2-Furyl |
| Cyclopropyl | H | 5-Cl-2-Furyl |
| Cyclopropyl | H | 3-Furyl |
| Cyclopropyl | H | 2-Thienyl |
| Cyclopropyl | H | 5-NO₂-2-Thienyl |
| Cyclopropyl | H | 3-Thienyl |
| Cyclopropyl | H | 1-(4-Cl—C₆H₄)-3-Pyrryl |
| Cyclopropyl | H | 2-Oxazolyl |
| Cyclopropyl | H | 4-Oxazolyl |
| Cyclopropyl | H | 5-Oxazolyl |
| Cyclopropyl | H | 2-Thiazolyl |
| cyclopropyl | H | 4-Thiazolyl |
| Cyclopropyl | H | 5-Thiazolyl |
| Cyclopropyl | H | 2,4-(CH₃)₂-5-Thiazolyl |
| Cyclopropyl | H | 1-CH₃-4-Imidazolyl |
| Cyclopropyl | H | 3-Isoxazolyl |
| Cyclopropyl | H | 5-CH₃-3-Isoxazolyl |
| Cyclopropyl | H | 5-Isoxazolyl |
| Cyclopropyl | H | 3-Isothiazolyl |
| Cyclopropyl | H | 1-CH₃-3-pyrazolyl |
| Cyclopropyl | H | 1-(4-CH₃—C₆H₄)-4-Pyrazolyl |
| Cyclopropyl | H | 1,2,4-Oxadiazol-3-yl |
| Cyclopropyl | H | 1,3,4-Thiadiazolyl |
| Cyclopropyl | H | 1-C₆H₅-1,2,4-Triazol-5-yl |
| Cyclopropyl | H | 1,3,5-Triazin-2-yl |
| Cyclopropyl | H | 4,6-(OCH₃)₂-1,3,5-Triazin-2-yl |
| Cyclopropyl | H | 2-Benzofuryl |
| Cyclopropyl | H | 2-Thionaphthenyl |
| Cyclopropyl | H | 7-Br-2-Thionaphthenyl |
| Cyclopropyl | H | 1-CH₃-2-Indolyl |
| Cyclopropyl | H | 2-Benzoxazolyl |
| Cyclopropyl | H | 6-Br-2-Benzoxazolyl |
| Cyclopropyl | H | 2-Benzothiazolyl |
| Cyclopropyl | H | 6-CF₃-2-Benzothiazolyl |
| Cyclopropyl | H | 1-CH₃-2-Benzimidazolyl |
| Cyclopropyl | H | 6-Purinyl |
| Cyclopropyl | CH₃ | 2-Pyridyl |
| Cyclopropyl | CH₃ | 5-CF₃-2-Pyridyl |
| Cyclopropyl | CH₃ | 3-Pyridyl |
| Cyclopropyl | CH₃ | 6-t-C₄H₉-3-Pyridyl |
| Cyclopropyl | CH₃ | 4-Pyridyl |
| Cyclopropyl | CH₃ | 2-CH₃-4-Pyridyl |
| Cyclopropyl | CH₃ | 3-Pyridazinyl |
| Cyclopropyl | CH₃ | 2-Pyrimidinyl |
| Cyclopropyl | CH₃ | 4-CF₃—, 6-OCH₃-2-Pyrimidinyl |
| Cyclopropyl | CH₃ | 4-Pyrimidinyl |
| Cyclopropyl | CH₃ | 6-Cl-4-Pyrimidinyl |
| Cyclopropyl | CH₃ | 2-n-C₃H₇-6-CF₃-4-Pyrimidinyl |
| Cyclopropyl | CH₃ | 5-Pyrimidinyl |
| Cyclopropyl | CH₃ | 2-Pyrazinyl |
| Cyclopropyl | CH₃ | 2-Quinolinyl |
| Cyclopropyl | CH₃ | 3-Quinolinyl |
| Cyclopropyl | CH₃ | 3-Isoquinolinyl |
| Cyclopropyl | CH₃ | 2-Quinoxalinyl |
| Cyclopropyl | CH₃ | 2-Furyl |
| Cyclopropyl | CH₃ | 5-Cl-2-Furyl |
| Cyclopropyl | CH₃ | 3-Furyl |
| Cyclopropyl | CH₃ | 2-Thienyl |
| Cyclopropyl | CH₃ | 5-NO₂-2-Thienyl |
| Cyclopropyl | CH₃ | 3-Thienyl |
| Cyclopropyl | CH₃ | 1-(4-Cl—C₆H₄)-3-Pyrryl |
| Cyclopropyl | CH₃ | 2-oxazolyl |
| Cyclopropyl | CH₃ | 4-Oxazolyl |
| Cyclopropyl | CH₃ | 5-Oxazolyl |
| Cyclopropyl | CH₃ | 2-Thiazolyl |
| Cyclopropyl | CH₃ | 4-Thiazolyl |
| Cyclopropyl | CH₃ | 5-Thiazolyl |
| Cyclopropyl | CH₃ | 2,4-(CH₃)₂-5-Thiazolyl |
| Cyclopropyl | CH₃ | 1-CH₃-4-Imidazolyl |
| Cyclopropyl | CH₃ | 3-Isoxazolyl |
| Cyclopropyl | CH₃ | 5-CH₃-3-Isoxazolyl |
| Cyclopropyl | CH₃ | 5-Isoxazolyl |
| Cyclopropyl | CH₃ | 3-Isothiazolyl |
| Cyclopropyl | CH₃ | 1-CH₃-3-Pyrazolyl |
| Cyclopropyl | CH₃ | 1-(4-CH₃—C₆H₄)-4-Pyrazolyl |

TABLE B-continued

| A | B | R |
|---|---|---|
| Cyclopropyl | CH₃ | 1,2,4-Oxadiazol-3-yl |
| Cyclopropyl | CH₃ | 1,3,4-Thiadiazolyl |
| Cyclopropyl | CH₃ | 1-C₆H₅-1,2,4-Triazol-5-yl |
| Cyclopropyl | CH₃ | 1,3,5-Triazin-2-yl |
| Cyclopropyl | CH₃ | 4,6-(OCH₃)₂-1,3,5-Triazin-2-yl |
| Cyclopropyl | CH₃ | 2-Benzofuryl |
| Cyclopropyl | CH₃ | 2-Thionaphthenyl |
| Cyclopropyl | CH₃ | 7-Br-2-Thionaphthenyl |
| Cyclopropyl | CH₃ | 1-CH₃-2-Indolyl |
| Cyclopropyl | CH₃ | 2-Benzoxazolyl |
| Cyclopropyl | CH₃ | 6-Br-2-Benzoxazolyl |
| Cyclopropyl | CH₃ | 2-Benzothiazolyl |
| Cyclopropyl | CH₃ | 6-CF₃-2-Benzothiazolyl |
| Cyclopropyl | CH₃ | 1-CH₃-2-Benzothiadazolyl |
| Cyclopropyl | CH₃ | 6-Purinyl |

| A | B | R |
|---|---|---|
| CH₃ | CH₃ | H |
| CH₃ | C₂H₅ | H |
| CH₃ | n-C₃H₇ | H |
| CH₃ | i-C₃H₇ | H |
| CH₃ | s-C₄H₉ | H |
| CH₃ | t-C₄H₉ | H |
| CH₃ | n-C₅H₁₁ | H |
| CH₃ | n-C₆H₁₃ | H |
| CH₃ | n-C₁₂H₂₅ | H |
| CH₃ | Cyclopropyl | H |
| CH₃ | Cyclobutyl | H |
| CH₃ | Cyclopentyl | H |
| CH₃ | Cyclohexyl | H |
| CH₃ | Cycloheptyl | H |
| CH₃ | CHO | H |
| CH₃ | CO—CH₃ | H |
| CH₃ | CO-i-C₃H₇ | H |
| CH₃ | CO-t-C₄H₉ | H |
| CH₃ | CO—C₆H₅ | H |
| CH₃ | CO-3-Pyridyl | H |
| CH₃ | CO-2-Furyl | H |
| CH₃ | CO-4-Thiazolyl | H |
| CH₃ | CO-2-Quinolyl | H |
| CH₃ | COOCH₃ | H |
| CH₃ | COOC₂H₅ | H |
| CH₃ | COO-n-C₃H₇ | H |
| CH₃ | COO-i-C₃H₇ | H |
| CH₃ | COO-n-C₄H₉ | H |
| CH₃ | COO-t-C₄H₉ | H |
| CH₃ | COO—CH₂C₆H₅ | H |
| CH₃ | CH₃ | CH₃ |
| CH₃ | C₂H₅ | CH₃ |
| CH₃ | n-C₃H₇ | CH₃ |
| CH₃ | i-C₃H₇ | CH₃ |
| CH₃ | s-C₄H₉ | CH₃ |
| CH₃ | t-C₄H₉ | CH₃ |
| CH₃ | n-C₅H₁₁ | CH₃ |
| CH₃ | n-C₆H₁₃ | CH₃ |
| CH₃ | n-C₁₂H₂₅ | CH₃ |
| CH₃ | Cyclopropyl | CH₃ |
| CH₃ | Cyclobutyl | CH₃ |
| CH₃ | Cyclopentyl | CH₃ |
| CH₃ | Cyclohexyl | CH₃ |
| CH₃ | Cyclopentyl | CH₃ |
| CH₃ | CHO | CH₃ |
| CH₃ | CO—CH₃ | CH₃ |
| CH₃ | CO-i-C₃H₇ | CH₃ |
| CH₃ | CO-t-C₄H₉ | CH₃ |
| CH₃ | CO—C₆H₅ | CH₃ |
| CH₃ | CO-3-Pyridyl | CH₃ |
| CH₃ | CO-2-Furyl | CH₃ |
| CH₃ | CO-4-Thiazolyl | CH₃ |
| CH₃ | CO-2-Quinolyl | CH₃ |
| CH₃ | COOCH₃ | CH₃ |
| CH₃ | COOC₂H₅ | CH₃ |
| CH₃ | COO-n-C₃H₇ | CH₃ |
| CH₃ | COO-i-C₃H₇ | CH₃ |
| CH₃ | COO-n-C₄H₉ | CH₃ |
| CH₃ | COO-t-C₄H₉ | CH₃ |
| CH₃ | COO—CH₂C₆H₅ | CH₃ |

TABLE B-continued

| A | B | R |
|---|---|---|
| H | CH₃ | H |
| H | i-C₃H₇ | H |
| H | t-C₄H₉ | H |
| H | n-C₆H₁₃ | H |
| H | Cyclopropyl | H |
| H | cyclohexyl | H |
| H | CO—CH₃ | H |
| H | CO-t-C₄H₉ | H |
| H | CO—C₆H₅ | H |
| H | CO-3-Pyridyl | H |
| H | CO-2-Furyl | H |
| H | COOCH₃ | H |
| H | COOi-C₃H₇ | H |
| H | COOt-C₄H₉ | H |
| H | COO—CH₂C₆H₅ | H |
| H | CH₃ | CH₃ |
| H | i-C₃H₇ | CH₃ |
| H | t-C₄H₉ | CH₃ |
| H | n-C₆H₁₃ | CH₃ |
| H | Cyclopropyl | CH₃ |
| H | Cyclohexyl | CH₃ |
| H | CO—CH₃ | CH₃ |
| H | O-t-C₄H₉ | CH₃ |
| H | CO—C₆H₅ | CH₃ |
| H | CO-3-Pyridyl | CH₃ |
| H | CO-2-Furyl | CH₃ |
| H | COOCH₃ | CH₃ |
| H | COOi-C₃H₇ | CH₃ |
| H | COOt-C₄H₉ | CH₃ |
| H | COO—CH₂C₆H₅ | CH₃ |

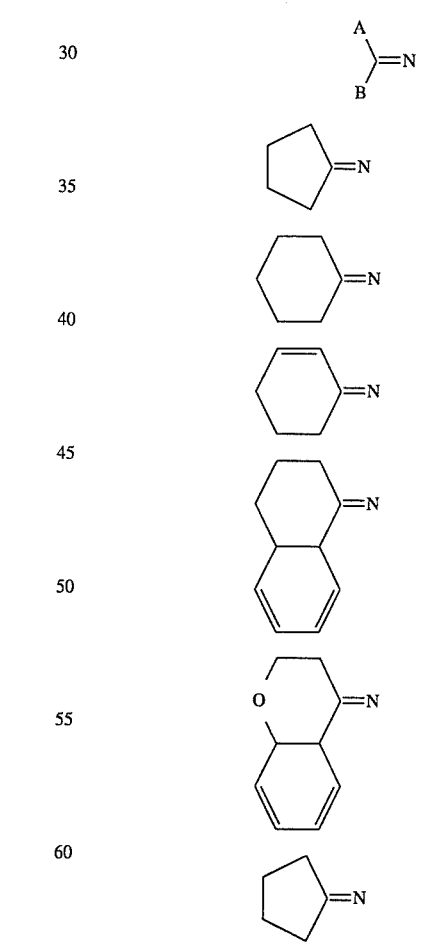

TABLE B-continued

[Structure: cyclohexene with =N-CH₃ substituent]

[Structure: cyclohexadiene with =N-CH₃ substituent]

[Structure: bicyclic with =N-CH₃ substituent]

[Structure: oxygen-containing bicyclic with =N-CH₃ substituent]

The compounds I are suitable as fungicides.

The compounds I are distinguished by an outstanding activity against a broad spectrum of phytopathogenic fungi, in particular from the class of Ascomycetes and Basidiomycetes. They are systemically active in some cases and can be employed as foliar and soil fungicides.

They are of particular importance for the control of a multiplicity of fungi on various crop plants such as wheat, rye, barley, oats, rice, corn, grass, cotton, soybean, coffee, sugar cane, grapes, fruit and decorative plants and vegetable plants such as cucumbers, beans and Cucurbitaceae, and on the seeds of these plants.

They are specifically suitable for the control of the following plant diseases: *Erysiphe graminis* (powdery mildew) in cereals, *Erysiphe cichoracearum* and *Sphaerotheca fuliginea* on Cucurbitaceae, *Podosphaera leucotricha* on apples, *Uncinula necator* on vines, *Puccinia species* on cereals., *Rhizoctonia species* on cotton and lawns, *Ustilago species* on cereals and sugar cane, *Venturia inaequalis* (scab) on apples, *Helminthosporium species* on cereals, *Septoria nodorum* on wheat, *Botrytis cinerea* (gray mold) on strawberries, vines, *Cercospora arachidicola* on groundnuts, *Pseudocercosporella herpotrichoides* on wheat, barley, *Pyricularia oryzae* on rice, *Phytophthora infestans* on potatoes and tomatoes, Fusarium and *Verticillium species* on various plants, *Plasmopara viticola* on vines, *Alternaria species* on vegetables and fruit.

The compounds I are applied by treating the fungi or the plants, seeds, materials or the soil to be protected from fungal attack with a fungicidally effective amount of the active compounds. They are applied before or after the infection of the materials, plants or seeds by the fungi.

They can be converted into the customary formulations, such as solutions, emulsions, suspensions, dusts, powders, pastes and granules. The application form depends on the particular intended use; they should in any case guarantee a fine and uniform dispersion of the ortho-substituted benzyl ester of a cyclopropanecarboxylic acid. The formulations are prepared in a known manner, eg. by extending the active compound with solvents and/or carriers, if desired using emulsifiers and dispersants, it also being possible to use other organic solvents as auxiliary solvents when water is used as a diluent. Suitable auxiliary substances for this purpose are essentially: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly disperse silicic acid, silicates); emulsifiers such as nonionic and anionic emulsifiers (eg. polyoxyethylene fatty alcohol ethers, alkylsulfonates and arylsulfonates) and dispersants such as ligninsulfite waste liquors and methylcellulose.

The fungicidal compositions in general contain from 0.1 to 95, preferably from 0.5 to 90%, by weight of active compound.

Depending on the type of effect desired, the application rates are from 0.01 to 2.0 kg of active compound per ha.

In seed treatment, active compound amounts of from 0.001 to 0.1 g, preferably 0.01 to 0.05 g, per kilogram of seed are in general needed.

The compositions according to the invention can also be present as fungicides together with other active compounds in the application form, eg. with herbicides, insecticides, growth regulators, fungicides or alternatively with fertilizers.

On mixing with fungicides, in many cases an increase in the fungicidal spectrum of action is obtained here.

The following list of fungicides with which the compounds according to the invention can be applied together should illustrate the combination possibilities, but not restrict them:

sulfur, dithiocarbamates and their derivatives, such as ferric dimethyldithiocarbamate, zinc dimethyldithiocarbamate, zinc ethylenebisdithiocarbamate, manganese ethylenebisdithiocarbamate, manganese zinc ethylenediamine bisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis(thiocarbamoyl) disulfide;

nitro derivatives, such as dinitro(-1-methylheptyl)phenyl crotonate, 2-sec-butyl-4,6-dinitrophenyl 3,3-dimethylacrylate, 2-sec-butyl-4,6-dinitrophenyl isopropylcarbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino) phosphinyl]-3-phenyl-1,2,4-triazole, 2,3-dicyano-1,4-dithioanthraquinone, 2-thio-1,3-dithiolo[4,5-b]quinoxaline, methyl -1-(butylcarbamoyl)- 2-benzimidazole carbamate, 2-methoxycarbonylaminobenzimidazole, 2-(fur-2-yl)benzimidazole, 2-(thiazol-4-yl)benzimidazole, N-(1,1,2,2-tetrachloroethylthio)tetrahydrophthalimide, N-trichloromethylthiotetrahydrophthalimide, N-trichloromethylthiophthalimide;

N-dichlorofluoromethylthio-N',N'-dimethyl-N-phenylsulfadiamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, 2-thiopyridine-1-oxide, 8-hydroxyquinoline or its copper salt, 2,3-dihydro-5-carboxanilido-6-methyl-1,4-oxathiin, 2,3-dihydro- 5-carboxanilido-6-methyl-1,4-oxathiin-4,4-dioxide, 2-methyl- 5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine- 2,2,2-trichloroethyl acetal, piperazine-1,4-diylbis( 1-(2,2,2-trichloroethyl))formamide, 1-(3, 4-dichloroanilino)- 1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, -1-[2-(2,4-dichlorophenyl)-4-ethyl-1,3-dioxolan-2-ylethyl]-1H-1, 2,4-triazole, 1-[2-(2,4-dichlorophenyl)-4-n-propyl- 1,3-dioxolan-2-ylethyl]-1H-1,2,4-triazole, N-(n-propyl)-N-( 2,4, 6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol -1-yl)-2-butanol, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl- 2-thioureido)benzene, 1,2-bis(3-methoxycarbonyl-2-thioureido)benzene, and also various fungicides, such as dodecylguanidine acetate, 3-[3-(3,5-dimethyl-2-oxycyclohexyl)-2-hydroxyethyl]glutarimide, hexachlorobenzene, DL-methyl-N-(2,6-dimethylphenyl)-N-2-furoyl alaninate, DL-N-(2,6-dimethylphenyl)-N-(2'- methoxyacetyl)alanine methyl ester, N-(2, 6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3, 5-dichlorophenyl)- 2,4-dioxo-1,3-oxazolidine, 3-[3,5-dichlorophenyl-(5-methyl- 5-methoxymethyl]-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-ethylaminocarbonyl-2-methoximino]acetamide, 1-[2-(2,4-dichlorophenyl)pentyl]-1H-1,2,4-triazole, 2,4-difluoro-α -(1H-1,2,4-triazolyl-1-methyl)benzhydryl alcohol, N-(3-chloro- 2,6-dinitro-4-trifluoromethylphenyl)-5-trifluoromethyl-3-chloro- 2-aminopyridine, 1-((bis(4-fluorophenyl)methylsilyl)methyl)- 1H-1,2,4-triazole.

The compounds of the formula I are additionally suitable to control pests from the class of insects, arachnida and nematodes effectively. They can be employed as pesticides in plant protection and in the hygiene, stored products protection and veterinary sector.

The harmful insects include from the order of the butterflies (Lepidoptera), for example, *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni, Zeiraphera canadensis.*

From the order of the beetles (Coleoptera), for example, *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis,* Diabrotica 12-punctata, *Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Otiorrhynchus ovatus, Phaedon cochleariae, Phyllotetra chrysocephala, Phyllophaga sp., Phyllopertha horticola, Phyllotetra nemorum, Phyllotetra striolata, Popillia japonica, Sitona lineatus, Sitophilus granaria.*

From the order of the dipterous insects (Diptera), for example, *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea, Tipula paludosa.*

From the order of the thrips (Thysanoptera), for example, *Frankliniella fusca, Frankliniella occidentalis, Frankliniella tritici, Scirtothrips citri, Thrips oryzae, Thrips palmi, Thrips tabaci.*

From the order of the hymenopterous insects (Hymenoptera), for example, *Athalia rosae, Atta cephalotes, Atta sexdens, Atta texana, Hoplocampa minuta, Hoplocampa testudinea, Monomorium pharaonis, Solenopsis geminata, Solenopsis invicta.*

From the order of the bed bugs (Heteroptera), for example, *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor.*

From the order of the plant-sucking insects (Homoptera), for example, *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dyasphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi,*

*Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum, Viteus vitifolii.*

From the order of the termites (Isoptera), for example, *Calotermes flavicollis, Leucotermes flavipes, Reticulitermes lucifugus, Termes natalensis.*

From the order of the orthopterous insects (Orthoptera), for example, *Acheta domestica, Blatta orientalis, Blattella germanica, Forficula auricularia, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.*

From the class of the Arachnoidea, for example spiders (Acarina) such as *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius, Tetranychus urticae.*

From the class of the nematodes, for example, root gall nematodes, eg. *Meloidogyne hapla, Meloidogyne incognita, Meloidogyne javanica,* cyst-forming nematodes, eg. *Globodera rostochiensis, Heterodera avenae, Heterodera glycines, Heterodera schachtii, Heterodera trifolii,* stem and leaf eelworms, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus, Pratylenchus goodeyi.*

The active compounds can be applied as such or in the form of their formulations or the application forms prepared therefrom, eg. in the form of directly sprayable solutions, powders, suspensions or dispersions, emulsions, oil dispersions, pastes, dusts, scattering compositions or granules by spraying, atomizing, dusting, scattering or pouring. The application forms depend entirely on the purposes of use; they should in any case as far as possible guarantee the finest dispersion of the active compounds according to the invention.

The active compound concentrations in the ready-for-application preparations can be varied within substantial ranges.

In general, they are from 0.0001 to 10%, preferably from 0.01 to 1%.

The active compounds can also be used with success in ultra-low volume processes (ULV), where it is possible to apply formulations containing more than 95% by weight of active compound or even the active compound without additives.

The application rate of active compound for controlling pests under outdoor conditions is from 0.1 to 2.0, preferably from 0.2 to 1.0 kg/ha.

For the preparation of directly sprayable solutions, emulsions, pastes or oil dispersions, mineral oil fractions of medium to high boiling point, such as kerosene or diesel oil, and also coal tar oils and oils of vegetable or animal origin, aliphatic, cyclic and aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone and water are suitable.

Aqueous application forms can be prepared from emulsion concentrates, pastes or wettable powders (oil dispersions) by addition of water. For the preparation of emulsions, pastes or oil dispersions, the substances can be homogenized in water as such or dissolved in an oil or solvent, by means of wetting agents, tackifiers, dispersants or emulsifiers. However, the concentrates consisting of active substance, wetting agent, tackifier, dispersant or emulsifier and possibly solvent or oil can also be prepared, which are suitable for dilution with water.

Suitable surface-active substances are alkali metal, alkaline earth metal and ammonium salts of lignosulfonic acid, naphthalenesulfonic acid, phenolsulfonic acid, dibutylnaphthalenesulfonic acid, alkylarylsulfonates, alkylsulfates, alkylsulfonates, fatty alcohol sulfates and fatty acids and their alkali metal and alkaline earth metal salts, salts of sulfated fatty alcohol glycol ethers, condensation products of sulfonated naphthalene and naphthalene derivatives with formaldehyde, condensation products of naphthalene or of naphthalenesulfonic acid with phenol and formaldehyde, polyoxyethylene octylphenyl ether, ethoxylated isooctylphenol, octylphenol, nonylphenol, alkylphenyl polyglycol ether, tributylphenyl polyglycol ether, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Powders, scattering compositions and dusts can be prepared by mixing or joint grinding of the active substances with a solid carrier.

The formulations in general contain from 0.01 to 95% by weight, preferably from 0.1 to 90% by weight, of the active compound. The active compounds are employed here in a purity of from 90% to 100%, preferably 95% to 100% (according to NMR spectrum).

Examples of formulations are:

I. 5 parts by weight of an active compound are intimately mixed with 95 parts by weight of finely divided kaolin. A dust which contains 5% by weight of the active compound is obtained in this way.

II. 30 parts by weight of an active compound are intimately mixed with a mixture of 92 parts by weight of powdered silica gel and 8 parts by weight of paraffin oil which has been sprayed on the surface of this silica gel. A preparation of the active compound having good adhesion is obtained in this way (active compound content 23% by weight).

III. 10 parts by weight of an active compound are dissolved in a mixture which consists of 90 parts by weight of xylene, 6 parts by weight of the addition product of 8 to 10 mol of ethylene oxide to 1 mol of oleic acid N-monoethanolamide, 2 parts by weight of calcium salt of dodecylbenzenesulfonic acid and 2 parts by weight of the addition product of 40 mol of ethylene oxide to 1 mol of castor oil (active compound content 9% by weight).

IV. 20 parts by weight of an active compound are dissolved in a mixture which consists of 60 parts by weight of cyclohexanone, 30 parts by weight of isobutanol, 5 parts by weight of the addition product of 7 mol of ethylene oxide to 1 mol of isooctylphenol and 5 parts by weight of the 15 addition product of 40 mol of ethylene oxide to 1 mol of castor oil (active compound content 16% by weight).

V. 80 parts by weight of an active compound are well mixed with 3 parts by weight of the sodium salt of diisobutyl-naphthalene-alpha-sulfonic acid, 10 parts by weight of the sodium salt of a lignosulfonic acid from a sulfite waste liquor and 7 parts by weight of powdered silica gel and the mixture is ground in a hammer mill (active compound content 80% by weight).

VI. 90 parts by weight of an active compound are mixed with parts by weight of N-methyl-α-pyrrolidone and a solution is obtained which is suitable for application in the form of very small drops (active compound content 90% by weight).

VII. 20 parts by weight of an active compound are dissolved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

VIII. 20 parts by weight of an active compound are well mixed with 3 parts by weight of the sodium salt of diisobutyl-naphthalene-α-sulfonic acid, 17 parts by weight of the sodium salt of a lignosulfonic acid from a sulfite waste liquor and 60 parts by weight of powdered silica gel and the mixture is ground in a hammer mill. By finely dispersing the mixture in 20,000 parts by weight of water, a spray liquor is obtained which contains 0.1% by weight of the active compound.

Granules, eg. coated, impregnated and homogeneous granules, can be produced by binding the active compounds to solid carriers. Solid carriers are eg. mineral earths, such as silica gel, silicic acids, silicates, talc, kaolin, attapulgite, limestone, lime, chalk, bole, loess, clay, dolomite, diatomaceous earth, calcium sulfate and magnesium sulfate, magnesium oxide, ground synthetic materials, fertilizers, such as eg. ammonium sulfate, ammonium phosphate, ammonium nitrate, ureas and vegetable products, such as grain meal, tree bark, wood and nut shell meal, cellulose powder and other solid carriers.

Oils of various types, herbicides, fungicides, other pesticides and bactericides can be added to the active compounds, if appropriate also just immediately before application (tank mix). These agents can be admixed to the compositions according to the invention in the weight ratio 1:10–10:1.

SYNTHESIS EXAMPLES

The procedures presented in the synthesis examples below are utilized with appropriate modification of the starting compounds to obtain further compounds I. The compounds thus obtained are shown in the following table C with physical data.

The following examples are intended to illustrate the preparation of the novel active compounds.

EXAMPLE 1

Preparation of [2-(α-Methoxyimino)Methoxycarbonylmethyl]Benzaldazine (No. I.11)

2.2 g (10 mmol) of methyl α-methoxyimino-(2-formylphenyl)acetate are dissolved in 50 ml of glacial acetic acid and 0.25 g (5 mmol) of hydrazine hydrate is added at room temperature (RT). The color of the reaction mixture becomes lighter, and after stirring for 5 min a light-yellow precipitate is formed. The mixture is stirred for a further 25 min at RT, and the precipitate is filtered off with suction and washed with pentane. The title compound is obtained as a light-yellow powder of m.p. 207°–209° C.; yield 1.6 g (73% of theory).

$^1$H NMR (CDCl$_3$, δ scale): 3.86 (s, 3 H, COOCH$_3$); 4.04 (s, 3 H, NOCH$_3$); 7.29 (mc, 1 H), 7.52 (mc, 2 H) and 7.91 (mc, 1 H; aromatic protons ); 8.47 ( s, 1 H, CH=N )

EXAMPLE 2

Preparation of -1-Methyl-1-(4'-Methylphenyl)-4-[2'-(α-Methoxyimino)Methoxycarbonylmethylene]Phenyl-2,3-Diazabutadiene (No. 1.04)

The two-phase mixture of 10.1 g (200 mmol) of 100% strength hydrazine hydrate, 2.5 ml of water and 13.4 g (100 mmol) of 4-methylacetophenone is heated to 60° C. for 10 h. It is allowed to cool, treated with water and extracted 3× with ether, and the organic phases are dried over sodium sulfate and concentrated in vacuo. 12.5 g (85% of theory) of 4-methylacetophenone hydrazone are obtained as an almost colorless oil.

1.6 g of the 4-methylacetophenone hydrazone prepared as described above are dissolved in 100 ml of tetrahydrofuran and added dropwise at RT to a solution of 2.2 g (10 mmol) of methyl α-methoxy-imino( 2-formylphenyl) acetate in 30 ml of glacial acetic acid. The mixture is stirred for 30 min, neutralized with saturated sodium carbonate solution with slight ice-cooling and extracted with diethyl ether, and the extract is dried over sodium sulfate to which a spatula tipful of sodium hydrogen carbonate has been added and is concentrated in vacuo. After separation of the symmetrical azines obtained as by-products (cf. scheme 1) by column chromatography (ethyl acetate/cyclohexane 96:4 to 80:20, silica gel 60), the title compound is obtained as yellow crystals, m.p. 127°–129° C., in 1.7 g (48% of theory) yield.

$^1$H NMR (CDCl$_3$, δ scale): 2.41 and 2.46 (2 s, 3 H each, Ar—CH$_3$ and N=C—CH$_3$); 3.82 (s, 3 H, COOCH$_3$); 4.04 (s, 3 H, NOCH$_3$); 7.1–7.3 (m, 3 H); 7.48 (mc, 2 H), 7.78 (d, 2 H) and 7.85 (mc, 1 H; aromatic protons); 8.38 (s, 1 H, CH=N).

EXAMPLE 3

Preparation of -1-Methyl-1-(4'-Methylphenyl)-4-[2'-(α-Methoxyimino)Methylaminocarbonylmethylene]Phenyl-2, 3-Diazabutadiene (No. I.09)

1.0 g (2.9 mmol) of 1-methyl-1-(4'-methylphenyl)-4-[2'-(α-methoxy-imino)methoxycarbonylmethylene]phenyl-2,3-diazabutadiene (product from Example 2) is dissolved in 20 ml of tetrahydrofuran (THF), 1.3 ml of 40% strength aqueous methylamine solution (14.5 mmol) are added and the reaction mixture is stirred overnight at RT; a small amount of a finely divided solid precipitates. This preci-pitate is filtered off with suction and washed with pentane, the title compound precipitating in the filtrate. Precipitation is completed by addition of further pentane. The precipitate is filtered off with suction, washed with pentane and dried by allowing to stand in air. Pale yellow crystals, m.p. 182°–185° C., yield 0.8 g (80% of theory).

$^1$H NMR (CDCl$_3$, δ scale): 2.42 and 2.47 (2 s, 3 H each, Ar—CH$_3$ and N=C—CH$_3$); 2.93 (d, 3 H, CONHCH$_3$); 3.96 (s, 3 H, NOCH$_3$); 6.87 (br, H, CONH); 7.24 (mc, 3 H), 7.50 (mc, 2 H), 7.80 (d, 2 H) and 8.03 (mc, 1 H; aromatic protons); 8.27 (s, 1 H, CH=N).

TABLE C

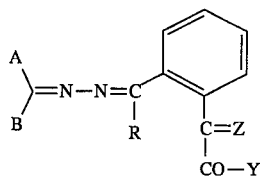

I

| No. | R | A | B | Y | Z | melting point [°C.] |
|---|---|---|---|---|---|---|
| I.01 | H | CH$_3$ | C$_6$H$_5$ | OCH$_3$ | NOCH$_3$ | 125–126 |
| I.02 | H | CH$_3$ | 4-Cl—C$_6$H$_4$ | OCH$_3$ | NOCH$_3$ | 162–166 |
| I.03 | H | CH$_3$ | 3,5-Cl$_2$—C$_6$H$_3$ | OCH$_3$ | NOCH$_3$ | 155–159 |
| I.04 | H | CH$_3$ | 4-CH$_3$—C$_6$H$_4$ | OCH$_3$ | NOCH$_3$ | 129 |
| I.05 | H | CH$_3$ | 4-C(CH$_3$)$_3$—C$_6$H$_4$ | OCH$_3$ | NOCH$_3$ | 122 |
| I.06 | H | CH$_3$ | C$_6$H$_5$ | NHCH$_3$ | NOCH$_3$ | 140–143 |
| I.07 | H | CH$_3$ | 4-Cl—C$_6$H$_4$ | NHCH$_3$ | NOCH$_3$ | 145–148 |
| I.08 | H | CH$_3$ | 3,5-Cl$_2$—C$_6$H$_3$ | NHCH$_3$ | NOCH$_3$ | 155–159 |
| I.09 | H | CH$_3$ | 4-CH$_3$—C$_6$H$_4$ | NHCH$_3$ | NOCH$_3$ | 182–185 |
| I.10 | H | CH$_3$ | 4-C(CH$_3$)$_3$—C$_6$H$_4$ | NHCH$_3$ | NOCH$_3$ | 131 |
| I.11 | H | H | 2-C(CO$_2$H$_3$)=NOCH$_3$—C$_6$H$_4$ | OCH$_3$ | NOCH$_3$ | 207–209 |

Examples of the action against harmful fungi

The fungicidal action of the compounds of the general formula I can be shown by the following tests:

The active compounds were prepared as a 20% strength emulsion in a mixture of 70% by weight of cyclohexanone, 20% by weight of Nekanil® LN (Lutensol® AP6, wetting agent with emulsifying and dispersant action based on ethoxylated alkylphenols) and 10% by weight of Emulphor® EL (Emulan® EL, emulsifier based on ethoxylated fatty alcohols) and appropriately diluted to the desired concentration with water.

A. *Botrytis cinerea*

Slices of green peppers were sprayed with the active compound preparation until dripping wet. After drying, the fruit slices were sprayed with a spore suspension of the fungus *Botrytis cinerea* (1.7×10$^6$ spores per ml of a 2% strength biomalt solution) and kept for 4 days at 18° C. at high atmospheric humidity. Assessment was carried out visually.

In this test, the untreated controls showed an attack of 90% while the fruit slices treated in each case with 500 ppm-containing active compound preparation of compounds 1.01, 1.04, 1.06 and I.08 were attacked to 15% at most.

B. *Plasmopara viticola*

Potted vines (variety: Müller Thurgau) were sprayed with the active compound preparation until dripping wet. After 8 days, the plants were sprayed with a zoospore suspension of the fungus *Plasmopara viticola* and kept for 5 days at 20°–30° C. at high atmospheric humidity. Before assessment, the plants were then kept for 16 h at high atmospheric humidity. Assessment was carried out visually.

In this test, the untreated controls showed an attack of 70% while the plants treated with 63 ppm-containing active compound preparation of the compounds I.01, I.03, I.04, I.06, I.07, I.08 and I.09 were attacked to 15% at most.

Examples of the action against animal pests

It was possible to show the action of the compounds of the general formula I against animal pests by the following tests:

The active compounds were prepared a. as a 0.1% strength solution in acetone or b. as a 10% strength emulsion in a mixture of 70% by weight of cyclohexanone, 20% by weight of Nekanil® LN (Lutensol® AP6, wetting agent with emulsifying and dispersant action based on ethoxylated alkylphenols) and 10% by weight of Emulphor® EL (Emulan® EL, emulsifier based on ethoxylated fatty alcohols) and appropriately diluted to the desired concentration with acetone in the case of a. or with water in the case of b.

After conclusion of the tests, in each case the lowest concentration was determined at which the compounds still produced an 80 to 100% inhibition or mortality in comparison to untreated control tests (activity threshold or minimum concentration).

We claim:

1. A compound of the formula

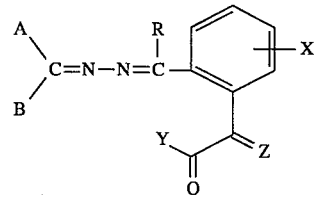

I where the substituents have the following meanings:

X is hydrogen, cyano, nitro, trifluoromethyl, halogen, C$_1$-C$_6$-alkyl or C$_1$-C$_6$-alkoxy;

Y is amino, methylamino or dimethylamino;

Z is CHCH$_3$, CHOCH$_3$ or NOCH$_3$;

R is hydrogen or C$_1$-C$_6$-alkyl;

A is hydrogen, C$_1$-C$_6$-alkyl, C$_1$-C$_6$-haloalkyl or C$_3$-C$_7$-cycloalkyl;

B is unsubstituted or substituted C$_1$-C$_6$-alkyl, C$_2$-C$_6$-alkenyl, C$_2$-C$_6$-alkynyl, C$_3$-C$_7$-cycloalkyl, C$_5$-C$_7$-cycloalkenyl, an unsubstituted or substituted, saturated or partially unsaturated heterocyclyl, unsubstituted or substituted aryl, which may be fused, unsubstituted or substituted 5- or 6-membered heteroaryl, which may be benzo- or hetero-fused, unsubstituted or substituted aryl-$C_1$-$C_6$-alkyl or heteroaryl-$C_1$-$C_6$-alkyl, or

C(=O)W;

where

W is hydrogen, unsubstituted or substituted $C_1$-$C_6$-alkyl, $C_1$-$C_6$-alkoxy, $C_1$-$C_6$-alkylthio, $C_1$-$C_6$-alkylamino or di-$C_1$-$C_6$-alkylamino, unsubstituted or substituted aryl, heteroaryl, aryloxy, arylthio, arylamino, aryl-N-($C_1$-$C_6$-alkyl)amino, heteroaryloxy, heteroarylthio, heteroarylamino or heteroaryl-N-($C_1$-$C_6$-alkyl)amino;

or

A and B, together with the C atom whose substituents they are, are an unsubstituted or substituted, saturated or unsaturated 3- to 7-membered isocyclic ring or 5- to 7-membered heterocyclic ring, which may be fused and which may also be quinonoid.

2. A composition for the control of harmful fungi, containing a solid or liquid carrier and a compound of the general formula I as claimed in claim 1.

3. The compound of claim 1, wherein X is hydrogen.

4. The compound of claim 1, wherein Y is methylamino.

5. The compound of claim 1, wherein Z is $NOCH_3$.

6. The compound of claim 1, wherein R is hydrogen.

7. The compound of claim 1, wherein A is hydrogen or methyl.

8. The compound of claim 1, wherein B is unsubstituted or substituted phenyl.

9. The compound of claim 1, wherein

X is hydrogen;

Y is methylamino;

Z is $NOCH_3$;

R is hydrogen; and

A is hydrogen or methyl.

10. A process for preparing the composition of claim 4, comprising the step of:

extending the compound with a solvent or carrier, or mixing or joint grinding of the compound with a solid carrier.

11. The process of claim 10, wherein said composition comprises 0.1 to 95% by weight of the compound.

12. The method of claim 10, wherein said composition comprises 0.5 to 90% by weight of the compound.

13. The compound of claim 1, wherein said heteroaryl is selected from the group consisting of 5-membered heteroaryls containing 1–4 nitrogen atoms or 1–3 nitrogen atoms and a sulfur or oxygen atom, benzo-fused 5-membered heteroaryls containing 1–3 nitrogen atoms or a nitrogen atom and an oxygen or sulfur atom, 5-membered heteroaryls bonded via nitrogen, benzo-fused 5-membered heteroaryls bonded via nitrogen, 6-membered heteroaryls containing 1–3 or 1–4 nitrogen atoms and benzo-fused 6-membered heteroaryls containing 1–3 nitrogen atoms.

14. The compound of claim 1, wherein said heterocyclyl is selected from the group consisting of oxiranyl, oxetanyl, tetrahydrofuryl, tetrahydrothienyl, pyrrolidinyl, isoxazolidinyl, isothiazolidinyl, pyrazolidinyl, oxazolidinyl, thiazolidinyl, imidazolidinyl, oxadiazolidinyl, thiazolidinyl, triazolidinyl, dihydrofuryl, dihydrothienyl, dihydropyrrolyl, dihydroisoxazolyl, dihydroisothiazolyl, dihydropyrazolyl, dihydrooxazolyl, dihydrothiazolyl, dihydroimidazolyl, piperidinyl, tetrahydropyridazinyl, tetrahydropyrimidinyl, tetrahydropyrazinyl, tetrahydrotriazinyl, dihydrooxazinyl, dithianyl, tetrahydropyranyl, dioxolanyl, thiazinyl, benzothiazinyl, benzoxazinyl, dioxotetrahydrothienyl, dihydrooxazinyl, morpholinyl, and dihydroquinazolinyl.

15. The compound of claim 1, wherein said heteroaryl is selected from the group consisting of furyl, thienyl, pyrrolyl, isoxazolyl, isothiazolyl, pyrazolyl, oxazolyl, thiazolyl, imidazolyl, thiadiazolyl, oxadiazolyl, triazolyl, tetrazolyl, pyridyl, pyridazinyl, pyrimidinyl, pyrazinyl, triazinyl, tetrazinyl, benzofuryl, isobenzofuryl, benzothienyl, indolyl, isoindolyl, benzisoxazolyl, benzisothiazolyl, benzothiazolyl, indazolyl, benzimidazolyl, benzotriazolyl, dibenzofuryl, dibenzothienyl, carbazolyl, acridinyl, phenanthridinyl, quinolinyl, isoquinolinyl, phthalazinyl, quinazolinyl, quinoxalinyl, cinnolinyl, naphthyridinyl, pteridinyl, pyrrolopyrazinyl, pyrrolopyridazinyl, pyrrolopyrimidinyl, pyrrolopyrazinyl, pyrrolotriazinyl, furopyridinyl, furopyridazinyl, furopyrimidinyl, furopyrazinyl, thienopyridinyl, thienopyridazinyl, thienopyrimidinyl, thienopyrazinyl, imidazopyridinyl, imidazolopyridazinyl, imidazopyrimidinyl, purinyl, imidazopyrazinyl, pyrazolopyridinyl, pyrazolopyridazinyl, pyrazolopyrimidinyl, pyrazolopyrazinyl, isoxazolopyrazinyl, oxazolopyridinyl, oxazolopyrimidinyl, isothiazolopyrimidinyl, and triazolopyrimidinyl.

* * * * *